United States Patent
Ngo et al.

(10) Patent No.: US 11,660,288 B2
(45) Date of Patent: May 30, 2023

(54) DRUG-CONTROLLED SYSTEMS AND USES THEREOF

(71) Applicant: TRUSTEES OF BOSTON UNIVERSITY, Boston, MA (US)

(72) Inventors: John T. Ngo, Cambridge, MA (US); Mary Dunlop, Newton, MA (US); Elliot Parker Tague, Brookline, MA (US); Nathan Michael Tague, Brookline, MA (US); Alexander Michael Marzilli, Cambridge, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/462,185

(22) Filed: Aug. 31, 2021

(65) Prior Publication Data

US 2022/0062234 A1    Mar. 3, 2022

Related U.S. Application Data

(60) Provisional application No. 63/072,695, filed on Aug. 31, 2020.

(51) Int. Cl.
| | |
|---|---|
| *A61K 31/404* | (2006.01) |
| *A61K 31/5377* | (2006.01) |
| *A61K 31/4965* | (2006.01) |
| *C07K 14/435* | (2006.01) |
| *A61K 47/64* | (2017.01) |
| *C07K 14/705* | (2006.01) |
| *C12N 9/12* | (2006.01) |
| *C07K 14/02* | (2006.01) |
| *C07K 14/47* | (2006.01) |

(52) U.S. Cl.
CPC ........ *A61K 31/404* (2013.01); *A61K 31/4965* (2013.01); *A61K 31/5377* (2013.01); *A61K 47/6425* (2017.08); *C07K 14/02* (2013.01); *C07K 14/43595* (2013.01); *C07K 14/47* (2013.01); *C07K 14/705* (2013.01); *C12N 9/1241* (2013.01); *C07K 2319/03* (2013.01); *C07K 2319/60* (2013.01); *C07K 2319/80* (2013.01)

(58) Field of Classification Search
None
See application file for complete search history.

(56) References Cited

FOREIGN PATENT DOCUMENTS

WO    2004035628 A1    4/2004

OTHER PUBLICATIONS

Chung et al. "Tunable and reversible drug control of protein production via a self-excising degron." Nat Chem Biol. (2015) 11(9): 713-720. https://pubmed.ncbi.nlm.nlh.gov/26214256/.
Cunningham-Bryant et al. "A Chemically Disrupted Proximity System for Controlling Dynamic Cellular Processes." J Am Chem Soc. (2019) 141(8): 3352-3355. doi:10.1021/jacs.8b12382.
Foight et al. "Cellular responses." Nat. Biotechnol. (2019) 37(10): 1209-1216. doi:10.1038/s41587-019-0242-8.
Jacobs et al. "StaPLs: Versatile genetically encoded modules for engineering drug-inducible proteins." Nat. Methods. (2018) 15(7): 523-526. doi:10.1038/s41592-018-0041-z.
Kugler et al. "High affinity peptide Inhibitors of the hepatitis C virus NS3-4A protease refractory to common resistant mutants." Biol. Chem. (2012) 287, 39224-39232.
Lin et al. "A drug-controllable tag for visualizing newlysynthesized proteins in cells and whole animals." PNAS. (2008) 105(22): 7744-7749. https://www.pnas.org/content/105/22/7744.
Tague et al. "Chemogenetic control of gene expression and cell signaling with antiviral drugs." Nat. Methods (2018) 15, 519-522.
Eroshenko et al. "Mutants of Cre recombinase with improved accuracy." Nature communications 4.1 (2013): 1-10.
Jullien et al. "Regulation of Cre recombinase by ligand-induced complementation of inactive fragments." Nucleic acids research 31.21 (2003): e131-e131.
Stavrou et al. "A rapamycin-activated caspase 9-based suicide gene." Molecular Therapy 26.5 (2018): 1266-1276.

*Primary Examiner* — Julie Ha
*Assistant Examiner* — Tara L Martinez
(74) *Attorney, Agent, or Firm* — Nixon Peabody LLP; Ronald I. Eisenstein; Nicole D. Kling

(57) ABSTRACT

The technology described herein is directed to polypeptide systems using drug-controlled peptide docking domains and cognate docking domain-binding peptides and their use to control cellular signaling, activity, and/or gene expression.

1 Claim, 21 Drawing Sheets

Specification includes a Sequence Listing.

| Peptide | Pseudonym used in this study | Reported affinity to $NS3^{WT}$ ($K_D$) | Amino acid sequence |
|---|---|---|---|
| CP5-46A-4D5E | $P_{MED}$ | 10.5 nM | GELDELVYLLDGPGYDPIHS |
| CP5-46-4D5E | $P_{HI}$ | 0.53 nM | GELDELVYLLDGPGYDPIHCDVV TRGGSHLFNF |

Fig. 15

| Promoter | Sequence |
|---|---|
| pW2 | TTATCAAAAGAGTA *TTGTCT* TAAAGTCTAACCTATAG *GATTCT* TACAGCCATCG AGAGGGACACGGCGAA |
| pW4 | TTATCAAAAGAGTA *TTGCAT* TAAAGTCTAACCTATAG *GAATCT* TACAGCCATCG AGAGGGACACGGCGAA |
| pW6 | TTATCAAAAGAGTA *TTGTCT* TAAAGTCTAACCTATAG *GAAAAT* TACAGCCATCG AGAGGGACACGGCGAA |

Fig. 16

DRUG-CONTROLLED SYSTEMS AND USES THEREOF

CROSS-REFERENCE TO RELATED APPLICATIONS

This application claims benefit under 35 U.S.C. § 119(e) of U.S. Provisional Application No. 63/072,695 filed Aug. 31, 2020, the contents of which are incorporated herein by reference in their entirety.

GOVERNMENT SUPPORT

This invention was made with government support under Grant Nos. GM128859 and AI137843 awarded by the National Institutes of Health and Grant No. 1804096 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Sep. 30, 2021, is named 701586-098320USPT_SL.txt and is 99,046 bytes in size.

TECHNICAL FIELD

The technology described herein relates to polypeptide systems that permit druggable control of signaling or activity.

BACKGROUND

Biological sensors, switches, and logical circuits are used to control cellular signaling, gene expression, and desired activities. These tools are of particular interest in order to control cellular therapies (e.g., CAR-T therapies or biological treatments targeting the microbiome). However, existing structures for such sensors, switches, and logical circuits suffer from failings that can render these tools unusable, or even actively harmful, in the clinic. For example, many sensors, switches, or logical circuits display "leaky" behavior. Alternatively, many of the control inputs/outputs proposed are not practicable outside of isolated cells; e.g., the are toxic, not disposed to systemic administration, or required further engineered cells.

SUMMARY

The technology described herein is directed to polypeptide systems of different configurations which offer significantly improved control, precision, and tenability than prior art designs.

In one aspect of any of the embodiments, described herein is a polypeptide comprising:
  a) a drug-controlled peptide docking domain;
  b) a cognate docking domain-binding peptide; and
  c) a recombinase comprising at least one decreased cooperativity mutation.
In some embodiments of any of the aspects, the polypeptide comprises, from N-terminus to C-terminus: the drug-controlled peptide docking domain; a first linker domain; the recombinase; a second linker domain; and the cognate docking domain-binding peptide. In some embodiments of any of the aspects, the polypeptide comprises, from N-terminus to C-terminus: the cognate docking domain-binding peptide; a first linker domain; the recombinase; a second linker domain; and the drug-controlled peptide docking domain. In some embodiments of any of the aspects, the polypeptide comprises:
  a) the drug-controlled peptide docking domain at the N-terminus to C-terminus of the recombinase with an intervening linker domain; and
  b) the cognate docking domain-binding peptide inserted into the recombinase at a position corresponding to amino acid 228 or 251 of SEQ ID NO: 58 (Cre).
In some embodiments of any of the aspects, the polypeptide comprises:
  a) the cognate docking domain-binding peptide at the N-terminus to C-terminus of the recombinase with an intervening linker domain; and
  b) the drug-controlled peptide docking domain inserted into the recombinase at a position corresponding to amino acid 228 or 251 of SEQ ID NO: 58 (Cre).
In some embodiments of any of the aspects, the recombinase is a tyrosine recombinase. In some embodiments of any of the aspects, the tyrosine recombinase is Cre, VCre, SCre, Flippase (Flp) XerA, XerC, or XerD. In some embodiments of any of the aspects, the decreased cooperativity mutation is a mutation at a residue corresponding to the R32, E69, 303, 304, or 305 residues of (SEQ ID NO: 58 (Cre)). In some embodiments of any of the aspects, the decreased cooperativity mutation is a mutation at a residue corresponding to the R32 residue of (SEQ ID NO: 58 (Cre)). In some embodiments of any of the aspects, the decreased cooperativity mutation is a mutation to a residue that does not have a positive charge. In some embodiments of any of the aspects, the decreased cooperativity mutation is a mutation to a naturally occurring residue that does not have a positive charge. In some embodiments of any of the aspects, the decreased cooperativity mutation is a mutation to a hydrophobic residue. In some embodiments of any of the aspects, the decreased cooperativity mutation is a mutation to a valine, methionine, leucine, isoleucine, or alanine residue. In some embodiments of any of the aspects, the decreased cooperativity mutation is a mutation to a valine or methionine residue. In some embodiments of any of the aspects, the recombinase comprising at least one decreased cooperativity mutation is $Cre^{R32M}$ or $Cre^{R32V}$. In one aspect of any of the embodiments, described herein is a system comprising the foregoing polypeptide and a drug that controls the drug-controlled peptide docking domain.

In one aspect of any of the embodiments, described herein is a system comprising:
  a) a first polypeptide comprising a first member of a pair of activity-complementing domains flanked on one terminus by a drug-controlled peptide docking domain and flanked on the other terminus by a cognate docking domain-binding peptide; and
  b) a second polypeptide comprising a second member of a pair of activity-complementing domains flanked on one terminus by a drug-resistant peptide docking domain.
In some embodiments of any of the aspects, the pair of activity-complementing domains are:
  i) a DNA-binding domain and a transcriptional effector domain;
  ii) a Gal4 DNA-binding domain and a VPR transcriptional effector domain;
  iii) a DNA-binding domain and a transcriptional repressor domain;

iv) a Gal4 DNA-binding domain and a KRAB transcriptional repressor domain;
v) a DNA-binding domain and a nuclease domain;
vi) a DNA-binding domain and a histone modification domain;
vii) two portions of an enzyme that are inactive when separate and enzymatically active when in physical contact;
viii) N-luciferase and C-luciferase;
ix) a ubiquitin ligase and its substrate; or
x) two portions of a nucleosome localization sequence.

In some embodiments of any of the aspects, the DNA-binding domain is selected from a Gal4, TetR, rTetR, or a zinc finger DNA-binding domain. In some embodiments of any of the aspects, the two portions of an enzyme that are inactive when separate and enzymatically active when in physical contact are portions of Caspase9; biotin ligase (e.g., BirA), TEV protease, and a ubiquitin ligase. In some embodiments of any of the aspects, the first polypeptide further comprises a first linker domain between the first member of a pair of activity-complementing domains and the drug-controlled peptide docking domain and second linker domain between the first member of a pair of activity-complementing domains and the cognate docking domain-binding peptide. In some embodiments of any of the aspects, the system further comprises a drug that controls the drug-controlled peptide docking domain.

In one aspect of any of the embodiments, described herein is a system comprising:
a) a first polypeptide which is a transmembrane polypeptide, the first polypeptide comprising:
  i) an extracellular domain comprising a first member of a specific binding pair of molecules, wherein the extracellular domain is heterologous to the Notch receptor;
  ii) a Notch receptor regulatory domain;
  iii) a transmembrane domain;
  iv) a cognate docking domain-binding peptide; and
  v) a first member of a pair of activity-complementing domains; and
b) a second polypeptide comprising:
  vi) a drug-controlled peptide docking domain; and
  vii) a second member of a pair of activity-complementing domains.

In some embodiments of any of the aspects, the pair of activity-complementing domains are:
a) a DNA-binding domain and a transcriptional effector domain;
b) a Gal4 DNA-binding domain and a VPR transcriptional effector domain;
c) a DNA-binding domain and a transcriptional repressor domain;
d) a Gal4 DNA-binding domain and a KRAB transcriptional repressor domain;
e) a DNA-binding domain and a nuclease domain;
f) a DNA-binding domain and a histone modification domain;
g) two portions of an enzyme that are inactive when separate and enzymatically active when in physical contact;
h) N-luciferase and C-luciferase;
i) a ubiquitin ligase and its substrate; or
j) two portions of a nucleosome localization sequence.

In some embodiments of any of the aspects, the DNA-binding domain is selected from a Gal4, TetR, rTetR, or a zinc finger DNA-binding domain. In some embodiments of any of the aspects, the pair of activity-complementing domains comprises a Gal4 DNA-binding domain and a transcriptional effector domain. In some embodiments of any of the aspects, the system further comprises a cell expressing the polypeptide(s). In some embodiments of any of the aspects, the system further comprises an extracellular second member of the specific binding pair of molecules. In some embodiments of any of the aspects, the extracellular second member of the specific binding pair of molecules is ligated, attached, or bound to a surface. In some embodiments of any of the aspects, the extracellular second member of the specific binding pair of molecules is expressed on the surface of a cell not expressing the polypeptide(s). In some embodiments of any of the aspects, the system further comprises a drug that controls the drug-controlled peptide docking domain.

In some embodiments of any of the aspects, the drug-controlled peptide docking domain comprises a catalytically inactive drug-controlled peptide docking domain. In some embodiments of any of the aspects, the drug-controlled peptide docking domain is selected from NS3; BCL-xL; and a GFP affinity domain. In some embodiments of any of the aspects, the drug-controlled peptide docking domain is catalytically inactive NS3 comprising a mutation of the catalytic serine, wherein the catalytic serine is the serine corresponding to S139 of SEQ ID NO: 91 (NS3). In some embodiments of any of the aspects, the mutation of the catalytic serine is an alanine substitution. In some embodiments of any of the aspects, the drug-controlled peptide docking domain or drug-resistant peptide docking domain is a drug-resistant NS3 selected from NS3$^{AT}$ (comprising V36M, T54A, and S122G relative to SEQ ID NO: 2) and NS3$^{TT}$(F43L, Q80K, S112R, and D168Y relative to SEQ ID NO: 91). In some embodiments of any of the aspects, the drug-controlled peptide docking domain is NS3 and the cognate docking domain-binding peptide is CP5-46-4D5E; PMED; or P$_{HI}$.

In some embodiments of any of the aspects, the drug-controlled peptide docking domain is BCL-xL and the cognate docking domain-binding peptide is BAD. In some embodiments of any of the aspects, the drug-controlled peptide docking domain is a GFP affinity domain and the cognate docking domain-binding peptide is a non-optimal affinity GFP polypeptide or anti-GFP nanobody.

In some embodiments of any of the aspects, the drug-controlled peptide docking domain is NS3 and the drug is selected from the group consisting of: grazoprevir, glecaprevir, danoprevir, asunaprevir, telaprevir, boceprevir, simeprevir, paritaprevir, voxilaprevir, narlaprevir, and ciluprevir. In some embodiments of any of the aspects, the drug-controlled peptide docking domain is BCL-xL and the drug is ABT-737, ABT-263 (navitoclax), or GX15-070 (obatoclax). In some embodiments of any of the aspects, the drug-controlled peptide docking domain is a fluorescent protein, the docking domain-binding peptide is a lower-affinity fluorescent protein affinity domain, and the drug is a higher-affinity fluorescent protein affinity domain. In some embodiments of any of the aspects, the fluorescent protein is GFP.

In some embodiments of any of the aspects, each linker domain is, independently, 8 to 11 amino acids in length. In some embodiments of any of the aspects, each linker domain, independently, comprises serine and/or glycine amino acids. In some embodiments of any of the aspects, each linker domain, independently, consists of serine and/or glycine amino acids.

In one aspect of any of the embodiments, described herein is a nucleic acid encoding the polypeptide or system described herein. In one aspect of any of the embodiments, described herein is a vector comprising the foregoing nucleic acid. In one aspect of any of the embodiments, described herein a cell or non-human organism comprising the polypeptide or system, the nucleic acid, or the vector described herein. In some embodiments of any of the aspects, the cell is a T cell.

In one aspect of any of the embodiments, described herein is a method of controlling the activity of a recombinase, the method comprising contacting a system described herein comprising a recombinase with a drug that controls the drug-controlled peptide docking domain, thereby inducing the activity of the recombinase. In some embodiments of any of the aspects, the recombinase induces a genetic modification that will induce or suppress expression of a target gene in the cell. In some embodiments of any of the aspects, the target gene encodes a receptor. In some embodiments of any of the aspects, the receptor is a chimeric antigen receptor. In some embodiments of any of the aspects, the target gene encodes an enzyme responsible for production of a bioproduct or therapeutic produced by the cell.

In one aspect of any of the embodiments, described herein is a method of controlling the activity of a pair of activity-complementing domains, the method comprising contacting a system as described herein comprising a pair of activity-complementing domains with a drug that controls the drug-controlled peptide docking domain, thereby inducing the activity of the pair of activity-complementing domains.

In one aspect of any of the embodiments, described herein is a method of controlling the activity of a pair of activity-complementing domains, the method comprising: contacting the system as described herein comprising a pair of activity-complementing domains with second member of the specific binding pair of molecules, thereby inducing the activity of the pair of activity-complementing domains; and/or contacting the system comprising a pair of activity-complementing domains with a drug that controls the drug-controlled peptide docking domain, thereby reducing the activity of the pair of activity-complementing domains. In some embodiments of any of the aspects, the activity of the pair of activity-complementing domains induces or suppresses expression of a target gene in the cell. In some embodiments of any of the aspects, the target gene encodes a receptor. In some embodiments of any of the aspects, the receptor is a chimeric antigen receptor. In some embodiments of any of the aspects, the target gene encodes an enzyme responsible for production of a bioproduct or therapeutic produced by the cell.

In one aspect of any of the embodiments, described herein a method of screening a candidate drug, the method comprising contacting a system as described herein comprising a pair of activity-complementing domains, wherein the activity of the pair of activity-complementing domains induces or suppresses expression of a target gene in the cell, with a candidate drug; and screening or selecting for the induction or suppression of expression of the target gene, wherein the induction or suppression of expression indicates that the candidate drug is a drug that controls the drug-controlled peptide docking domain, thereby inducing the activity of the pair of activity-complementing domains.

In one aspect of any of the embodiments, described herein is a method of treating cancer in a subject in need thereof, the method comprising: administering to the subject a T cell comprising a system as described herein, wherein the second member of the specific binding pair of molecules is a cancer antigen. In some embodiments of any of the aspects, the method further comprises administering a drug that controls the drug-controlled peptide docking domain, whereby anti-cancer activity of the T cell is reduced or suppressed. In some embodiments of any of the aspects, the T cell is autologous to the patient.

BRIEF DESCRIPTION OF THE DRAWINGS

(FIG. 1B) Transcriptional turn-off of Gal4 driven H2B-mCherry in HEK293FT cells via competitive inhibition of dNS3-VPR from Gal4DB-PMED. (FIG. 1C) Inhibition of repressor domain via competitive inhibition of dNS3-KRAB from Gal4DB-PMED controls expression of UAS-CMV-H2B-Citrine. (FIG. 1D) Design of drug-controlled Notch ICD function. Gal4DB-PMED drives expression in the presence of receptor ligand, dNS3-VPR, and absence of drug. (FIG. 1E) Combinatorial control of UAS-H2B-mCherry expression via surface coated ligand GFP and drug-controlled displacement of dNS3-VPR from Gal4DB-PMED ICD. (FIG. 1F) Drug controlled transcription via ligand mediated release of SynNotch Gal4DB-PMED ICD in dual HEK293FT coculture. Sender cells are expressing surface presented GFP ligand, and receiver cell contains transiently expressed SynNotch Gal4DB-PMED and dNS3-VPRto drive UAS-H2B-mCherry reporter. Receiver cells express iRFP670 (false colored blue) for labeling purposes. Scale bar: 20 pm. All quantitative fluorescent data was captured via flow cytometry of transiently transfected HEK293FT cells, 48 hours post-transfection/drug addition aside from UAS-H2B-mCherry, which was clonally incorporated into HEK293FT. Plotted values are the mean±SD of biologically independent replicates, n=3. Unless otherwise stated drug refers to 3 pM grazoprevir.

(FIG. 2B) Dose response of HEK293FT cells transfected with dNS3-NLuc and CLuc-PMED to various drugs. Lines are connected to guide the eye. (FIG. 2C) Dose response of NLuc fused to NS3WT or dNS3 in combination with CLuc fused to PMED or (FIG. 2D) higher affinity PHI (FIG. 2E). Temporal response to drug of the four different combinations of NLuc and CLuc fusions to NS3 and peptides. All dose responses are normalized to their respective no drug controls and transfected 48 hours before lysing for luciferase experiments. Drug was added at the time of transfection for dose response experiments. For temporal experiments, 3 pM of grazoprevir was added at the time of lysis. Plotted values are the mean±SD of biologically independent replicates, n=3.

(FIG. 3B) Design of intramolecular inhibited Cre driving recombination of virally integrated Cre reporter plasmid. Successful recombination results in GFP expression after excision of DsRed. (FIG. 3C) Comparison of transient transfection of dNS3-Cre-peptide with PMED and PHI with flow cytometry, 48 hours post-transfection and drug addition in HEK293T cells. (FIG. 3D) Variation of amino acid (aa) linkers between dNS3-Cre, and Cre-PHI with flow cytometry, 48 hours post-transfection and drug addition. Constructs chosen for highest dynamic range of GFP positive cells upon addition of drug and for low background of GFP positive cells in absence of drug. Optimal linker lengths are boxed. (FIG. 3E) dNS3-Cre-PHI variants with selected Cre mutants compared against dNS3-Cre control. (FIG. 3F) Selectivity of drug resistant N53-Cre-PHI constructs against asunaprevir (1 pM) and telaprevir (10 pM). Drug was added 24 hours post-transfection, and flow cytometry data was collected 48 hours post-drug addition. Unless otherwise noted, +Drug refers to 1 pM grazoprevir. Plotted values are biologically independent replicates, n=3.

(FIG. 4B) Constitutively expressed dNS3-Cre$^{R32M}$-PHI in *E. coli* with no drug treatment compared to 50 pM of grazoprevir or glecaprevir treatment, six hours post drug addition. Three constitutive promoters (Pconst.) were tested with low to medium level expression. These inducible Cre constructs are compared to lowly expressed constitutive Cre and Cre$^{R32M}$(FIG. 4C) Time course response of dNS3-Cre$^{R32M}$-PHI in *E. coli* during exponential growth with and without drug treatment (added at time 0). Values are shown starting after 120 min due to low OD prior to this time. Values shown are fluorescence (a.u., superfolder GFP) normalized to cell density (0D600), mean±SD, n=3 biologically independent replicates.

(FIG. 6A) Dose dependent response of transcriptional activation via ligand mediated release of SynNotch Gal4DB-PmEf ICD and varying amount of NS3 inhibitor, grazoprevir, compared to anti-GFP-Gal4DB-PMED only control. Ligand is surface-coated GFP. (FIG. 6B) Drug controlled transcription via ligand mediated release of SynNotch Gal4DB-PmEo ICD, dNS3, and NS3 inhibitor driving UAS-H2B-mCherry expression. Ligand is surface coated c-Myc antibody. (FIG. 6C) Larger image field of view of drug-controlled ICD SynNotch cultures (see FIG. 1F for reference). Scale bar: 20 pm. Plotted values are the mean±SD of biologically independent replicates, n=3.

(FIG. 8A) and (FIG. 8B) Rearranged data from FIGS. 2C and 2E to compare effects of NED vs. PHI peptides. Dose responses are normalized to their respective no drug controls. All cells were transfected 48 hours before lysing for luciferase experiments, and drug was added at the time of transfection. Plotted values are the mean±SD of biologically independent replicates, n=3.

(FIG. 9A) Linear regressions of the various combinations of dNS3, NS3 and peptides to NLuc and CLuc without drug for FIG. 2E. Each combination was used for normalization of each respective curve. Luminescence is not normalized here and stated in arbitrary luciferase units. (FIG. 9B) Split luciferase kinetic displacement curves rearranged from FIG. 2E displayed as mean (dots) with SD (lines). All cells were transfected 24 hours before lysing for luciferase experiments. Experiments are biologically independent replicates, n=3. For all experiments with drug, 3 pM of grazoprevir was added at time of lysis.

(FIG. 10A) Temporal turn-off of dNS3-NLuc and CLuc-PMED in response to four different antiviral NS3 inhibitors. All curves are normalized to (FIG. 10B), a linear regression of dNS3-NLuc and CLuc-PMED without drug. Luminescence is not normalized here and stated in arbitrary luciferase units. All cells were transfected 24 hours before lysing for luciferase experiments. To observe temporal displacement, 3 pM of each drug was added at the time of lysis. Plotted values are the mean of biologically independent replicates, n=3.

(FIG. 11A) Comparison of optimized linker Cre constructs with CreWT and CreR32M mutation. (FIG. 11B) Geometric mean fluorescent values of GFP associated with FIG. 3E. (FIG. 11C) Drug dependence of dNS3-Cre control without inhibitory peptide and (FIG. 11D) corresponding geometric mean fluorescent values of GFP, n=3 biologically independent replicates. For geometric mean fluorescence, plotted values are the geometric mean±SD of biologically independent replicates, n=3. For all Cre constructs, drug was added 24 hours after transfection and flow cytometry data was collected 48 hours after drug addition.

(FIG. 12A) Effect of NS38139A (dNS3) mutation on asunaprevir inducible (Al) and telaprevir inducible (TI) Cre recombinases. Plotted values are fraction of GFP expressing cells defined as cells with GFP signal greater than the top 1% of the non-transfected control. Basal GFP positive cells, determined by transfection marker control, were subtracted from the total, biologically independent replicates, n=3. (FIG. 12B) Associated geometric mean of fluorescence for the different drug inducible NS3 Cre recombinases with various drugs. Plotted values are the mean±SD of biologically independent replicates, n=3. Drug was added 24 hours post-transfection, and flow cytometry data was collected 48 hours post-drug addition. Grazoprevir: 1 pM; Asunaprevir: 1 pM; Telaprevir: 10 pM. Series are, from left to right: no drug, +Grazoprevir, +Asunaprevir, and +Telaprevir.

(FIG. 13A) Arabinose-inducible transcriptional control of dNS3-CreR32m and dNS3-CreR32m-PHI on low copy plasmids as compared to negative and positive control reporters, six hours post-drug addition. Arabinose: 1 mM, Grazoprevir: 50 pM (FIG. 13B) Growth curves of cells expressing dNS3-CreR32m-PHI without drug treatment and 10 pM or (FIG. 13C) 50 pM drug. Plotted values are the mean±SD of biological replicates, n=3.

FIG. 15 depicts the NS3-binding peptides used in Example 1. FIG. 16 depicts SEQ ID NOs: 13-14, respectively, in order of appearance.

FIG. 16 depicts constitutive bacterial promoters used in Example 1 in order of weakest to strongest. All sequences are derivatives of T7A1 phage promoter with mutations in the −35 and −10 regions (underlined). Transcriptional start site are the A's marked with an arrow. FIG. 16 depicts SEQ ID NOs: 15-17, respectively, in order of appearance.

FIG. 18 depicts SEQ ID NOs: 18-41, respectively, in order of appearance.

DETAILED DESCRIPTION

Figures 1A, 1B, 1C, 1D, 1E, 1F:
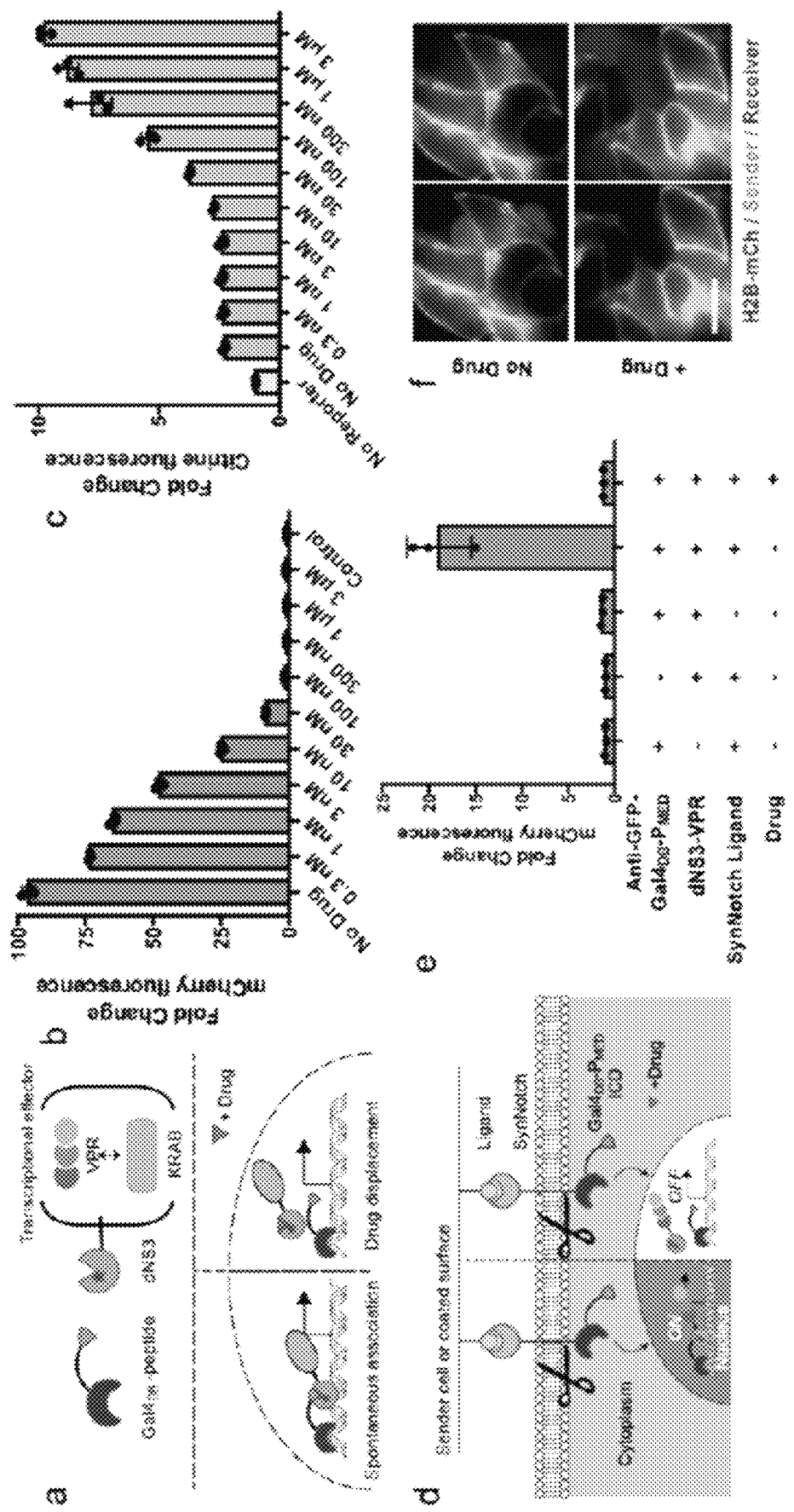
FIGS. 1A-1F depict transcriptional effector and cell signaling control (FIG. 1A) dNS3 can be fused to transcriptional modulators VPR or KRAB to affect Gal4DB-PMED mediated transcriptional modulation.

Various aspects of the technology described herein relate to a 3 part set of molecules comprising: a) a drug, b) a drug-controlled peptide docking domain, and c) a cognate docking domain-binding peptide. In the absence of the drug, the drug-controlled peptide docking domain will bind to a cognate docking domain-binding peptide. In the presence of the drug, the binding of the drug-controlled peptide docking domain and cognate docking domain-binding peptide is disrupted and the drug-controlled peptide docking domain will bind the drug. Accordingly, the drug and the docking domain-binding peptide should have binding sites on the drug-controlled peptide docking domain that at least partially overlap. Diverse exemplary molecule sets comprising a) a drug, b) a drug-controlled peptide docking domain, and c) a cognate docking domain-binding peptide are provided herein.

As used herein, "drug" refers to a compound that is not naturally present in the system it is introduced to. For example, if the polypeptides or systems described herein are present in a mammalian cell or mammal, the drug is a compound that is not naturally produced or found in the mammalian cell or mammal. In some embodiments of any of the aspects, the drug is a small molecule. In some embodiments of any of the aspects, the drug is a polypeptide molecule.

Exemplary 3 part sets of molecules are provided in Table 1 below.

TABLE 1

| Drug | Drug-controlled peptide docking domain | Docking domain-binding peptide |
|---|---|---|
| grazoprevir, glecaprevir, danoprevir, asunaprevir, telaprevir, boceprevir, simeprevir, paritaprevir, voxilaprevir, narlaprevir, or ciluprevir | NS3 and variants thereof | CP5-46-4D5E; PMED; or PHI |
| ABT-737, ABT-263 (navitoclax), or GX15-070 (obatoclax) | BCL-xL and variants thereof | BAD |
| Higher-affinity Fluorescent Protein (e.g., GFP) affinity domain (e.g, an antibody reagent that binds GFP) | Fluorescent Protein (e.g., GFP) | Lower-affinity Fluorescent Protein (e.g., GFP) affinity domain (e.g, an antibody reagent that binds GFP) |

In some embodiments of any of the aspects, the drug-controlled peptide docking domain is selected from NS3; BCL-xL; and a fluorescent protein (e.g., GFP).

As used herein, "NS3" refers to hepatitis C virus (HCV) nonstructural protein 3 (NS3). NS3, also known as p-70, is a viral nonstructural protein that is a 70 kDa cleavage product of the hepatitis C virus polyprotein. The 631-residue HCV NS3 protein is a dual-function protein, containing the trypsin/chymotrypsin-like serine protease in the N-terminal region and a helicase and nucleoside triphosphatase in the C-terminal region. The minimal sequences required for a functional serine protease activity comprise the N-terminal 180 amino acids of the NS3 protein, which can also be referred to as "NS3a". Deletion of up to 14 residues from the N terminus of the NS3 protein is tolerated while maintaining the serine protease activity. Accordingly, NS3 as described herein comprises at least residues 14-180 of the wildtype NS3 protein.

HCV has at least seven genotypes, labeled 1 through 7, which can also be further designated with "a" and "b" subtypes. Accordingly, NS3 can be an HCV genotype 1 NS3, an HCV genotype 1a NS3, an HCV genotype 1b NS3, an HCV genotype 2 NS3, an HCV genotype 2a NS3, an HCV genotype 2b NS3, an HCV genotype 3 NS3, an HCV genotype 3a NS3, an HCV genotype 3b NS3, an HCV genotype 4 NS3, an HCV genotype 4a NS3, an HCV genotype 4b NS3, an HCV genotype 5 NS3, an HCV genotype 5a NS3, an HCV genotype 5b NS3, an HCV genotype 6 NS3, an HCV genotype 6a NS3, an HCV genotype 6b NS3, an HCV genotype 7 NS3, an HCV genotype 7a NS3, or an HCV genotype 7b NS3. In some embodiments of any of the aspects, NS3 can be any known HCV NS3 genotype, variant, or mutant, e.g., that maintains the same function. In some embodiments of any of the aspects, the NS3 sequence comprises residues 1-180 of the NS3 protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin, Chapter 6: HCV NS3-4A Serine Protease, Hepatitis C Viruses: Genomes and Molecular Biology, Editor: Tan S L, Norfolk (UK): Horizon Bioscience, 2006; the content of which is incorporated herein by reference in its entirety). In some embodiments of any of the aspects, NS3 is a chimera of 2, 3, 4, 5, or more different NS3 genotypes, variants, or mutants as described herein, such that the protease maintains binding functions, and in some embodiments its protease functions.

In some embodiments of any of the aspects, NS3 as described herein comprises one of SEQ ID NOs: 89-104 or SEQ ID NOs: 154-162 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 89-102 or SEQ ID NOs: 154-162 that maintains the same binding functions, and in some embodiments the same protease functions.

In some embodiments of any of the aspects, NS3 as described herein comprises one of SEQ ID NOs: 89-102 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 89-102 that maintains the that maintains the same binding functions, and in some embodiments the same protease functions, as one of SEQ ID NOs: 8-102.

```
SEQ ID NO: 89, NS3 (genotype 1A), 189 aa; bold dotted underlined text indicates His-57
of the catalytic triad; italicized double underlined text indicates Asp-81 of the catalytic
triad; bold italicized dotted underlined indicates Ser-139 of the catalytic triad; zig zag
underlined text indicates Asp-168.
APITAYAQQTRGLLGCIITSLTGRDKNQVEGEVQIVSTATQTFLATCINGVCWAVYHGAGTRTIA
SPKGPVIQMYTNVDQDLVGWPAPQGSRSLTPCTCGSSDLYLVTRHADVIPVRRRGDSRGSLLSPR
PISYLKGSNGGPLLCPAGHAVGLFRAAVCTRGVAKAVDFIPVENLETTMRSPVFTDNSS SEQ ID NO: 90, NS3 (genotype 1A), 180 aa (see e.g., residues 1027-1206 of Hepatitis C
virus genotype 1 polyprotein, NCBI Reference Sequence: NP_671491.1.
APITAYAQQTRGLLGCIITSLTGRDKNQVEGEVQIVSTATQTFLATCINGVCWTVYHGAGTRTIAS

PKGPVIQMYTNVDQDLVGWPAPQGSRSLTPCTCGSSDLYLVTRHADVIPVRRRGDSRGSLLSPRP

ISYLKGSSGGPLLCPAGHAVGLFRAAVCTRGVAKAVDFIPVENLETTMR

SEQ ID NO: 91, NS3 (genotype 1B), 180 aa (see e.g., residues 1-180 Chain A, Ns3 Protease,
PDB: 4K8B_A); italicized bolded text indicates Ser-139 of the catalytic triad
APITAYSQQTRGLLGCIITSLTGRDKNQVEGEVQVVSTATQSFLATCVNGVCWTVYHGAGSKTL

AGPKGPITQMYTNVDQDLVGWQAPPGARSLTPCTCGSSDLYLVTRHADVIPVRRRGDSRGSLLS

PRPVSYLKGSSGGPLLCPSGHAVGIFRAAVCTRGVAKAVDFVPVESMETTMR

SEQ ID NO: 92, NS3 (genotype 2), 180 aa (see e.g., residues 1031-1210 of Hepatitis C virus
genotype 2 polyprotein, NCBI Reference Sequence: YP_001469630.1
APITAYAQQTRGLLGTIVVSMTGRDKTEQAGEIQVLSTVTQSFLGTSISGVLWTVYHGAGNKTLA

GSRGPVTQMYSSAEGDLVGWPSPPGTKSLEPCTCGAVDLYLVTRNADVIPARRRGDKRGALLSP

RPLSTLKGSSGGPVLCPRGHAVGVFRAAVCSRGVAKSIDFIPVETLDIVTR

SEQ ID NO: 93, NS3 (genotype 3), 180 aa (see e.g., residues 1033-1212 of Hepatitis C virus
genotype 3 polyprotein, NCBI Reference Sequence: YP_001469631.1)
APITAYAQQTRGLLGTIVTSLTGRDKNVVTGEVQVLSTATQTFLGTTVGGVIWTVYHGAGSRTL

AGAKHPALQMYTNVDQDLVGWPAPPGAKSLEPCACGSSDLYLVTRDADVIPARRRGDSTASLL

SPRPLACLKGSSGGPVMCPSGHVAGIFRAAVCTRGVAKSLQFIPVETLSTQAR

SEQ ID NO: 94, NS3 (genotype 4), 180 aa (see e.g., residues 1027-1206 of Hepatitis C virus
genotype 4 polyprotein, NCBI Reference Sequence: YP_001469632.1)
APITAYAQQTRGLFSTIVTSLTGRDTNENCGEVQVLSTATQSFLGTAVNGVMWTVYHGAGAKTI

SGPKGPVNQMYTNVDQDLVGWPAPPGVRSLAPCTCGSADLYLVTRHADVIPVRRRGDTRGALL

SPRPISILKGSSGGPLLCPMGHRAGIFRAAVCTRGVAKAVDFVPVESLETTMR

SEQ ID NO: 95, NS3 (genotype 5), 180 aa (see e.g., residues 1028-1207 of Hepatitis C virus
genotype 5 polyprotein, NCBI Reference Sequence: YP_001469633.1)
APITAYAQQTRGVLGAIVLSLTGRDKNEAEGEVQFLSTATQTFLGICINGVMWTLFHGAGSKTLA

GPKGPVVQMYTNVDKDLVGWPSPPGKGSLTRCTCGSADLYLVTRHADVIPARRRGDTRASLLS

PRPISYLKGSSGGPIMCPSGHVVGVFRAAVCTRGVAKALEFVPVENLETTMR

SEQ ID NO: 96, NS3 (genotype 6), 180 aa (see e.g., residues 1032-1211 of Hepatitis C virus
genotype 6 polyprotein, NCBI Reference Sequence: YP_001469634.1)
APITAYAQQTRGLVGTIVTSLTGRDKNEAEGEVQVVSTATQSFLATTINGVLWTVYHGAGSKNL

AGPKGPVCQMYTNVDQDLVGWPAPLGARSLAPCTCGSSDLYLVTRGADVIPARRRGDTRAALL

SPRPISTLKGSSGGPLMCPSGHVVGLFRAAVCTRGVAKALDFIPVENMDTTMR
```

SEQ ID NO: 97, NS3 (genotype 7), 180 aa (see e.g., residues 1031-1210 of Hepatitis C virus genotype 7 polyprotein, NCBI Reference Sequence: YP_009272536.1)
APISAYAQQTRGLISTLVVSLTGRDKNETAGEVQVLSTSTQTFLGTNVGGVMWGPYHGAGTRTV

AGRGGPVLQMYTSVSDDLVGWPAPPGSKSLEPCSCGSADLYLVTRNADVLPLRRKGDGTASLLS

PRPVSSLKGSSGGPVLCPQSHCVGIFRAAVCTRGVAKAVQFVPIEKMQVAQR

SEQ ID NO: 98, NS3 genotype 1a (HCV-H), 180 aa
APITAYAQQTRGLLGCIITSLTGRDKNQVEGEVQIVSTATQTFLATCINGVCWTVYHGAGTRTIAS

PKGPVIQMYTNVDQDLVGWPAPQGSRSLTPCTCGSSDLYLVTRHADVIPVRRRGDSRGSLLSPRP

ISYLKGSSGGPLLCPAGHAVGLFRAAVCTRGVTKAVDFIPVENLETTMR

SEQ ID NO: 99, NS3 genotype 1b (HCV-BK), 180 aa
APITAYSQQTRGLLGCIITSLTGRDKNQVEGEVQVVSTATQSFLATCVNGVCWTVYHGAGSKTL

AAPKGPITQMYTNVDQDLVGWPKPPGARSLTPCTCGSSDLYLVTRHADVIPVRRRGDSRGSLLS

PRPVSYLKGSSGGPLLCPFGHAVGIFRAAVCTRGVAKAVDFVPVESMETTMR

SEQ ID NO: 100, NS3 genotype 2a (HCV-J6), 180 aa
APITAYAQQTRGLLGTIVVSMTGRDKTEQAGEIQVLSTVTQSFLGTTISGVLWTVYHGAGNKTL

AGSRGPVTQMYSSAEGDLVGWPSPPGTKSLEPCTCGAVDLYLVTRNADVIPARRRGDKRGALLS

PRPLSTLKGSSGGPVLCPRGHAVGVFRAAVCSRGVAKSIDFIPVETLDIVTR

SEQ ID NO: 101, NS3 genotype 2b (HCV-J8), 180 aa
APITAYTQQTRGLLGAIVVSLTGRDKNEQAGQVQVLSSVTQTFLGTSISGVLWTVYHGAGNKTL

AGPKGPVTQMYTSAEGDLVGWPSPPGTKSLDPCTCGAVDLYLVTRNADVIPVRRKDDRRGALL

SPRPLSTLKGSSGGPVLCSRGHAVGLFRAAVCARGVAKSIDFIPVESLDVATR

SEQ ID NO: 102, NS3 genotype 3a (HCV-Nz11), 180 aa
APITAYAQQTRGLLGTIVTSLTGRDKNVVTGEVQVLSTATQTFLGTTVGGVIWTVYHGAGSRTL

AGAKHPALQMYTNVDQDLVGWPAPPGAKSLEPCACGSSDLYLVTRDADVIPARRRGDSTASLL

SPRPLACLKGSSGGPVMCPSGHVAGIFRAAVCTRGVAKSLQFIPVETLSTQAR

SEQ ID NO: 103, NS3 (genotype 1B; S139A), 179 aa; bold text indicates S139A.
ITAYSQQTRGLLGCIITSLTGRDKNQVEGEVQVVSTATQSFLATCVNGVCWTVYHGAGSKTLAG

PKGPITQMYTNVDQDLVGWQAPPGARSLTPCTCGSSDLYLVTRHADVIPVRRRGDSRGSLLSPRP

VSYLKGSAGGPLLCPSGHAVGIFRAAVCTRGVAKAVDFVPVESMETTMRS

SEQ ID NO: 104, NS3 (genotype 1A; S139A), 189 aa; bold text indicates S139A.
APITAYAQQTRGLLGCIITSLTGRDKNQVEGEVQIVSTATQTFLATCINGVCWAVYHGAGTRTIA

SPKGPVIQMYTNVDQDLVGWPAPQGSRSLTPCTCGSSDLYLVTRHADVIPVRRRGDSRGSLLSPR

PISYLKGSAGGPLLCPAGHAVGLFRAAVCTRGVAKAVDFIPVENLETTMRSPVFTDNSS

SEQ ID NO: 154, soluble NS3, 182 aa
MAPITAYAQQTRGLLGCIITSLTGRDKNQVEGEVQIVSTAAQTFLATCINGVCWTVYHGAGTRTI

ASPKGPVIQMYTNVDKDLVGWPAPQGSRSLTPCTCGSSDLYLVTRHADVIPVRRRGDSRGSLLSP

RPISYLKGSSGGPLLCPAGHAVGIFRAAVCTRGVAKAVDFIPVESLETTMRS

SEQ ID NO: 155, soluble NS3/NS4A, 195 aa
MKKKGSVVIVGRIVLNGAYAQQTRGLLGCIITSLTGRDKNQVEGEVQIVSTAAQTFLATCINGVC

WTVYHGAGTRTIASPKGPVIQMYTNVDKDLVGWPAPQGSRSLTPCTCGSSDLYLVTRHADVIPV

RRRGDSRGSLLSPRPISYLKGSSGGPLLCPAGHAVGIFRAAVCTRGVAKAVDFIPVESLETTMRSP

SEQ ID NO: 156, soluble NS3/NS4A, 195 aa
MKKKGSVVIVGRIVLNGAYAQQTRGEEGCQETSQTGRDKNQVEGEVQIVSTAAQTFLATCINGV

CWTVYHGAGTRTIASPKGPVIQMYTNVDKDLVGWPAPQGSRSLTPCTCGSSDLYLVTRHADVIP

VRRRGDSRGSLLSPRPISYLKGSSGGPLLCPAGHAVGIFRAAVCTRGVAKAVDFIPVESLETTMRS

P

-continued

SEQ ID NO: 157, soluble NS3/NS4A, 197 aa
MKKKGSVVIVGRINLSGDTAYAQQTRGEEGCQETSQTGRDKNQVEGEVQIVSTAAQTFLATCIN

GVCWTVYHGAGTRTIASPKGPVIQMYTNVDKDLVGWPAPQGSRSLTPCTCGSSDLYLVTRHAD

VIPVRRRGDSRGSLLSPRPISYLKGSSGGPLLCPAGHAVGIFRAAVCTRGVAKAVDFIPVESLETT

MRSP

SEQ ID NO: 158, soluble NS3/NS4A, 197 aa
MKKKGSVVIVGRINLSGDTAYAQQTRGEEGCQETSQTGRDKNQVEGEVQIVSTATQTFLATCIN

GVCWTVYHGAGTRTIASPKGPVTQMYTNVDKDLVGWQAPQGSRSLTPCTCGSSDLYLVTRHA

DVIPVRRRGDSRGSLLSPRPISYLKGSSGGPLLCPAGHAVGIFRAAVCTRGVAKAVDFIPVESLET

TMRSP

SEQ ID NO: 159, soluble NS3/NS4A, 197 aa
MKKKGSVVIVGRINLSGDTAYAQQTRGEEGCQETSQTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 160, soluble NS3/NS4A, 197 aa
MKKKGSVVIVGRINLSGDTAYAQQTRGEQGCQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 161, soluble NS3/NS4A, 197 aa
MKKKGSVVIVGRINLSGDTAYAQQTRGEQGTQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 162, NS3aH1, soluble NS3/NS4A (S139A), 196 aa
KKKGSVVIVGRINLSGDTAYAQQTRGEEGCQETSQTGRDKNQVEGEVQIVSTATQTFLATSINGV

LWTVYHGAGTRTIASPKGPVTQMYTNVDKDLVGWQAPQGSRSLTPCTCGSSDLYLVTRHADVI

PVRRRGDSRGSLLSPRPISYLKGSAGGPLLCPAGHAVGIFRAAVSTRGVAKAVDFIPVESLETTMR

SP

In some embodiments of any of the aspects, the drug-controlled peptide docking domain comprises a catalytically inactive drug-controlled peptide docking domain. In some embodiments of any of the aspects, the drug-controlled peptide docking domain comprises a catalytically inactive NS3.

In some embodiments of any of the aspects, a polypeptide as described herein comprises a drug-controlled peptide docking domain (e.g., NS3) that is catalytically active. For HCV NS3, the catalytic triad comprises His-57, Asp-81, and Ser-139. In regard to NS3, "catalytically active" refers to the ability to cleave at a protease cleavage site. In some embodiments of any of the aspects, the catalytically active NS3 can be any NS3 as described further herein that maintains the catalytic triad, i.e., comprises no non-synonymous substitutions at His-57, Asp-81, and/or Ser-139.

In some embodiments of any of the aspects, a polypeptide as described herein comprises a drug-controlled peptide docking domain that is catalytically inactive. In regard to NS3, "catalytically inactive" refers to the inability to cleave at a protease cleavage site. Accordingly, a catalytically inactive NS3 protease can comprise a nonsynonymous mutation at any one of His-57, Asp-81, and Ser-139. Non-limiting examples of NS3 inactivating mutations include H57A, D81A, S139A, or any combination thereof. As such, any one of SEQ ID NOs: 89-102 or SEQ ID NOs: 154-162 can comprise a H57A mutation; a D81A mutation; a S139A mutation; any nonsynonymous mutation to His-57, Asp-81, and Ser-139; or any combination thereof. In some embodiments of any of the aspects, any one of SEQ ID NOs: 89-102 or SEQ ID NOs: 154-162 can comprise a S139A mutation. In some embodiments of any of the aspects, a mutation to the catalytic triad does not disrupt other functions of the NS3, e.g., binding to a drug or binding to a docking domain-binding peptide.

In some embodiments of any of the aspects, a catalytically inactive NS3 comprises a mutation of the catalytic serine, wherein the catalytic serine is the serine corresponding to S139 of SEQ ID NO: 91. Peptides, macrocyclic, and linear ketoamide NS3 inhibitors recognize a large surface area of the enzyme, and thus mutation of S139 to a different residue is not expected to eliminate binding. In some embodiments of any of the aspects, the mutation of the catalytic serine is a substitution with alanine, cysteine, threonine, glycine, or valine. In some embodiments of any of the aspects, the mutation of the catalytic serine is a substitution with alanine.

In some embodiments of any of the aspects, the drug-controlled peptide docking domain is a drug-resistant peptide docking domain, i.e., the peptide docking domain is resistant to control by one or more drugs. In some embodiments of any of the aspects, a polypeptide or system further comprises a drug-resistant peptide docking domain, i.e., the peptide docking domain is resistant to control by one or more drugs. In some embodiments of any of the aspects, the drug-resistant peptide docking domain is a drug-resistant NS3. As noted above, wild-type NS3 is subject to control by multiple drugs. A drug-resistant NS3 can be resistant to one or to multiple drugs.

In some embodiments of any of the aspects, a drug-resistant peptide docking domain as described herein is resistant to 1, 2, 3, 4, 5, or more different drugs as described herein. Non-limiting examples of NS3 amino acid substitutions conferring resistance to NS3 protease inhibitors described herein include: V36L (e.g., genotype 1b), V36M (e.g., genotype 2a), T54S (e.g., genotype 1b), Y56F (e.g., genotype 1b), Q80L (e.g., genotype 1b), Q80R (e.g., genotype 1b), Q80K (e.g., genotype 1a, 1b, 6a), Y132I (e.g., genotype 1b), A156S (e.g., genotype 2a), A156G, A156T, A156V, D168A (e.g., genotype 1b), I170V (e.g., genotype 1b), S20N, R26K, Q28R, A39T, Q41R, I71V, Q80R, Q86R, P89L, P89S, S101N, A111S, P115S, S122R, R155Q, L144F, A150V, R155W, V158L, D168A, D168G, D168H, D168N, D168V, D168E, D168Y, E176K, T178S, M1791, M179V, and M179T. See e.g., Sun et al., Gene Expr. 2018, 18(1): 63-69; Kliemann et al., World J Gastroenterol. 2016 Oct. 28, 22(40): 8910-8917; U.S. Pat. Nos. 7,208,309; 7,494,660; the contents of each of which are incorporated herein by reference in their entireties.

In some embodiments of any of the aspects, a polypeptide as described herein comprises an NS3 comprising at least one resistance mutation as described herein or any combination thereof. In some embodiments of any of the aspects, a polypeptide as described herein comprises an NS3 that is resistant to one drug (e.g., protease inhibitor) but responsive to at least one other drug (e.g., protease inhibitor).

In some embodiments of any of the aspects, the drug-resistant NS3 is resistant to telaprevir and sensitive to asunaprevir (e.g., is $NS3^{AI}$) and comprises a NS3 sequence comprising V36M, T54A, and S122G relative to SEQ ID NO: 91. In some embodiments of any of the aspects, the drug-resistant NS3 is resistant to resistant to asunaprevir and sensitive to telaprevir (e.g., is $NS3^{TI}$) and comprises a NS3 sequence comprising F43L, Q80K, S112R, and D168Y relative to SEQ ID NO: 91. Such mutations can be made in other NS3 genotypes/variants to achieve the same drug-resistant characteristics. For further details, see, e.g., Jacobs, C. L., Badiee, R. K. & Lin, M. Z. StaPLs: Versatile genetically encoded modules for engineering drug-inducible proteins. Nat. Methods 15, 523-526 (2018); which is incorporated herein by reference in its entirety.

In embodiments where the drug-controlled peptide docking domain is NS3 or a variant thereof as described herein (e.g., a catalytically inactive or drug-resistant variant), the cognate docking domain-binding peptide can be a peptide that binds NS3 at a location that overlaps with the drug binding site and can be displaced via drug binding to NS3. Cognate docking domain-binding peptides can include nanobodies, scFv, scFab, DARPins, or antibody reagents with the necessary binding properties. Further description of nanobodies can be found, e.g., in Friday et al. Nat Methods 2014 11:1253-60; which is incorporated by reference herein in its entirety. In some embodiments where the drug-controlled peptide docking domain is NS3 or a variant thereof as described herein (e.g., a catalytically inactive or drug-resistant variant), the cognate docking domain-binding peptide can be CP5-46-4D5E; PMED; or $P_{HI}$. In some embodiments where the drug-controlled peptide docking domain is NS3 from HCV genotype 1b or a variant thereof as described herein (e.g., a catalytically inactive or drug-resistant variant), the cognate docking domain-binding peptide can be CP5-46-4D5E; PMED; or $P_{HI}$.

Cognate docking domain-binding peptides for NS3 are known in the art and described, e.g., in Kugler et al. JBC 2012 287:39224-39232; which is incorporated by reference herein in its entirety.

CP5-46-4D5E (also referred to herein as $P_{HI}$) has the sequence of SEQ ID NO: 4.

```
(CP5-46-4D5E)
                                        SEQ ID NO: 4
GELDELVYLLDGPGYDPIHCDVVTRGGSHLFNF
```

CP5-46A-4D5E (also referred to herein as PMED) has the sequence of SEQ ID NO: 5.

```
(PMED)
                                        SEQ ID NO: 5
GELDELVYLLDGPGYDPIHS
```

Nanobodies and other antibody reagents that bind specifically to NS3 are known in the art and include but are not limited to the nanobodies and other antibody reagents provided in Table 5. Further description of suitable antibody reagents can be found, e.g., in the references listed in Table 5; each of which is incorporated by reference herein in its entirety. In some embodiments of any of the aspects, a cognate docking domain-binding peptide that binds NS3 as described herein comprises the CDRs (6 CDRs for an antibody, or 3 CDRs for a nanobody/VHH) of antibody reagent of Table 5 and which maintains the same binding functions with respect to NS3. In some embodiments of any of the aspects, a cognate docking domain-binding peptide that binds NS3 as described herein is an antibody reagent domain of Table 5.

TABLE 5

| Antibody Reagent | Source |
|---|---|
| CM3.B6 scFv | Sullivan et al. Journal of Hepatology 2002 37:660-8 |
| scFv 1, scFv 10, scFv 11, scFv 35, scFv 148, scFv 162, scFv 171, and scFv 53Y | Gal-Tanamy et al. JMB 2005 347:991-1003 and Gal-Tanamy et al. Antiviral Research 2010 88:95-106 |
| scFv #37, scFV #53, scFv #47, scFV #1, scFv #15, scFv #41, scFv #57, and scFv #44 | Zemel et al. Journal of Hepatology 2004 40:1000-1007 |

In embodiments where the drug-controlled peptide docking domain is NS3 or a variant thereof as described herein (e.g., a catalytically inactive or drug-resistant variant), the drug can be selected from Table 2. In embodiments where the drug-controlled peptide docking domain is NS3 or a variant thereof as described herein (e.g., a catalytically inactive or drug-resistant variant), the drug can be grazoprevir, glecaprevir, danoprevir, asunaprevir, telaprevir, boceprevir, simeprevir, paritaprevir, voxilaprevir, narlaprevir, or ciluprevir.

TABLE 2
Exemplary drugs for NS3 drug-controlled peptide docking domains (e.g., NS3/NS4A protease inhibitors)
| Description or Name(s) | Structure |
| --- | --- |
| The N-terminal hexapeptide product of substrate cleavage (e.g., DDIVPC-OH (SEQ ID NO: 192)) | 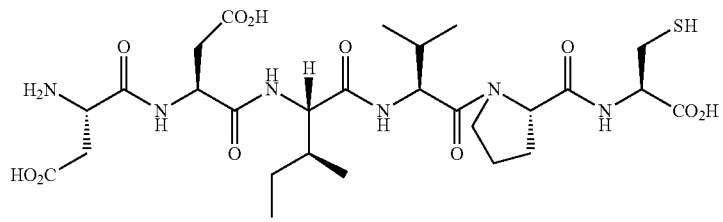 [SMILES: CC[C@H](C)[C@H](NC(=O)[C@H](CC(=O)O)NC(=O)[C@@H](N)CC(=O)O)C(=O)N[C@H](C(=O)N1CCC[C@H]1C(=O)N[C@@H](CS)C(=O)O)C(C)C] |
| One of the products of cleavage of the NS4a-NS4b peptide (e.g., Ac-DEMEEC-OH (SEQ ID NO: 193)) | 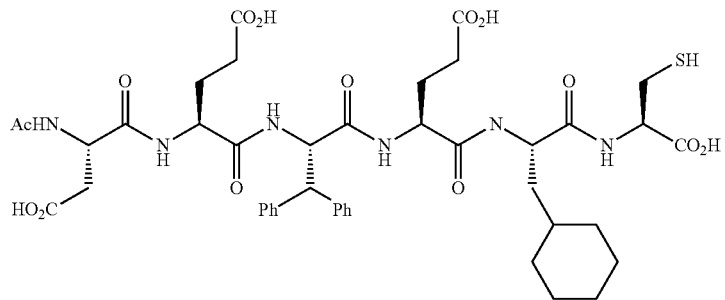 [SMILES: CC(=O)N[C@@H](CC(=O)O)C(=O)N[C@@H](CCC(=O)O)C(=O)N[C@H](C(=O)N[C@@H](CCC(=O)O)C(=O)N[C@@H](CC1CCCCC1)C(=O)N[C@@H](CS)C(=O)O)C(c1ccccc1)c1ccccc1] |
| VICTRELIS ™ boceprevir SCH503034 | 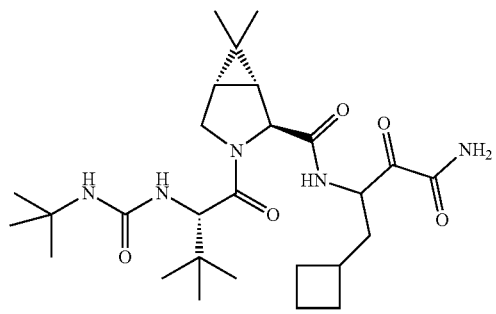 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] |
| INCIVEK ™, INCIVIO ™, telaprevir, VX-950 | 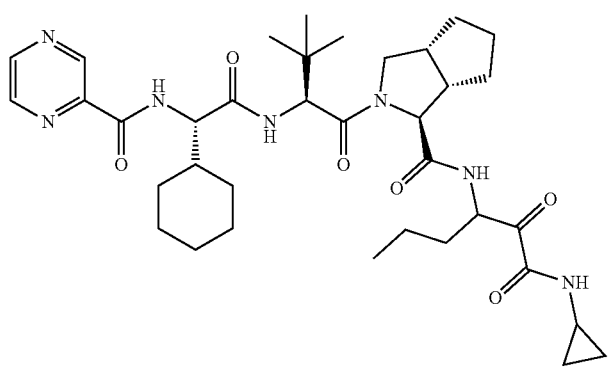 [SMILES: CCCC(NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1] |

TABLE 2-continued
Exemplary drugs for NS3 drug-controlled peptide docking domains (e.g., NS3/NS4A protease inhibitors)
| Description or Name(s) | Structure |
| --- | --- |
Ciluprevir; BILN-2061
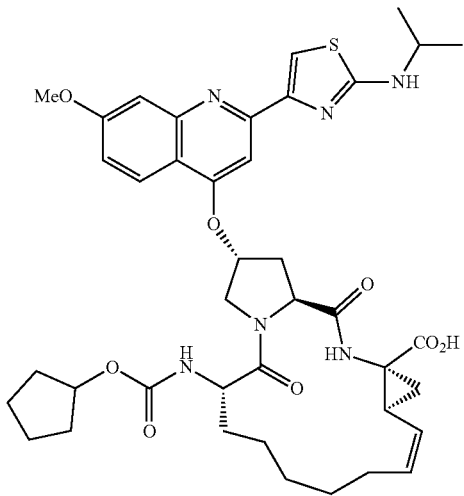 [SMILES: COc1ccc2c(O[C@@H]3C[C@H]4C(=O)N[C@]5(C(=O)O)C[C@H]5/C=C\CCCCC[C@H](NC(=O)OC5CCCC5)C(=O)N4C3)cc(-c3csc(NC(C)C)n3)nc2c1]
BMS-605339
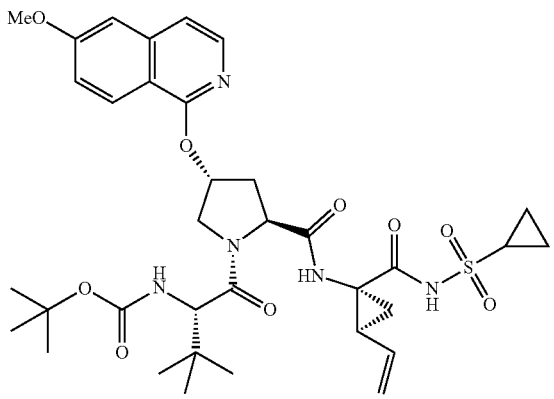
MK-4519
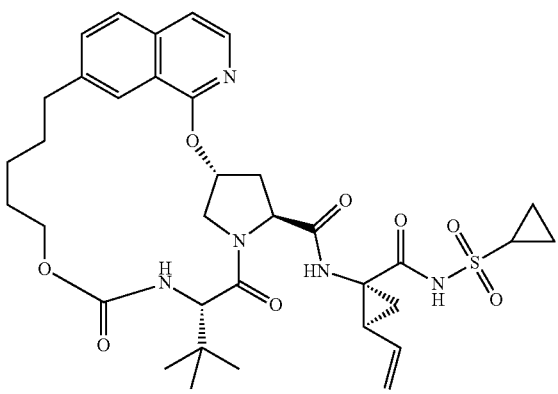 [SMILES: C=C[C@@H]1C[C@]1(NC(=O)[C@@H]1C[C@@H]2CN1C(=O)[C@H](C(C)(C)C)NC(=O)OCCCCCc1ccc3ccnc(c3c1)O2)C(=O)NS(=O)(=O)C1CC1]

TABLE 2-continued
Exemplary drugs for NS3 drug-controlled peptide docking domains (e.g., NS3/NS4A protease inhibitors)
| Description or Name(s) | Structure |
|---|---|
| faldaprevir, BI-201335 | 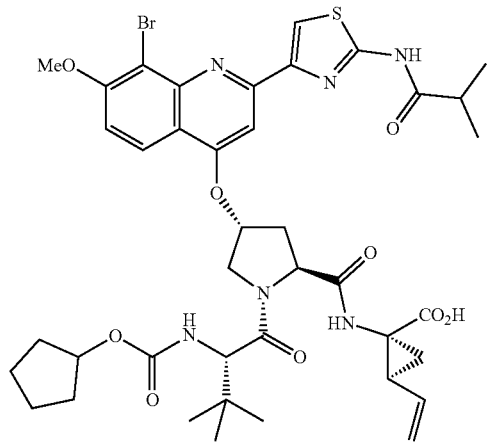 |
| Danoprevir, ITMN-191, R7227 | 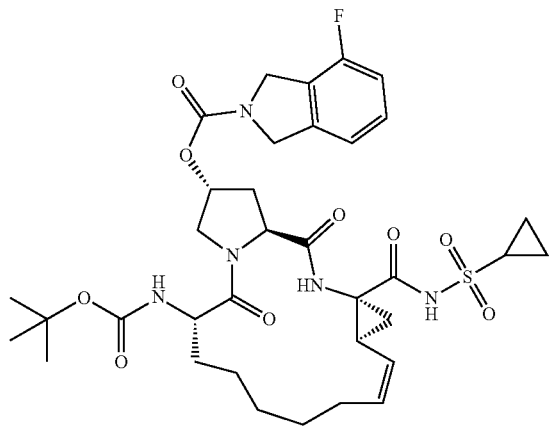 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O] |
| SUNVEPRA™, asunaprevir, BMS-650032 | 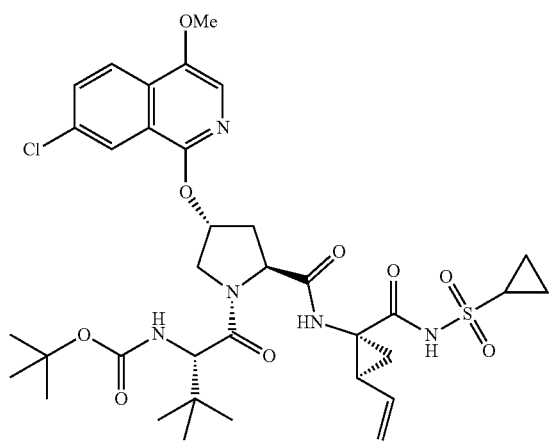 |

TABLE 2-continued

| Exemplary drugs for NS3 drug-controlled peptide docking domains (e.g., NS3/NS4A protease inhibitors) | |
|---|---|
| Description or Name(s) | Structure |
| VANIHEP ™, vaniprevir, MK-7009 | 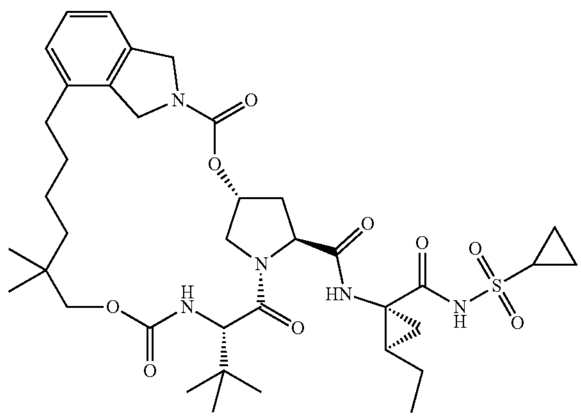  |
| OLYSIO ™, simeprevir, TMC-435350 | 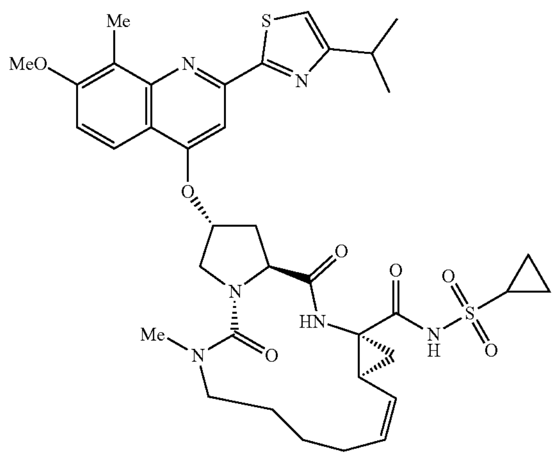  |
| Sovaprevir, ACH-1625 | 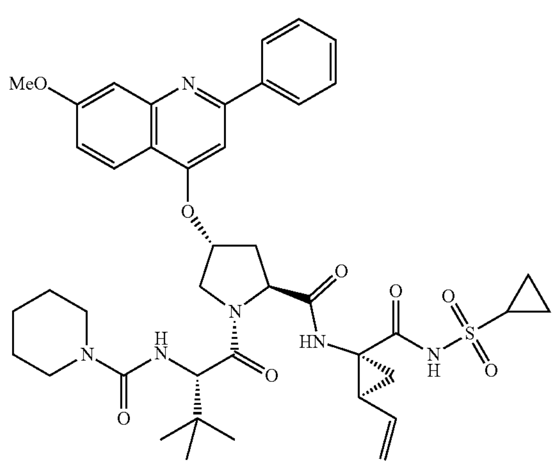  |

TABLE 2-continued

Exemplary drugs for NS3 drug-controlled peptide docking domains (e.g., NS3/NS4A protease inhibitors)

| Description or Name(s) | Structure |
|---|---|
| Deldeprevir/neceprevir, ACH-2684 | 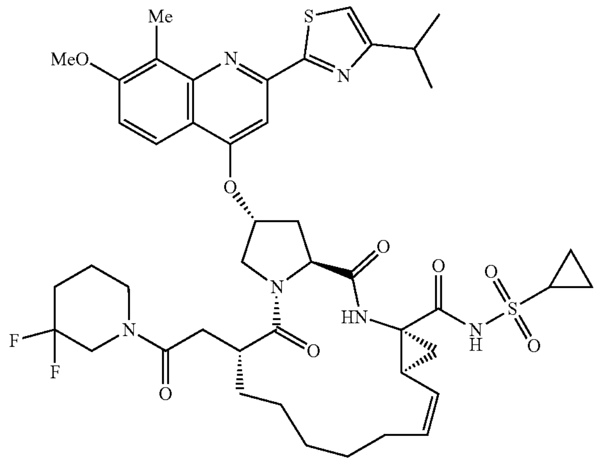 |
| IDX320 | 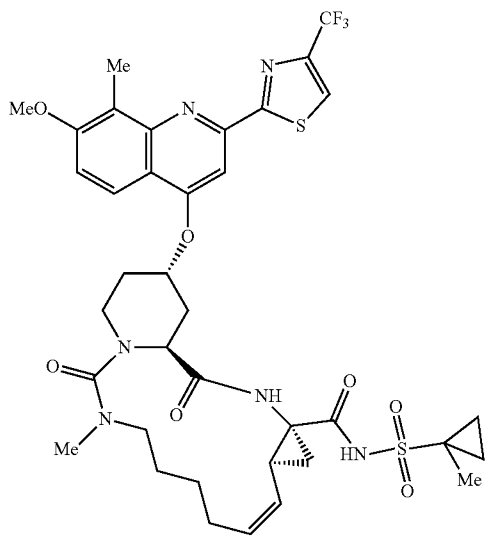 [SMILES: COc1ccc2c(O[C@H]3CCN4C(=O)N(C)CCCC/C=C\[C@@H]5C[C@@]5(C(=O)NS(=O)(=O)C5(C)CC5)NC(=O)[C@@H]4C3)cc(-c3nc(C(F)(F)F)cs3)nc2c1C] |
| GS-9256 | 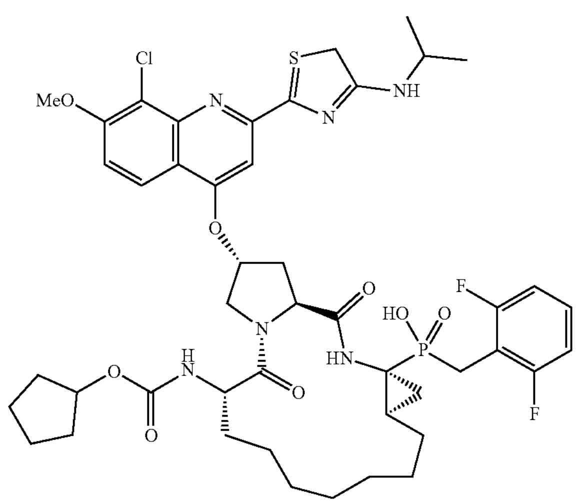 |

US 11,660,288 B2
29 30
TABLE 2-continued
Exemplary drugs for NS3 drug-controlled peptide docking domains (e.g., NS3/NS4A protease inhibitors)
Description or Name(s)   Structure
PHX1766
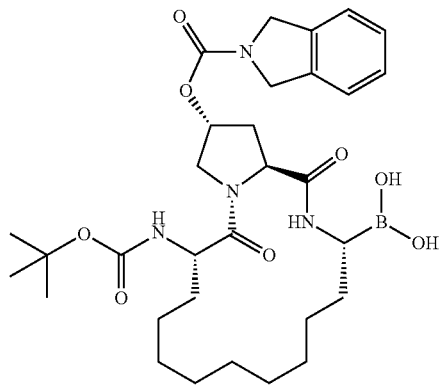
MK-2748
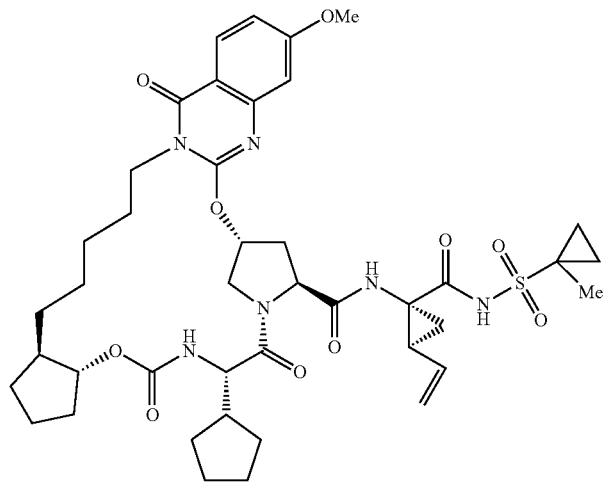
Vedrorevir, GS-9451, GS-9451
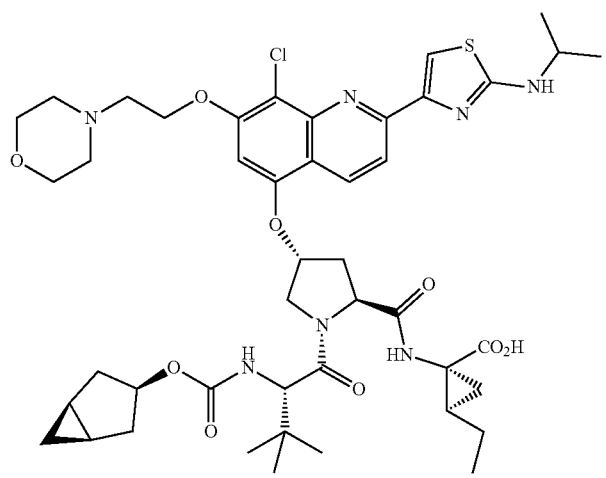

TABLE 2-continued
Exemplary drugs for NS3 drug-controlled peptide docking domains (e.g., NS3/NS4A protease inhibitors)
| Description or Name(s) | Structure |
|---|---|
| MK-6325 | 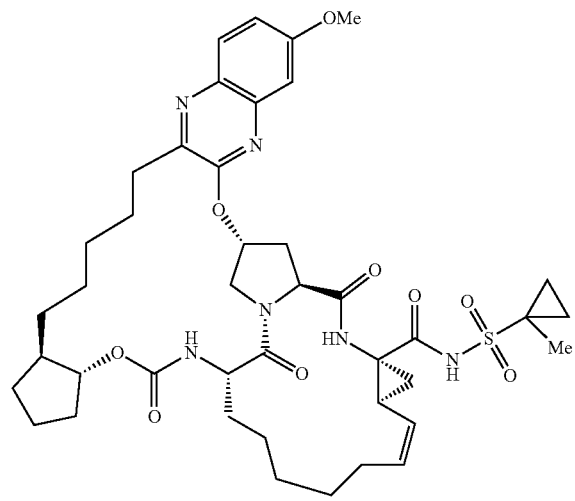 |
| MK-8831 | 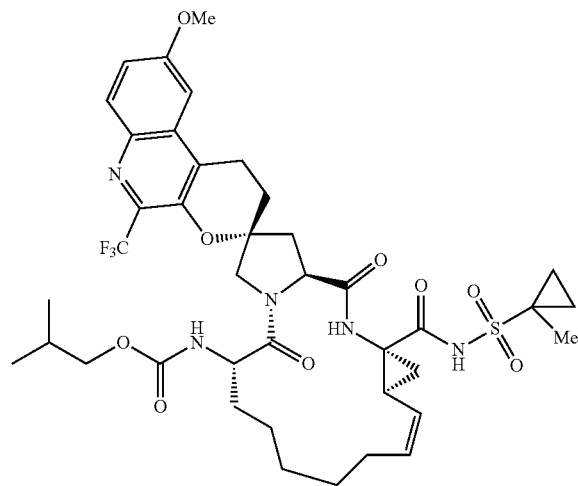 |
| VIKERA PAK ™, paritaprevir, ABT-450 | 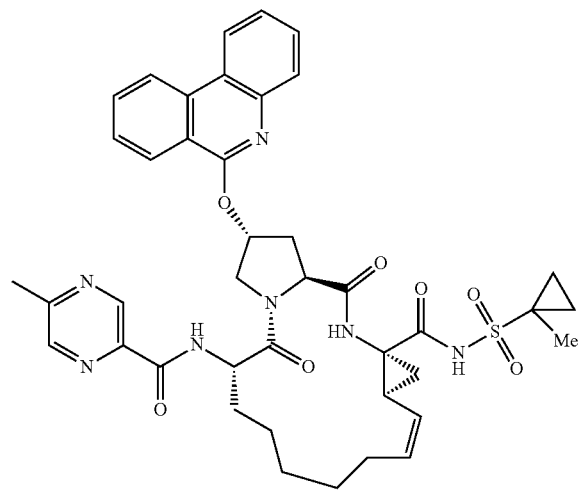 |

TABLE 2-continued

Exemplary drugs for NS3 drug-controlled peptide docking domains (e.g., NS3/NS4A protease inhibitors)

| Description or Name(s) | Structure |
|---|---|
| ZEPATIER ™, grazoprevir, MK-5172 | 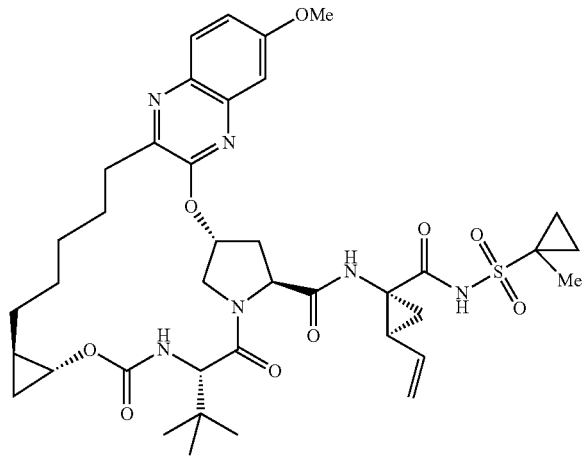 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1(C)CC1] |
| Glecaprevir, ABT-493 | 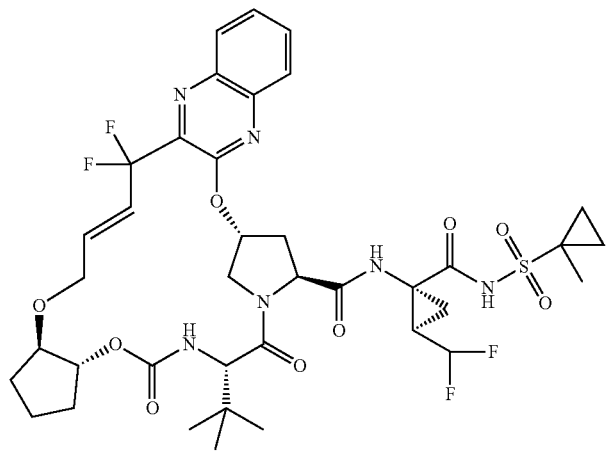 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O] |
| Voxilaprevir, GS-9857 | 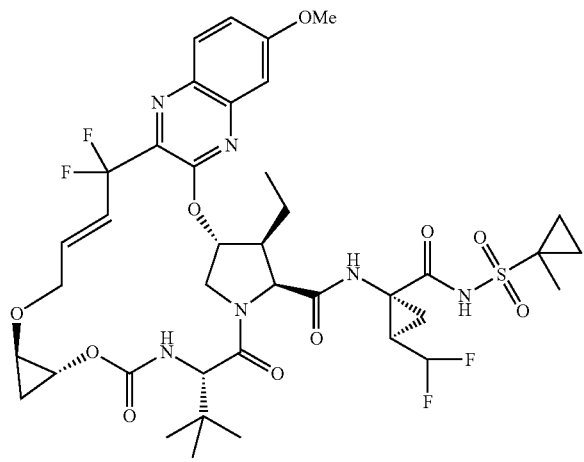 [SMILES: CC[C@@H]1[C@@H]2CN(C(=O)[C@H](C(C)(C)C)NC(=O)O[C@@H]3C[C@H]3OC/C=C/C(F)(F)c3nc4ccc(OC)cc4nc3O2)[C@@H]1C(=O)N[C@]1(C(=O)NS(=O)(=O)C2(C)CC2)C[C@H]1C(F)F] |

In some embodiments of any of the aspects, the drug-controlled peptide docking domain comprises, consists of, or consists essentially of Bcl-xL. As used herein, "Bcl-xL" refers to B-cell lymphoma-extra large protein, which is encoded by the BCL2-like 1 gene (e.g., NCBI Gene ID: 598). Naturally occurring Bcl-xL is found in the membrane of the mitochondria and influences the accessibility of pores in that membrane to pro-apoptotic molecules.

In some embodiments of any of the aspects, Bcl-xL as described herein comprises one of SEQ ID NOs: 1-2 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 1-2 that maintains the same binding functions. In some embodiments of any of the aspects, Bcl-xL as described herein comprises an ortholog of the human SEQ ID NOs: 1-2 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of an ortholog of the human SEQ ID NOs: 1-2 that maintains the same binding functions.

SEQ ID NO: 1, human Bcl-xL 1 msgsnrelvv dflsyklsqk gyswsqfsdv eenrteapeg tesemetpsa ingnpswhla 61 dspavngatg hsssldarev ipmaavkqal reagdefelr yrrafsdlts qlhitpgtay 121 qsfeqvvnel frdgvnwgri vaffsfggal cvesvdkemq vlvsriaawm atylndhlep 181 wigenggwdt fvelygnnaa aesrkgqerf nrwfltgmtv agvvllgslf srk SEQ ID NO: 2, human Bcl-xL 1 msgsnrelvv dflsyklsqk gyswsqfsdv eenrteapeg tesemetpsa ingnpswhla 61 dspavngatg hsssldarev ipmaavkqal reagdefelr yrrafsdlts qlhitpgtay 121 qsfeqdtfve lygnnaaaes rkgqerfnrw fltgmtvagv vllgslfsrk In embodiments where the drug-controlled peptide docking domain is Bcl-xL or a variant thereof as described herein (e.g., a catalytically inactive or drug-resistant variant), the cognate docking domain-binding peptide can be a peptide that binds Bcl-xL at a location that overlaps with the drug binding site and can be displaced via drug binding to Bcl-xL. Cognate docking domain-binding peptides can include nanobodies, scFv, scFab, DARPins, or antibody reagents with the necessary binding properties.

In some embodiments where the drug-controlled peptide docking domain is Bcl-xL or a variant thereof as described herein (e.g., a catalytically inactive or drug-resistant variant), the cognate docking domain-binding peptide can be BAD. As used herein "BAD" refers to BCL2 associated agonist of cell death (e.g., NCBI Gene ID: 572), which binds to Bcl-xL and whose binding is inhibited by the drugs described below. In some embodiments of any of the aspects, BAD as described herein comprises SEQ ID NO: 3 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 3 that maintains the same binding functions. In some embodiments of any of the aspects, Bcl-xL as described herein comprises an ortholog of the human SEQ ID NO: 3 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of an ortholog of the human SEQ ID NO: 3 that maintains the same binding functions. SEQ ID NO: 3, human BAD 1 mfqipefeps eqedsssaer glgpspagdg psgsgkhhrq apgllwdash qqeqptsssh 61 hggagaveir srhssypagt eddegmgeep spfrgrsrsa ppnlwaaqry grelrrmsde 121 fvdsfkkglp rpksagtatq mrqssswtrv fqswwdrnlg rgssapsq In embodiments where the drug-controlled peptide docking domain is Bcl-xL or a variant thereof as described herein (e.g., a catalytically inactive or drug-resistant variant), the drug can be ABT-737, ABT-263 (navitoclax), or GX15-070 (obatoclax).

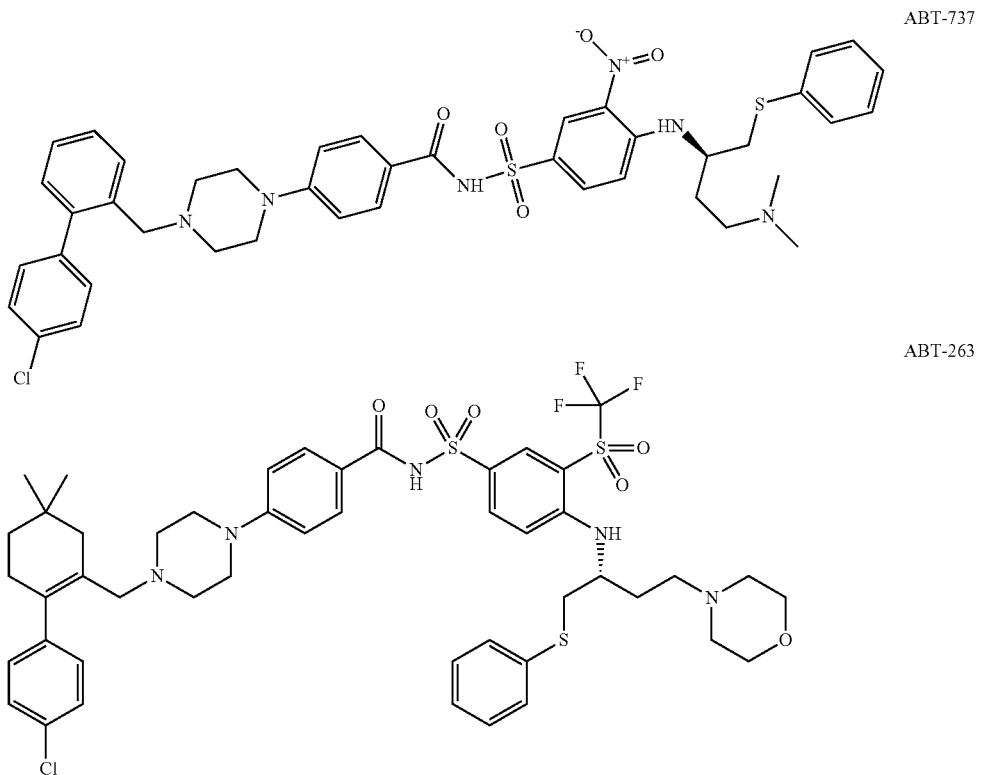

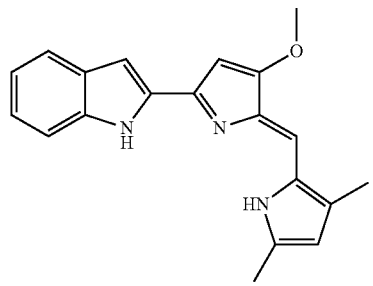

GX15-070

For further details of the Bcl-xL, BAD, and drug interactions, see, e.g., Rooswinkel et al. Cell Death and Disease 2012 3:e366 and Petros et al. Protein Science 2000 12:2528-34; each of which are incorporated herein by reference in their entireties.

In some embodiments of any of the aspects, the drug-controlled peptide docking domain comprises, consists of, or consists essentially of a fluorescent protein (e.g., GFP), the drug is a higher-affinity Fluorescent Protein (e.g., GFP) affinity domain (e.g, an antibody reagent that binds GFP) and the docking domain-binding peptide is a lower-affinity Fluorescent Protein (e.g., GFP) affinity domain (e.g, an antibody reagent that binds GFP).

A variety of fluorescent proteins are known in the art, which are structurally related to the *Aequorea victoria* Green Fluorescent Protein (GFP). The various fluorescent proteins can exhibit improved fluorescence behavior, or fluoresce at different wavelengths to provide a color other than green. Examples of fluorescent proteins include, but are not limited to: GFP, EGFP, sfGFP, blue fluorescent protein (EBFRP, EBFP2, Acurite, mKalama1), Cyan fluoresecent protein (ECFP, Cerulean, CyPet, mTurquoise2), yellow fluorescent protein (YFP, Citrine, Venus, YPet), dsRed, eqFP611, Dronpa, TagRFPs, KFP, EosFP/IrisFP, and Dendra. In some embodiments of any of the aspects, wherein the drug is a fluorescent protein, it is selected from the group consisting of: GFP, EGFP, sfGFP, blue fluorescent protein (EBFRP, EBFP2, Acurite, mKalama1), Cyan fluoresecent protein (ECFP, Cerulean, CyPet, mTurquoise2), and yellow fluorescent protein (YFP, Citrine, Venus, YPet).

Exemplary, but non-limiting examples of fluorescent protein sequences are provided in SEQ ID NOs: 6-12. In some embodiments of any of the aspects, a fluorescent protein as described herein comprises the sequence of one of SEQ ID NOs: 6-12 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 6-12 and which maintains the same binding functions with respect to the fluorescent protein affinity domains.

```
GFP
                                                             SEQ ID NO: 6
    1    mskgeelftg vvpilveldg dvnghkfsvs gegegdatyg kltlkfictt gklpvpwptl 61    vttfaygvqc fsrypdhmkr hdffksampe gyvqertiff kddgnyktra evkfegdtlv 121    nrielkgidf kedgnilghk leynynshnv yimadkqkng ikvnfkirhn iedgsvqlad 181    hyqqntpigd gpvllpdnhy istqsvlskd pnekrdhmvl lefvtaagit hgmdelyk dsRed
                                                             SEQ ID NO: 7
    1    massedvike fmrfkvrmeg svnghefeie gegegrpyeg tqtaklkvtk ggplpfawdi 61    lspqfqygsk vyvkhpadip dykklsfpeg fkwervmnfe dggvvtvtqd sslqdgsfiy 121    kvkfigvnfp sdgpvmqkkt mgweasterl yprdgvlkge ihkalklkdg ghylvefksi 181    ymakkpvqlp gyyyvdskid itshnedyti veqyeraegr hhlfl eGFP
                                                             SEQ ID NO: 8
    1    msrvskgeel ftgvvpilve ldgdvnghkf svsgegegda tygkltlkfi cttgklpvpw 61    ptlvttltyg vqcfsrypdh mkqhdffksa mpegyvqert iffkddgnyk traevkfegd 121    tlvnrielkg idfkedgnil ghkleynyns hnvyimadkq kngikvnfki rhniedgsvq 181    ladhyqqntp igdgpvllpd nhylstqsal skdpnekrdh mvllefvtaa gitlgmdely 241    k
```

-continued

CyPET

SEQ ID NO: 9

```
  1  mktnlflfli fslllslssa efgavskgee lfggivpilv elegdvnghk fsvsgegegd
 61  atygkltlkf icttgklpvp wptlvttltw gvqcfsrypd hmkqhdffks vmpegyvqer
121  tiffkddgny ktraevkfeg dtlvnrielk gidfkedgni lghkleynyi shnvyitadk
181  qkngikanfk arhnitdgsv qladhyqqnt pigdgpvilp dnhylstqsa lskdpnekrd
241  hmvllefvta agithgmdel ykhdel
```

Cerulean

SEQ ID NO: 10

```
  1  mvskgeelft gvvpilveld gdvnghkfsv sgegegdaty gkltlkfict tgklpvpwpt
 61  lvttltwgvq cfarypdhmk qhdffksamp egyvqertif fkddgnyktr aevkfegdtl
121  vnrielkgid fkedgnilgh kleynaisdn vyitadkqkn gikanfkirh niedgsvqla
181  dhyqqntpig dgpvllpdnh ylstqsklsk dpnekrdhmv llefvtaagi tlgmdelyk
```

YFP

SEQ ID NO: 11

```
  1  mvskgeelft gvvpilveld gdvnghkfsv sgegegdaty gkltlkfict tgklpvpwpt
 61  lvttfgyglq cfarypdhmk lhdffksamp egyvqertif fkddgnyktr aevkfegdtl
121  vnrielkgid fkedgnilgh kleynynshn vyimadkqkn gikvnfkirh niedgsvqla
181  dhyqqntpig dgpvllpdnh ylsyqsalsk dpnekrdhmv llefvtaagi tlgmdelyk
```

Venus

SEQ ID NO: 12

```
  1  vskgeelftg vvpilveldg dvnghkfsvs gegegdatyg kltlklictt gklpvpwptl
 61  vttlgyglqc farypdhmkq hdffksampe gyvqertiff kddgnyktra evkfegdtlv
121  nrielkgidf kedgnilghk leynynshnv yitadkqkng ikanfkirhn iedggvqlad
181  hyqqntpigd gpvllpdnhy lsyqsalskd pnekrdhmvl lefvtaagit lgmdelyk
```

As used herein, "fluorescent protein affinity domain" refers to a domain that binds to a fluorescent protein. In the molecule sets described herein, a higher-affinity and a lower-affinity domain are utilized. The "higher" and "lower" refers to the affinity for the fluorescent protein relative to the other affinity domain in the molecule set. "Higher" and "lower" in this respect do not refer absolute levels of affinity, but relative values within the molecule set. An affinity domain can be, e.g, an antibody reagent, antibody, nanobody, aptamer, DARPin or the like. Affinity domains (and their affinities) for fluorescent proteins are known in the art and include but are not limited to the affinity domains provided in Table 4. Further description of suitable affinity domains can be found, e.g., in Friday et al. Nat Methods 2014 11:1253-60; Zhang et al. Scientific Reports 2020 10:6239; Kubala et al. Protein Science 2010 19:2389-2401; and Twair et al. Mol Biol Rep 2014 41:6887-6898; each of which is incorporated by reference herein in its entirety. Each of the individual affinity domains provided in Table 4 can be a higher-affinity or a lower-affinity domain, depending on which other affinity domain it is paired with within a given molecule set.

TABLE 4

| Affinity Domain | Source | Affinity for fluorescent protein |
|---|---|---|
| EPR14104 | Abcam Cat. No. ab183734 | KD with GFP = 1.11 × 10$^{-11}$ M (Does not cross-react with RFP or BFP) |
| E85 | Abcam Cat. No. ab32146 | $K_D$ with GFP = 1.02 × 10$^{-12}$ M (Does not cross-react with RFP or BFP) |

TABLE 4-continued

| Affinity Domain | Source | Affinity for fluorescent protein |
|---|---|---|
| ChromoTek GFP VHH | Chromotek Cat. No. gt | $K_D$ with GFP = 1 pM (Cross-reacts with CFP, eGFP, wtGFP, GFP S65T, AcGFP, TagGFP, tagGFP2, sfGFP, pHluorin, eYFP, YFP, Venus, Citrine) |
| LaG16 | Zhang et al. Scientific Reports 2020 10:6239 | $K_D$ with GFP = 0.5 nM |

In some embodiments of any of the aspects, a fluorescent protein affinity domain as described herein comprises the CDRs (6 CDRs for an antibody, or 3 CDRs for a nanobody/VHH) of an affinity domain of Table 4 and which maintains the same binding functions with respect to the fluorescent protein affinity domains. In some embodiments of any of the aspects, a fluorescent protein affinity domain as described herein is an affinity domain of Table 4.

Figure 3A:
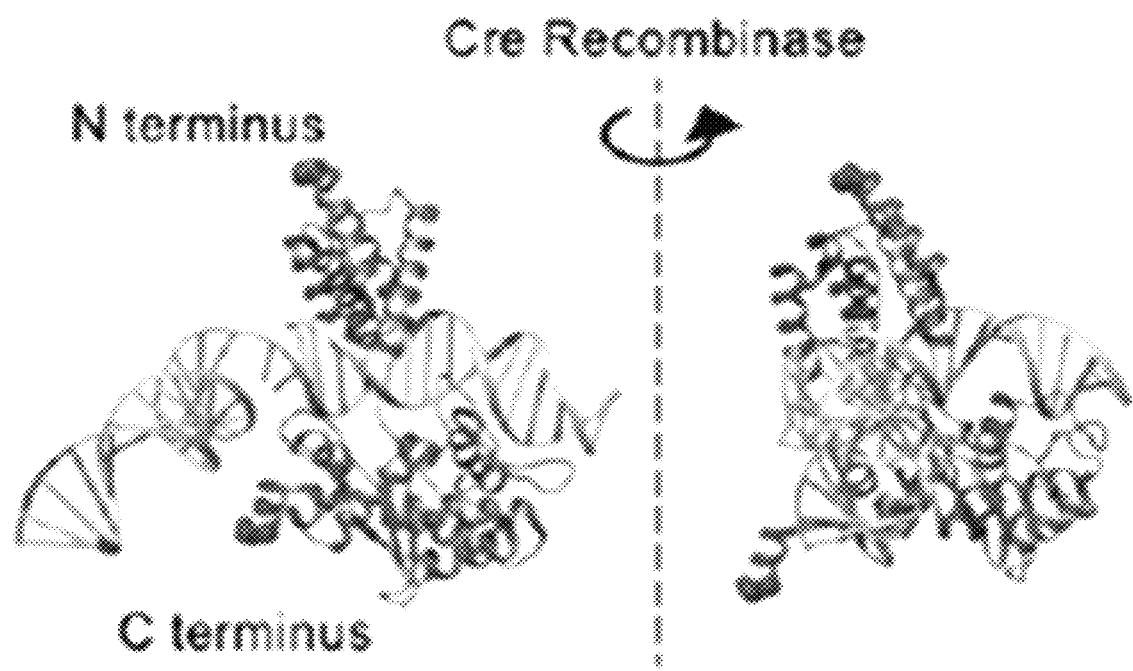
FIGS. 3A-3F depict antiviral drug control of genetic recombination in eukaryotes (FIG. 3A) Structure of Cre recombinase bound to DNA (PDB 1ma7[28]). N-terminal and C-terminal residues labeled in red and blue respectively.

In a first application of the molecule sets described herein, the molecule sets can be used to control the activity of a recombinase. By providing a cognate pair of a drug-controlled peptide docking domain and a docking domain-binding peptide in the same polypeptide molecule as a recombinase, the cognate pair of a drug-controlled peptide docking domain and a docking domain-binding peptide will bind to each other, causing physical or steric constraints on the ability of the recombinase to interact with its targets and to catalyze recombination. The addition of the drug of the molecule set will disrupt the binding of the cognate pair of a drug-controlled peptide docking domain and a docking domain-binding peptide and induce the activity of the recombinase. Importantly, prior attempts at intramolecular control of recombinases (and druggable variants of such control) was extremely leaky. The inventors have discovered that if a recombinase variant with decreased cooperativity is used, then the control over the recombinase becomes very tight and does not demonstrate any leakiness (see, e.g., FIG. 3E herein). Given the dramatic nature of a recombinase's action, such tight control is necessary and leaky systems lack any practical utility. Accordingly, in one aspect of any of the embodiments, described herein is a polypeptide comprising: a) a drug-controlled peptide docking domain; b) a cognate docking domain-binding peptide; and c) a recombinase comprising at least one decreased cooperativity mutation. In one aspect of any of the embodiments, described herein is a i) polypeptide comprising: a) a drug-controlled peptide docking domain; b) a cognate docking domain-binding peptide; and c) a recombinase comprising at least one decreased cooperativity mutation; and ii) a drug that controls the drug-controlled peptide docking domain.

Recombinases, herein, also referred to as "site-specific recombinases" (or "SSR") have been engineered to be very active in a wide range of organisms, including bacteria, mammals, insects, plants and fish. Cre, Flp and PhiC, in particular, have been used widely in animal model development, with Cre being widely used in generation of animal models. However, tight control or regulation of recombinase activity is necessary to avoid toxicity. Recombinases are frequently used to impart stable, DNA-base memory to the logic and memory systems in genetic logic circuits. A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. A "genetic element," as used herein, refers to a sequence of DNA that has a role in gene expression. For example, a promoter, a transcriptional terminator, and a nucleic acid encoding a product (e.g., a protein product) is each considered to be a genetic element.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases include, without limitation, β-six, CinH, ParA and γδ; and examples of unidirectional serine recombinases include, without limitation, Bxb1, φC31 (phiC31), TP901, TG1, φBT1, R4, φRV1, φFC1, MRU, A118, U153 and gp29. Examples of bidirectional tyrosine recombinases include, without limitation, Cre, FLP, and R; and unidirectional tyrosine recombinases include, without limitation, Lambda, HK101, HK022 and pSAM2. The serine and tyrosine recombinase names stem from the conserved nucleophilic amino acid residue that the recombinase uses to attack the DNA and which becomes covalently linked to the DNA during strand exchange. Recombinases have been used for numerous standard biological applications, including the creation of gene knockouts and the solving of sorting problems.

Exemplary recombinases for use in the methods and compositions as described herein, and which can be split into two or more protein fragments according to the technology as disclosed herein, include, but are not limited to, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, BxB1, A118, spoIVCA, PhiMR11, SCCmec, TndX, XerC, XerD, XisA, Hin, Cin, mrpA, beta, PhiFC1, Fre, Clp, sTre, FimE, and HbiF.

In some embodiments of any of the aspects, the recombinase is a tyrosine recombinase. In some embodiments of any of the aspects, the recombinase is Cre, VCre, SCre, Flippase (Flp) XerA, XerC, or XerD.

In some embodiments of any of the aspects, the recombinase can be VCre or SCre. These recombinases and their sequences are known in the art, e.g., VCre's amino acid sequence is available in Genbank as ABX77110.1 and SCre's amino acid sequence is available in Genbank as ABK50591.1. Further discussion of VCre and SCre can be found, e.g., in Suzuki. Nucleic Acids Res 2011 39:e49; which is incorporated by reference herein in its entirety.

Further suitable recombinases are known in the art and include Flippase (Flp), XerA, XerC, and XerD. These recombinases and their sequences are known in the art, e.g., XerA's amino acid sequence is available in Genbank under Gene ID: 947861, XerC's amino acid sequence is available in Genbank under Gene ID: 948355, and XerD's amino acid sequence is available in Genbank under Gene ID: 947362.

The outcome of the recombination reaction mediated by a recombinase depends, in part, on the location and orientation of two short repeated DNA sequences (e.g., RRS) that are to be recombined, typically less than 30 bp long. Recombinases bind to these repeated sequences, which are specific to each recombinase, and are herein referred to as "recombinase recognition sequences" or "recombinase recognition sites" or "RRS". Thus, as used herein, a recombinase is "specific for" a recombinase recognition site when the recombinase can mediate inversion or excision between the repeat DNA sequences. As used herein, a recombinase may also be said to recognize its "cognate recombinase recognition sites," which flank an intervening genetic element (e.g., promoter, terminator, or target gene). A genetic element is said to be "flanked" by recombinase recognition sites when the element is located between and immediately adjacent to two repeated DNA sequences. In some embodiments, the recombinase recognition sites do not overlap each other. However, in other embodiments, recombinase recognition sites do overlap each other, such as described herein below, which permits greatly increased combinatorial complexity.

Exemplary RRS include, but are not limited to, loxP, loxN, lox 511, lox 5171, lox 2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.

In some embodiments, a recombinase can result in an inversion reaction. Inversion recombination happens between two short, inverted, repeated DNA sequences. Without wishing to be bound by theory, a DNA loop formation, assisted by DNA bending proteins, brings the two repeat sequences together, at which point DNA cleavage and ligation occur. This reaction is ATP-independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA.

In some embodiments, a recombinase can result in an excision reaction. Conversely, excision (integration) recombination occurs between two short, repeated DNA sequences that are oriented in the same direction. In this case, the intervening DNA is excised/removed. For example, an AND gate can be assembled by placing a terminator between each of two different sets of recombinase sites oriented for excision, flanked by a promoter and an output, such as a GFP-encoding sequence. In this example, both terminators must be excised by input-dependent action of the recombinase(s) to permit read through from the promoter to the GFP-encoding sequence. Thus two inputs are needed to excise both terminators to generate output.

In some embodiments, a recombinase can be an irreversible or reversible recombinase. As used herein, an "irreversible recombinase" refers to a recombinase that can catalyze recombination between two complementary recombination sites, but cannot catalyze recombination between the hybrid sites that are formed by this recombination without the assistance of an additional factor. Irreversible recombinases, and nucleic acids that encode the irreversible recombinases, are described in the art and can be obtained using routine methods. Examples of irreversible recombinases include, without limitation, phiC31 (φC31) recombinase, coliphage P4 recombinase, coliphage lambda integrase, *Listeria* A118 phage recombinase, and actinophage R4 Sre recombinase, HK101, HK022, pSAM2, Bxb1, TP901, TG1, φBTI, cpRV1, cpFC1, MRU, U153 and gp29. In some embodiments, the recombinase is the phiC31 (φC31) integrase.

Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

In some embodiments, a recombinase is a serine recombinase. Thus, in some embodiments, the recombinase is considered to be irreversible. For some serine recombinases, an initial recombination event can be reversed when a recombinase directionality factor (RDF) is present. RDFs are a diverse group of proteins involved in controlling the directionality of integrase-mediated site-specific recombination reactions. Typically, RDFs are small DNA-binding proteins acting as accessory factors to influence the choice of substrates that are recombined by their cognate recombinase. See Lewis and Hatfull, Nucleic Acids Res. 2001 Jun. 1; 29(11): 2205-2216. For example, when the recombination sites, attB and attP are placed in the antiparallel orientation, the presence of recombinases can stably invert the DNA sequence between the two sites and generate an attL and attR site ("BP reaction"). This inversion remains stable unless a RDF is also expressed along with bxb1 or phiC, which can invert the sequence between attL and attR and regenerate attB and attP site ("LR reaction"). Examples of RDF include, but are not limited to, gp47 for bxb1, gp3 for phiC31, gp3 for PhiBT1, ORF7 for TP901-1, gp25 for TG1, and gp3 for PhiRv1.

In some embodiments, a recombinase is a tyrosine recombinase. Thus, in some embodiments, the recombinase is considered to be reversible.

In some embodiments, a recombinase is Cre and the corresponding recombinase recognition sequences comprise loxP. In some embodiments, a recombinase is Flp and the corresponding recombinase recognition sequences comprise FRT. In some embodiments, a recombinase is VCre and the corresponding recombinase recognition sequences comprise VloxP. In some embodiments, a recombinase is SCre and the corresponding recombinase recognition sequences comprise SloxM1.

In some embodiments, the recombinase is a Cre recombinase. In some embodiments, the recombinase comprises, consists of, or consists essentially of the Cre protein of SEQ ID NO: 58. In the avoidance of any doubt, SEQ ID NO: 58 is as follows:

(SEQ ID NO: 58)
MSNLLTVHQNLPALPVDATSDEVRKNLMDMFRDRQAFSEHTWKMLLSVC

RSWAAWCKLNNRKWFPAEPEDVRDYLLYLQARGLAVKTIQQHLGQLNML

HRRSGLPRPSDSNAVSLVMRRIRKENVDAGERAKQALAFERTDFDQVRS

LMENSDRCQDIRNLAFLGIAYNTLLRIAEIARIRVKDISRTDGGRMLIH

IGRTKTLVSTAGVEKALSLGVTKLVERWISVSGVADDPNNYLFCRVRKN

GVAAPSATSQLSTRALEGIFEATHRLIYGAKDDSGQRYLAWSGHSARVG

AARDMARAGVSIPEIMQAGGWTNVNIVMNYIRNLDSETGAMVRLLEDGD

In some embodiments, the recombinase comprises, consists of, or consists essentially of an amino acid sequence that is at least 75%, or at least 80%, or at least 85%, or at least 90% or at least 95%, or at least about 97%, or at least about 98%, or at least about 99% identical to SEQ ID NO: 58, where when the recombinase retains the recombinase activity of SEQ ID NO: 58, e.g., site-specific recombination of a nucleic acid sequence between two such loxP sites. Accordingly, in some embodiments, a recombinase as disclosed herein is Cre, and can recognize RRS comprising LoxP. A LoxP sequence can comprise nucleic acids ATAACTTCGTATAnnntannnTATACGAAGTTAT (SEQ ID NO: 59).

In some embodiments, the recombinase is a Flp or FlpO recombinase. In some embodiments, the recombinase comprises, consists of, or consists essentially of SEQ ID NO: 60. In the avoidance of any doubt, SEQ ID NO: 60 is as follows:

(SEQ ID NO: 60)
MSQFDILCKTPPKVLVRQFVERFERPSGEKIASCAAELTYLCWMITHNG

TAIKRATFMSYNTIISNSLSFDIVNKSLQFKYKTQKATILEASLKKLIP

AWEFTIIPYNGQKHQSDITDIVSSLQLQFESSEEADKGNSHSKKMLKAL

LSEGESIWEITEKILNSFEYTSRFTKTKTLYQFLFLATFINCGRFSDIK

NVDPKSFKLVQNKYLGVIIQCLVTETKTSVSRHIYFFSARGRIDPLVYL

DEFLRNSEPVLKRVNRTGNSSSNKQEYQLLKDNLVRSYNKALKKNAPYP

IFAIKNGPKSHIGRHLMTSFLSMKGLTELTNVVGNWSDKRASAVARTTY

THQITAIPDHYFALVSRYYAYDPISKEMIALKDETNPIEEWQHIEQLKG

SAEGSIRYPAWNGIISQEVLDYLSSYINRRI

In some embodiments, the recombinase comprises, consists of, or consists essentially of an amino acid sequence that is at least 75%, or at least 80%, or at least 85%, or at least 90% or at least 95%, or at least about 97%, or at least about 98%, or at least about 99% identical to SEQ ID NO: 60, and retains the recombinase activity of SEQ ID NO: 60, e.g, can recognize flippase recognition target (FRT) sites, and result in site-specific recombination of a nucleic acid sequence between two such FRT sites. Accordingly, in some embodiments, a recombinase is Flp, and can recognize recombinase recognition sequences comprise FRT. A FRT sequence can comprise nucleic acids (SEQ ID NO: 61)
GAAGTTCCTATTCTCTAGAAAGTATAGGAACTTC In some embodiments, the recombinase is a VCre recombinase. In some embodiments, the recombinase comprises, consists of, or consists essentially of the VCre protein of SEQ ID NO: 65. In the avoidance of any doubt, SEQ ID NO: 65 is as follows:

(SEQ ID NO: 65)
MIENQLSLLGDFSGVRPDDVKTAIQAAQKKGINVAENEQFKAAFEHLLN

EFKKREERYSPNTLRRLESAWTCFVDWCLANHRHSLPATPDTVEAFFIE

RAEELHRNTLSVYRWAISRVHRVAGCPDPCLDIYVEDRLKAIARKKVRE

GEAVKQASPFNEQHLLKLTSLWYRSDKLLLRRNLALLAVAYESMLRASE

LANIRVSDMELAGDGTAILTIPITKTNHSGEPDTCILSQDVVSLLMDYT

EAGKLDMSSDGFLFVGVSKHNTCIKPKKDKQTGEVLHKPITTKTVEGVF

YSAWETLDLGRQGVKPFTAHSARVGAAQDLLKKGYNTLQIQQSGRWSSG

AMVARYGRAILARDGAMAHSRVKTRSAPMQWGKDEKD

In some embodiments, the recombinase protein comprises, consists of, or consists essentially of an amino acid sequence that is at least 75%, or at least 80%, or at least 85%, or at least 90% or at least 95%, or at least about 97%, or at least about 98%, or at least about 99% identical to SEQ ID NO: 65, and retains the activity of SEQ ID NO: 65, e.g., recognizes the VloxP recombinase recognition sequences and results in site-specific recombination of a nucleic acid sequence between two such VloxP sites. Accordingly, in some embodiments, the recombinase is VCre, and can recognize RRS comprising VLoxP. A VLoxP sequence can comprise nucleic acids (SEQ ID NO: 66)
TCAATTTCTGAGAactgtcatTCTCGGAAATTGA Recombinase activity often involves the formation of multimeric recombinase protein assemblies, e.g., such as for Cre. Such assemblies can be, e.g., dimers or tetramers. The ability to multimerize and exert recombinase activity as an assembly is referred to as "cooperativity." In some embodiments of any of the aspects, the recombinase has a decreased cooperativity mutation. Such decreased cooperativity mutations are known in the art.

Figure 18:
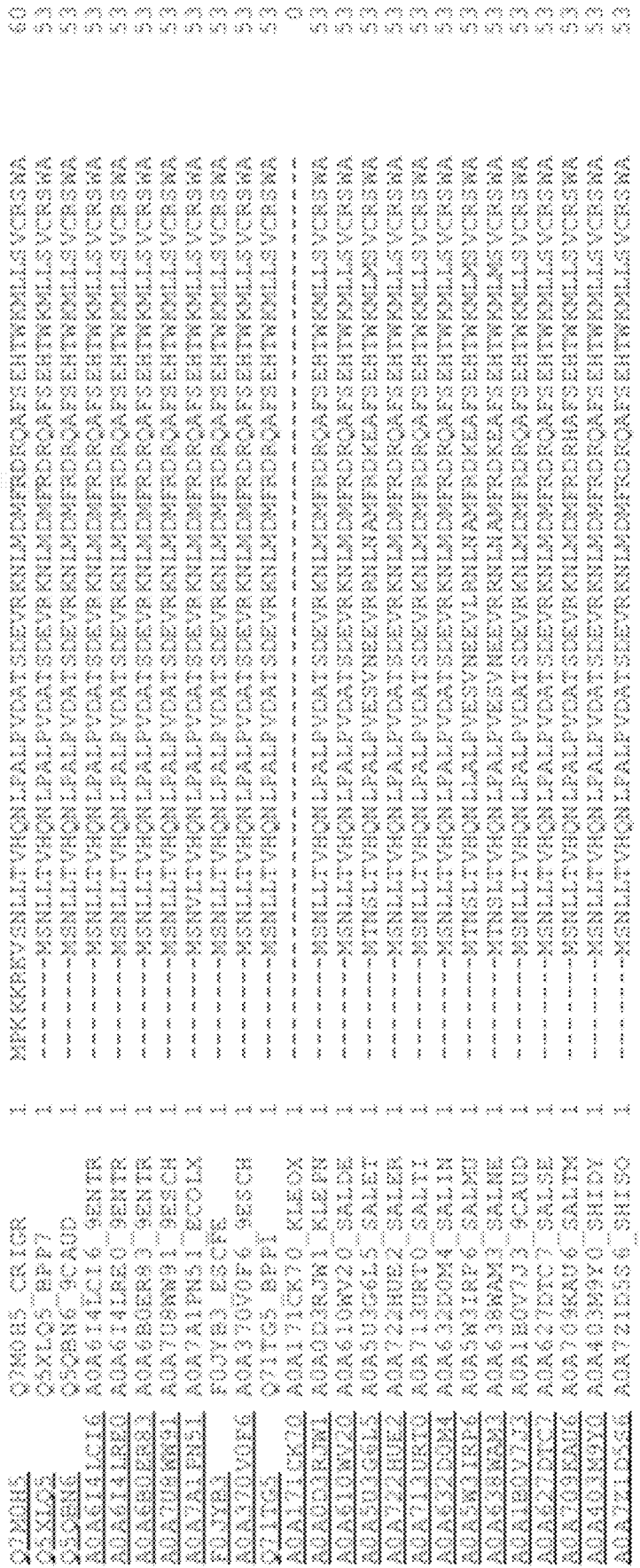
FIG. 18 depicts the alignment of 20 recombinases with R32 of SEQ ID NO: 58 highlighted in the first row, demonstrating that this catalytic residue is highly conserved across recombinases and readily identified in a recombinase by alignment with Cre.

For example, it is known that for Cre, residues 32, 69, 303, 304, and 305 of SEQ ID NO: 58 are critical for cooperativity. Accordingly, in some embodiments of any of the aspects, a decreased cooperativity mutation can be a mutation at a residue corresponding to one or more of residues 32, 69, 303, 304, and 305 of SEQ ID NO: 58). Residues corresponding to one or more of residues 32, 69, 303, 304, and 305 of SEQ ID NO: 58 can be readily identified by one of skill in the art in other recombinase sequences by alignment of SEQ ID NO: 58 and the sequence of a different recombinase. For example, FIG. 18 demonstrates that R32 of SEQ ID NO: 58 is highly conserved across a selection of 20 recombinases.

In some embodiments of any of the aspects, a decreased cooperativity mutation can be a mutation at a residue corresponding to residue 32 of SEQ ID NO: 58. In some embodiments of any of the aspects, a decreased cooperativity mutation can be a mutation at a residue corresponding to residue 69 of SEQ ID NO: 58. In some embodiments of any of the aspects, a decreased cooperativity mutation can be a mutation at a residue corresponding to residue 32 of SEQ ID NO: 58 and a residue corresponding to residue 69 of SEQ ID NO: 58.

In some embodiments of any of the aspects, decreased cooperativity mutation can prevent or eliminate the formation of an intramolecular salt bridge between recombinase monomers via side chains at positions corresponding to 32 and 69 of SEQ ID NO: 58.

In some embodiments of any of the aspects, the decreased cooperativity mutation is a mutation to a residue that does not have a positive charge. In some embodiments of any of the aspects, the decreased cooperativity mutation is a mutation to a naturally occurring residue that does not have a positive charge. In some embodiments of any of the aspects, the decreased cooperativity mutation is a mutation to a hydrophobic residue. In some embodiments of any of the aspects, the decreased cooperativity mutation is a mutation to a naturally occurring hydrophobic residue. In some embodiments of any of the aspects, the decreased cooperativity mutation is a mutation to valine, methionine, leucine, isoleucine, or alanine residue. In some embodiments of any of the aspects, the decreased cooperativity mutation is a mutation to valine or methionine residue.

In some embodiments of any of the aspects, a decreased cooperativity mutation can be a mutation of a residue corresponding to one or more of residues 32, 69, 303, 304, and 305 of SEQ ID NO: 58, to a residue that does not have a positive charge. In some embodiments of any of the aspects, a decreased cooperativity mutation can be a mutation of a residue corresponding to one or more of residues 32, 69, 303, 304, and 305 of SEQ ID NO: 58, to a naturally occurring residue that does not have a positive charge. In some embodiments of any of the aspects, a decreased cooperativity mutation can be a mutation of a residue corresponding to one or more of residues 32, 69, 303, 304, and 305 of SEQ ID NO: 58, to a hydrophobic residue. In some embodiments of any of the aspects, a decreased cooperativity mutation can be a mutation of a residue corresponding to one or more of residues 32, 69, 303, 304, and 305 of SEQ ID NO: 58, to a naturally occurring hydrophobic residue. In some embodiments of any of the aspects, a decreased cooperativity mutation can be a mutation of a residue corresponding to one or more of residues 32, 69, 303, 304, and 305 of SEQ ID NO: 58, to a valine, methionine, leucine, isoleucine, or alanine residue. In some embodiments of any of the aspects, a decreased cooperativity mutation can be a mutation of a residue corresponding to one or more of residues 32, 69, 303, 304, and 305 of SEQ ID NO: 58, to a valine or methionine residue.

In some embodiments of any of the aspects, a decreased cooperativity mutation can be a mutation of a residue corresponding to residue 32 of SEQ ID NO: 58, to a residue that does not have a positive charge. In some embodiments of any of the aspects, a decreased cooperativity mutation can be a mutation of a residue corresponding to residue 32 of SEQ ID NO: 58, to a naturally occurring residue that does not have a positive charge. In some embodiments of any of the aspects, a decreased cooperativity mutation can be a mutation of a residue corresponding to residue 32 of SEQ ID NO: 58, to a hydrophobic residue. In some embodiments of any of the aspects, a decreased cooperativity mutation can be a mutation of a residue corresponding to residue 32 of SEQ ID NO: 58, to a naturally occurring hydrophobic residue. In some embodiments of any of the aspects, a decreased cooperativity mutation can be a mutation of a residue corresponding to residue 32 of SEQ ID NO: 58, to a valine, methionine, leucine, isoleucine, or alanine residue. In some embodiments of any of the aspects, a decreased cooperativity mutation can be a mutation of a residue corresponding to residue 32 of SEQ ID NO: 58, to a valine or methionine residue.

In some embodiments of any of the aspects, a decreased cooperativity mutation can be a mutation of a residue corresponding to residue 69 of SEQ ID NO: 58, to a residue that does not have a positive charge. In some embodiments of any of the aspects, a decreased cooperativity mutation can be a mutation of a residue corresponding to residue 69 of SEQ ID NO: 58, to a naturally occurring residue that does not have a positive charge. In some embodiments of any of the aspects, a decreased cooperativity mutation can be a mutation of a residue corresponding to residue 69 of SEQ ID NO: 58, to a hydrophobic residue. In some embodiments of any of the aspects, a decreased cooperativity mutation can be a mutation of a residue corresponding to residue 69 of SEQ ID NO: 58, to a naturally occurring hydrophobic residue. In some embodiments of any of the aspects, a decreased cooperativity mutation can be a mutation of a residue corresponding to residue 69 of SEQ ID NO: 58, to a valine, methionine, leucine, isoleucine, or alanine residue. In some embodiments of any of the aspects, a decreased cooperativity mutation can be a mutation of a residue corresponding to residue 69 of SEQ ID NO: 58, to a valine or methionine residue.

In some embodiments of any of the aspects, the recombinase comprising at least one decreased cooperativity mutation is $Cre^{R32M}$ or $Cre^{R32V}$.

It is further contemplated herein that a decreased cooperativity mutation can be reversible in nature. For example, the decreased cooperativity mutation can be a mutation to a photo-caged or chemically-caged amino acid that could be triggered to generate the inter-monomer salt-bridge, thereby permitting a user to induce the conversion of non-cooperative monomers to cooperative species. Exemplary residues include methyl-o-nitropiperonyllysine, which can be photo-converted to generate lysine/K, or Azidonorleucine, which can be reduced via phosphine (Staudinger reaction) to generate lysine. These constructs could be generated using genome-expansion method for direct production within cells, or purified from batch expression and subsequently applied to cells. Cre itself, as well as its fusions to TAT, or +36 supercharged GFP, are known to be membrane penetrant.

In some embodiments of any of the aspects, the polypeptide comprises, from N-terminus to C-terminus: the drug-controlled peptide docking domain; a first linker domain; the decreased cooperativity recombinase; a second linker domain; and the cognate docking domain-binding peptide. In some embodiments of any of the aspects, the polypeptide comprises, from N-terminus to C-terminus: the cognate docking domain-binding peptide; a first linker domain; the decreased cooperativity recombinase; a second linker domain; and the drug-controlled peptide docking domain. In some embodiments of any of the aspects, the polypeptide comprises: a) the drug-controlled peptide docking domain at the N-terminus to C-terminus of the decreased cooperativity recombinase with an intervening linker domain; and b) the cognate docking domain-binding peptide inserted into the recombinase at a position corresponding to amino acid 228 or 251 of SEQ ID NO: 58. In some embodiments of any of the aspects, the polypeptide comprises: a) the cognate docking domain-binding peptide at the N-terminus to C-terminus of the decreased cooperativity recombinase with an intervening linker domain; and b) the drug-controlled peptide docking domain inserted into the decreased cooperativity recombinase at a position corresponding to amino acid 228 or 251 of SEQ ID NO:58.

In a second application of the molecule sets described herein, the molecule sets can be used to control a pair of activity-complementing domains. It is contemplated that by providing a drug-controlled peptide docking domain in the same polypeptide as a first activity-complementing domain and a cognate docking domain-binding peptide in the same polypeptide molecule as a second activity-complementing domain, the cognate pair of a drug-controlled peptide docking domain and a docking domain-binding peptide will bind to each other, causing the pair of activity-complementing domains to associate and permit their activity to occur. The addition of the drug will disrupt the binding of the drug-controlled peptide docking domain and a docking domain-binding peptide, thereby dissociating the pair of activity-complementing domains and repressing their activity. However, such systems are very leaky and have limited practical utility.

The inventors have improved on such systems by utilizing a 4 molecule set that includes the drug-controlled peptide docking domain, cognate docking domain-binding peptide, and drug described above an which further includes a drug-resistant peptide docking domain. Using this 4 molecule set, a first activity-complementing domain is flanked on one terminus by a drug-controlled peptide docking domain and flanked on the other terminus by the cognate docking domain-binding peptide. In a separate polypeptide, there is provided a drug-resistant peptide docking domain and a second activity-complementing domain. In the absence of the drug, the intramolecular drug-controlled peptide docking domain and cognate docking domain-binding peptide will bind to each other, causing physical or steric constraints on the ability of the first activity-complementing domain to interact with the second activity-complementing domain. The addition of the drug of the molecule set will disrupt the binding of the drug-controlled peptide docking domain and a docking domain-binding peptide, but permit the binding of the drug-controlled peptide docking domain and the drug-resistant docking domain-binding peptide. The binding of the drug-controlled peptide docking domain and the drug-resistant docking domain-binding peptide causes the pair of activity-complementing domains to associate and permit their activity to occur Accordingly, in one aspect of any of the embodiments, described herein is a system comprising: a) a first polypeptide comprising a first member of a pair of activity-complementing domains flanked on one terminus by a drug-controlled peptide docking domain and flanked on the other terminus by a cognate docking domain-binding peptide; and b) a second polypeptide comprising a second member of a pair of activity-complementing domains flanked on one terminus by a drug-resistant peptide docking domain. In one aspect of any of the embodiments, described herein is a system comprising: a) a first polypeptide comprising a first member of a pair of activity-complementing domains flanked on one terminus by a drug-controlled peptide docking domain and flanked on the other terminus by a cognate docking domain-binding peptide; b) a second polypeptide comprising a second member of a pair of activity-complementing domains flanked on one terminus by a drug-resistant peptide docking domain; and c) a drug that controls the drug-controlled peptide docking domain.

As used herein, "activity-complementing domains" refers to a pair of polypeptide domains that are each inactive in isolation, but when in association (physically bound to each other or part of two molecule physically bound to each other, or merely close enough to interact with the same target), the domains will provide an activity. The domains therefore complement each other to provide an activity. Diverse activity-complementing domains are well known in the art and can include two portions of a naturally occurring enzyme that are engineered to be separate molecules, or pairs of naturally occurring proteins that require their partner molecule to function. Exemplary pairs of activity-complementing domains are provided below herein.

In some embodiments of any of the aspects, a pair of activity-complementing domains can be:
  i) a DNA-binding domain and a transcriptional effector domain;
  ii) a Gal4 DNA-binding domain and a VPR transcriptional effector domain;
  iii) a DNA-binding domain and a transcriptional repressor domain;
  iv) a Gal4 DNA-binding domain and a KRAB transcriptional repressor domain;
  v) a DNA-binding domain and a nuclease domain;
  vi) a DNA-binding domain and a histone modification domain;
  vii) two portions of an enzyme that are inactive when separate and enzymatically active when in physical contact;
  viii) N-luciferase and C-luciferase;
  ix) a ubiquitin ligase and its substrate peptide; or
  x) two portions of a nucleosome localization sequence.

Such pairs are well-known in the art and further discussion can be found, e.g., in Ansari et al. Current Opinion in Chemical Biology 2002 6:765-772 and Shekhawat et al. Current Opinion in Chemical Biology 2011 15:789-797; the contents of which are incorporated by reference herein in their entireties. DNA-binding domains can include but are not limited to Gal4, TetR, rTetR, and zinc finger DNA-binding domains. Enzymes that can be engineered into two separate domains or portions that are inactive when separate and enzymatically active when in physical contact include but are not limited to Caspase9; biotin ligase (e.g., BirA), TEV protease, and ubiquitin ligase.

In some embodiments of any of the aspects, the first polypeptide further comprises a first linker domain between the first member of a pair of activity-complementing domains and the drug-controlled peptide docking domain and second linker domain between the first member of a pair of activity-complementing domains and the cognate docking domain-binding peptide.

In a third application of the molecule sets described herein, the molecule sets can be used to control synthetic receptors. It is contemplated that by providing i) a transmembrane protein comprising both a cognate docking domain-binding peptide and a first activity-complementing domain and ii) a separate polypeptide comprising a drug-controlled peptide docking domain, the cognate pair of a drug-controlled peptide docking domain and a docking domain-binding peptide will bind to each other, causing the pair of activity-complementing domains to associate and permit their activity to occur. This can be further coupled with the control offered by "SynNotch" receptors described herein, wherein perception of an extracellular signal is necessary to activate the intracellular portions of the membrane, e.g., by cleaving them from the transmembrane protein and permitting them to move to a location where they exert their activity (e.g., to the nuclease for a transcriptional regulator). The addition of the drug will disrupt the binding of the drug-controlled peptide docking domain and a docking domain-binding peptide, thereby dissociating the pair of activity-complementing domains and repressing their activity. The drug therefore provides an "off" switch for the transmembrane protein, even in the presence of its own activating signal.

Accordingly, in one aspect of any of the embodiments, described herein is a system comprising: i) a first polypeptide which is a transmembrane polypeptide, the first polypeptide comprising: an extracellular domain comprising a first member of a specific binding pair of molecules, wherein the extracellular domain is heterologous to the Notch receptor; a Notch receptor regulatory domain; a transmembrane domain; a cognate docking domain-binding peptide; and a first member of a pair of activity-complementing domains; and ii) a second polypeptide comprising: a drug-controlled peptide docking domain; and a second member of a pair of activity-complementing domains. It is further contemplated that in any embodiment, the location of the drug-controlled peptide docking domain and the cognate docking domain-binding peptide can be reversed, e.g., the transmembrane protein comprises the drug-controlled peptide docking domain and the second polypeptide comprises the cognate docking domain-binding peptide. Activity-complementing domains are discussed elsewhere herein.

In one aspect of any of the embodiments, described herein is a system comprising: i) a first polypeptide which is a transmembrane polypeptide, the first polypeptide comprising: an extracellular domain comprising a first member of a specific binding pair of molecules, wherein the extracellular domain is heterologous to the Notch receptor; a Notch receptor regulatory domain; a transmembrane domain; a cognate docking domain-binding peptide; and a first member of a pair of activity-complementing domains; ii) a second polypeptide comprising: a drug-controlled peptide docking domain; and a second member of a pair of activity-complementing domains, and iii) a drug that controls the drug-controlled peptide docking domain. In one aspect of any of the embodiments, described herein is a cell comprising or expressing, or a cell comprising one or more nucleic acids encoding a system comprising: i) a first polypeptide which is a transmembrane polypeptide, the first polypeptide comprising: an extracellular domain comprising a first member of a specific binding pair of molecules, wherein the extracellular domain is heterologous to the Notch receptor; a Notch receptor regulatory domain; a transmembrane domain; a cognate docking domain-binding peptide; and a first member of a pair of activity-complementing domains; and ii) a second polypeptide comprising: a drug-controlled peptide docking domain; and a second member of a pair of activity-complementing domains.

Receptors utilizing the Notch receptor regulatory domain, and in which the endogenous extracellular portion of Notch has been replaced with an exogenous binding domain and/or in which exogenous intracellular domains have been added to the receptor are known in the art as "SynNotch." The polypeptides described herein are novel variants of the SynNotch concept. The structure and sequence of necessary SynNotch domains, e.g., the Notch receptor regulatory domain and transmembrane domains and variants thereof are well known in the art and described, e.g., in Morsut et al. Cell 2016 164:780-791; and Yang et al. Communications When the extracellular domain of a SynNotch binds to its ligand (herein, when the first member of a specific binding pair of molecules binds to the second member of a specific binding pair of molecules), a conformational change in the intracellular Notch receptor regulatory domain is caused. This conformational change exposes cleavage sites in the Notch receptor regulatory domain to cleavage by, e.g., gamma secretase. Upon cleavage, all domains of the polypeptide which are c-terminal of the cleavage sites are released from the membrane and can be trafficked to other areas of a cell. In some embodiments of any of the aspects, one or both of the activity-complementing domains can further comprise a trafficking signal, e.g., a nuclear localization signal. Such signals, for different compartments of the cell, are well known in the art.

In view of the role of gamma secretase in control of the SynNotch receptor, a system or cell described herein, comprising a polypeptide comprising a Notch receptor regulatory domain, can further comprise gamma secretase (e.g., NCBI Gene ID Nos: 55851, 51107, and 83464) and/or one or more nucleic acids encoding a gamma secretase. A nucleic acid encoding a gamma secretase can further comprise an inducible promoter, e.g., a doxycycline-inducible promoter.

In some embodiments of any of the aspects, the Notch receptor regulatory region comprises Lin-12 Notch repeats A-C, heterodimerization domains HD-N and HD-C, a binding-induced proteolytic cleavage site, and a transmembrane domain. In some embodiments of any the aspects, the Notch variant is a Notch receptor where the Notch extracellular subunit (NEC) (which includes the negative regulatory region (NRR)) is partially or completely removed. In some embodiments of any of the aspects, the Notch receptor regulatory region is a truncated or modified variant of synNotch, e.g., lacking one or more of the following domains: Lin-12 Notch repeats A-C, heterodimerization domains HD-N and HD-C, a binding-induced proteolytic cleavage site, the Notch extracellular domain (NEC), the negative regulatory region (NRR), or a transmembrane domain.

In some embodiments of any of the aspects, the Notch receptor regulatory region comprises one of SEQ ID NOs: 190-191 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 190-191, that maintains the same function. See e.g., U.S. Pat. No. 10,590,182; Morsut et al., Cell. 2016 Feb. 11; 164(4):780-91; the contents of which are incorporated herein by reference in their entireties.

synNotch (306 aa),
SEQ ID NO: 190
PPQIEEACELPECQVDAGNKVCNLQCNNHACGWDGGDCSLNFNDPWKNC

TQSLQCWKYFSDGHCDSQCNSAGCLFDGFDCQLTEGQCNPLYDQYCKDH

FSDGHCDQGCNSAECEWDGLDCAEHVPERLAAGTLVLVVLLPPDQLRNN

SFHFLRELSHVLHTNVVFKRDAQGQQMIFPYYGHEEELRKHPIKRSTVG

WATSSLLPGTSGGRQRRELDPMDIRGSIVYLEIDNRQCVQSSSQCFQSA

TDVAAFLGALASLGSLNIPYKIEAVKSEPVEPPLPSQLHLMYVAAAAFV

LLFFVGCGVLLS synNotch (358 aa),
SEQ ID NO: 191
PCVGSNPCYNQGTCEPTSENPFYRCLCPAKFNGLLCHILDYSFTGGAGR

DIPPPQIEEACELPECQVDAGNKVCNLQCNNHACGWDGGDCSLNFNDPW

KNCTQSLQCWKYFSDGHCDSQCNSAGCLFDGFDCQLTEGQCNPLYDQYC

KDHFSDGHCDQGCNSAECEWDGLDCAEHVPERLAAGTLVLVVLLPPDQL

RNNSFHFLRELSHVLHTNVVFKRDAQGQQMIFPYYGHEEELRKHPIKRS

TVGWATSSLLPGTSGGRQRRELDPMDIRGSIVYLEIDNRQCVQSSSQCF

QSATDVAAFLGALASLGSLNIPYKIEAVKSEPVEPPLPSQLHLMYVAAA

AFVLLFFVGCGVLLS

Transmembrane domains are well known in the art and can include Notch transmembrane domains or other known transmembrane domains.

In some embodiments of any of the aspects, the system further comprises an extracellular second member of the specific binding pair of molecules.

A pair of molecules are a specific binding pair comprises one molecule that displays specific binding affinity toward a second molecule (the ligand) and comprises at least one ligand binding site for that ligand. In some embodiments, the members of the specific binding pair have an affinity for each other of less than or equal to $10^7$, $10^8$, $10^9$, $10^{10}$, or $10^{11}$ KD. In some embodiments of any of the aspects, the first molecule can be a chimeric protein or protein domain. In some embodiments of any of the aspects, the first molecule can be an antibody, antibody reagent, antibody binding domain, single-chain variable fragment (scFv), nanobody, naturally occurring protein binding domain, peptide, or rationally designed protein with ligand affinity. The ligand in a specific binding pair of molecules can be, e.g., a small molecule, peptide motif, 3D protein epitope, or large macromolecular structure.

Suitable first members of a specific binding pairs include, but are not limited to, antibody-based recognition scaffolds; antibodies (i.e., an antibody-based recognition scaffold, including antigen-binding antibody fragments); non-antibody-based recognition scaffolds; antigens (e.g., endogenous antigens; exogenous antigens; etc.); a ligand for a receptor; a receptor; a target of a non-antibody-based recognition scaffold; an Fc receptor (e.g., FcγRIIIa; FcγRIIIb; etc.); an extracellular matrix component; and the like.

In some embodiments of any of the aspects, the ligand is a molecule that is not naturally present in, e.g., not endogenous to, the cell or organism. In some embodiments of any of the aspects, the ligand is a molecule that is not naturally present in, e.g., not endogenous to, a human cell or organism. In some embodiments of any of the aspects, the ligand is a molecule that is not naturally present in, e.g., not endogenous to, a mammalian cell or organism. In some embodiments of any of the aspects, the ligand is a molecule that is not naturally present in, e.g., not endogenous to, a healthy human cell or organism. In some embodiments of any of the aspects, the ligand is a molecule that is not naturally present in, e.g., not endogenous to, a healthy mammalian cell or organism. In some embodiments of any of the aspects, the ligand is a disease marker, e.g. a cancer marker or antigen. In some embodiments of any of the aspects, the ligand is a molecule found in or on, e.g., expressed or encoded by, a pathogenic organism or virus.

In some embodiments of any of the aspects, the extracellular second member of the specific binding pair of molecules is conjugated, ligated, attached, or bound to a surface. In some embodiments, binding can be non-covalent, e.g., by hydrogen bonding, electrostatic, or van der Waals interactions; however, binding may also be covalent. By "conjugated" is meant the covalent linkage of at least two molecules.

In some embodiments of any of the aspects, the extracellular second member of the specific binding pair of molecules is expressed on the surface of a cell not expressing the first polypeptide and/or second polypeptide.

A surface can be, e.g., a lipid bilayer, a cell surface, or solid surface. In some embodiments of any of the aspects, a lipid bilayer surface can be a liposome. In some embodiments of any of the aspects, the surface is a solid surface or solid support. The surface can be e.g., beads (such as magnetic beads, polystyrene beads, or gold beads); resin; fiber; sheet; biocompatible polymer or material; a nanoparticle; a matrix; a hydrogel; and a biomaterial, biocompatible, and/or biodegradable material; or the like.

A surface can also include a nanocarrier. For example, various nanocarriers are known in the art and can include but are not limited to PLGA nanoparticles, poly(carboxyphenoxypropane/sebacic acid), poly(glycerol monostearate-co-caprolactone), and the like. Such nanocarriers and their use are described in the art, e.g., Rosenblum et al. Nature Communications 2018 9:1410; which is incorporated by reference herein in its entirety.

As used herein, the term "bead" refers to a microparticle of any design or construction, but preferably a microparticle that is about the size of a cell or smaller. While cell sizes vary according to cell type, the bead (microparticles) can be of any such size or smaller, e.g. nanoscale in size. In some embodiments of any of the aspects, the beads or particles can range in size from 1 nm to 1 mm. In some embodiments of any of the aspects, the beads can be about 250 nm to about 250 μm in size.

Suitable materials for a surface include, without limitation, a synthetic polymer, biopolymer, latex, or silica. Such materials are well known in the art. For example, the use of beads and/or particles is known in the art and described, e.g. magnetic bead and nano-particles are well known and methods for their preparation have been described in the are art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety.

As used herein, the term "nanoparticle" refers to particles that are on the order of about 10-9 or one to several billionths of a meter. The term "nanoparticle" includes nanospheres; nanorods; nanoshells; and nanoprisms; these nanoparticles may be part of a nanonetwork. The term "nanoparticles" also encompasses liposomes and lipid particles having the size of a nanoparticle.

As used herein, the term "matrix" refers to a 3-dimensional structure comprising the components of a composition described herein. Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the surface is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

In some embodiments of any of the aspects, any two domains or portions as described herein in a polypeptide can be joined into a single polypeptide by positioning a peptide linker, e.g., a flexible linker between them. As used herein "peptide linker" refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

In some embodiments of any of the aspects, each linker domain/peptide linker is, independently, 5 to 15 amino acids in length. In some embodiments of any of the aspects, each linker domain/peptide linker is, independently, 8 to 11 amino acids in length.

In some embodiments of any of the aspects, each linker domain/peptide linker, independently, comprises serine amino acids, glycine amino acids, or a combination thereof. In some embodiments of any of the aspects, each linker domain/peptide linker, independently, consists of serine amino acids, glycine amino acids, or a combination thereof.

In some embodiments of any of the aspects, a polypeptide described herein is not a naturally occurring polypeptide. In some embodiments of any of the aspects, a polypeptide described herein is an engineered polypeptide. In some embodiments of any of the aspects, the domains and/or portions of a polypeptide described herein are not naturally found in the same polypeptide. In some embodiments of any of the aspects, a cell described herein is not a naturally occurring cell. In some embodiments of any of the aspects, a cell described herein is an engineered cell. In some embodiments of any of the aspects, a cell described herein is engineered because it comprises an engineered polypeptide described herein or a nucleic acid encoding an engineered polypeptide described herein.

In one aspect of any of the embodiments, described herein is a nucleic acid encoding a system or one or more of the polypeptides described herein. In some embodiments of any of the aspects, a vector comprises the nucleic acid. In one aspect of any of the embodiments, described herein is a cell, organism (including a human), or non-human organism comprising a system or one or more of the polypeptides described herein or a nucleic acid or vector encoding a system or one or more of the polypeptides described herein.

In some embodiments of any of the aspects, the cell is a T cell. In some embodiments of any of the aspects, the cell is a cell obtained from a subject. In some embodiments of any of the aspects, the cell is a cell is autologous to a subject. In some embodiments of any of the aspects, the cell is a cell is heterologous to a subject. In some embodiments of any of the aspects, a method described herein can comprise a first step of obtaining a cell from a donor and/or the subject and contacting the cell with one or more of the polypeptides, systems, or nucleic acids encoding a polypeptide or system as described herein.

In some embodiments of any of the aspects, the cell does not comprise the drug. In some embodiments of any of the aspects, the cell does comprise the drug. In some embodiments of any of the aspects, the cell does not express or produce the drug, e.g., the drug must be added or obtained from an exogenous source for it to be present in the cell.

The systems described herein that comprise a recombinase can be utilized in a method of controlling the activity of the recombinase. According, in one aspect of any of the embodiments, described herein is a method of inducing the activity of a recombinase, the method comprising contacting a system comprising a polypeptide comprising: a) a drug-controlled peptide docking domain; b) a cognate docking domain-binding peptide; and c) a recombinase comprising at least one decreased cooperativity mutation with a drug that controls the drug-controlled peptide docking domain, thereby inducing the activity of the recombinase.

In some embodiments of any of the aspects, when active, the recombinase induces a genetic modification that will induce or suppress expression of a target gene in the cell, e.g, a target gene comprising or flanked by suitable RSS sequences, or a target gene with a operably linked regulatory sequence (e.g., a promoter that comprises or is flanked by suitable RSS sequences). In some embodiments of any of the aspects, the target gene encodes a receptor, e.g., a chimeric antigen receptor. In some embodiments of any of the aspects, the target gene encodes an enzyme responsible for production of a bioproduct or therapeutic produced by the cell. In some embodiments of any of the aspects, the target gene encodes a gene with toxicity, e.g., a constitutively dimerizing Caspase9 monomer, or a domain to inducible dimerize quiescent monomers already expressed within the cell, or thymidine kinase from Herpes Simplex Virus, which is able to catalyze the conversion of the nontoxic prodrug ganciclovir into a cytotoxic agent. In this way, the system comprising a recombinase can induce cell death, e.g., of a CAR-T or a probiotic that is no longer desired to be present in a subject. In some embodiments of any of the aspects, the cell is engineered to comprise a target gene, e.g., a target gene comprising and/or flanked by suitable RSS sequences. The target gene can be native or endogenous to the cell, or engineered or exogenous to the cell.

The systems described herein that comprise a pair of activity-complementing domains can be utilized in a method of controlling the activity of the pair of activity-complementing domains. According, in one aspect of any of the embodiments, described herein is a method of controlling the activity of a pair of activity-complementing domains, the method comprising contacting a system comprising a) a first polypeptide comprising a first member of a pair of activity-complementing domains flanked on one terminus by a drug-controlled peptide docking domain and flanked on the other terminus by a cognate docking domain-binding peptide; and b) a second polypeptide comprising a second member of a pair of activity-complementing domains flanked on one terminus by a drug-resistant peptide docking domain. with a drug that controls the drug-controlled peptide docking domain, thereby inducing the activity of the pair of activity-complementing domains.

In one aspect of any of the embodiments, described herein is a method of controlling the activity of a pair of activity-complementing domains, the method comprising: contacting a system comprising i) a first polypeptide which is a transmembrane polypeptide, the first polypeptide comprising: an extracellular domain comprising a first member of a specific binding pair of molecules, wherein the extracellular domain is heterologous to the Notch receptor; a Notch receptor regulatory domain; a transmembrane domain; a cognate docking domain-binding peptide; and a first member of a pair of activity-complementing domains; and ii) a second polypeptide comprising: a drug-controlled peptide docking domain; and a second member of a pair of activity-complementing domains with second member of the specific binding pair of molecules, thereby inducing the activity of the pair of activity-complementing domains; and/or contacting the said system with a drug that controls the drug-controlled peptide docking domain, thereby reducing the activity of the pair of activity-complementing domains.

In some embodiments of any of the aspects, when active, pair of activity-complementing domains induces a genetic modification that will induce or suppress expression of a target gene in the cell, e.g, a target gene with a suitable promoter sequence. In some embodiments of any of the aspects, the target gene encodes a receptor, e.g., a chimeric antigen receptor. In some embodiments of any of the aspects, the target gene encodes an enzyme responsible for production of a bioproduct or therapeutic produced by the cell. In some embodiments of any of the aspects, the target gene encodes a gene with toxicity, e.g., a constitutively dimerizing Caspase9 monomer, or a domain to inducible dimerize quiescent monomers already expressed within the cell, or thymidine kinase from Herpes Simplex Virus, which is able to catalyze the conversion of the nontoxic prodrug ganciclovir into a cytotoxic agent. In this way, the system comprising a pair of activity-complementing domains can induce cell death, e.g., of a CAR-T or a probiotic that is no longer desired to be present in a subject. In some embodiments of any of the aspects, the cell is engineered to comprise a target gene, e.g., a target gene comprising a suitable promoter The target gene can be native or endogenous to the cell, or engineered or exogenous to the cell.

The foregoing systems relating to recombinases and pairs of activity-complementing domains can be utilized to, e.g, screen for new drugs. Existing NS3 inhibitors have been discovered via the replicon assay, typically carried out in HUH-7 or other similar liver-derived lines. The replicon assay is based on self-replicating RNA expressing NS3 and other components. Readouts (e.g., the target genes or products thereof) can include GFP, other reporters, and selectable markers introduced to the cell line via replicon RNA sequence. In some embodiments of such assays performed with the systems described herein can include two measurable states (e.g., pre- and post-recombination for example). As an example, pre-state might be specified by GFP fused to zeocin resistance marker, and post-state should cause cells to stop expressing GFP-zeo, and express instead mCherry fused to a puromycin resistance marker. Such a dual state approach would permit positive and negative selections in the engineering of optimal inducible constructs (express construct, sort/select against any that recombine gene target in absence of drug, screen for a positive pool, isolate that pool, treat with drug, and then identify clones that transition to post-recom state). The addition of degron to facilitate rapid elimination of pre-state marker (GFP-zeo-pest, for example) would be advantageous in the distinction between states during screening. Accordingly, in one aspect of any of the embodiments, the cell described herein further comprises a target gene(s) that express a detectable, screenable, or selectable marker prior to addition of drug and expresses a different dectable, screenable, or selectable marker after addition of drug. In one aspect of any of the embodiments, described herein is a method of selecting or identifying a drug, the method comprising contacting the foregoing cell with candidate drugs and identifying as a drug any of the candidates that induce the expression of the marker expressed after addition of a drug.

In one aspect of any of the embodiments, described herein is a method of treating cancer in a subject in need thereof, the method comprising: administering to the subject a T cell comprising, expressing, or encoding a system comprising i) a first polypeptide which is a transmembrane polypeptide, the first polypeptide comprising: an extracellular domain comprising a first member of a specific binding pair of molecules, wherein the extracellular domain is heterologous to the Notch receptor; a Notch receptor regulatory domain; a transmembrane domain; a cognate docking domain-binding peptide; and a first member of a pair of activity-complementing domains; and ii) a second polypeptide comprising: a drug-controlled peptide docking domain; and a second member of a pair of activity-complementing domains, wherein the second member of the specific binding pair of molecules is a cancer antigen. When the cancer antigen is present, the first polypeptide will be activated, interact with the second polypeptide, and the activity of the pair of activity-complementing domains will be exerted. In some embodiments of any of the aspects, the method further comprises administering a drug that controls the drug-controlled peptide docking domain, whereby anti-cancer activity of the T cell is reduced or suppressed. In some embodiments of any of the aspects, the T cell is autologous to the patient.

It is further contemplated that in any embodiment, the location of the drug-controlled peptide docking domain and the cognate docking domain-binding peptide can be reversed, e.g., the transmembrane protein comprises the drug-controlled peptide docking domain and the second polypeptide comprises the cognate docking domain-binding peptide.

Cancer antigens are known in the art and can include, but are not limited to: EpCAM, CD46, CD24, CD133, CD19, CD30, CD33, CD123, FLT3, and BCMA.

Antibody reagents specific for the targets and/or markers described herein, e.g., a member of a specific binding pair of molecules that binds specifically to a cancer antigen, or anti-GFP reagents are known in the art. For example, such reagents are readily commercially available. In some embodiments of any of the aspects, an antibody reagent specific for a target and/or maker described herein (e.g., that binds specifically to the target and/or marker) can be an antibody reagent comprising one or more (e.g., one, two, three, four, five, or six) CDRs of any one of the antibodies recited in Table 3. In some embodiments of any of the aspects, an antibody reagent specific for a target and/or maker described herein (e.g., that binds specifically to the target and/or marker) can be an antibody reagent comprising the six CDRs of any one of the antibodies recited in Table 3. In some embodiments of any of the aspects, an antibody reagent specific for a target and/or marker described herein (e.g., that binds specifically to the target and/or marker) can be an antibody reagent comprising the three heavy chain CDRs of any one of the antibodies recited in Table 3. In some embodiments of any of the aspects, an antibody reagent specific for a target and/or marker described herein (e.g., that binds specifically to the target and/or marker) can be an antibody reagent comprising the three light chain CDRs of any one of the antibodies recited in Table 3. In some embodiments of any of the aspects, an antibody reagent specific for a target and/or maker described herein (e.g., that binds specifically to the target and/or marker) can be an antibody reagent comprising the VH and/or VL domains of any one of the antibodies recited in Table 3. In some embodiments of any of the aspects, an antibody reagent specific for a target and/or marker described herein (e.g., that binds specifically to the target and/or marker) can be an antibody reagent comprising the VH and VL domains of any one of the antibodies recited in Table 3. Such antibody reagents are specifically contemplated for use in the methods and/or compositions described herein.

TABLE 3

Exemplary anti-cancer antigen antibody reagents

| Target/Antigen | Exemplary Antibodies |
| --- | --- |
| CD19 | HIBI9 (ThermoFisher Cat. No. 12-0199-42) |
| | 1D3 (ThermoFisher Cat. No. 25-0193-82) |
| | 6OMP31 (ThermoFisher Cat. No. 14-0194-82) |
| | SJ25C1 (ThermoFisher Cat. No. 47-0198-42) |
| | LC1 (ThermoFisher Cat. No. 14-0190-82) |
| | 771404 (ThermoFisher Cat. No. MA5-24372) |
| | EPR5906 (AbCam Cat. No. ab134114) |
| | EPR23174-145 (AbCam Cat. No. ab245235) |
| | SP291 (AbCam Cat. No. ab227688) |
| | SP110 (AbCam Cat. No. ab225717) |
| | BU12 (AbCam Cat. No. ab254170) |
| | CD19/3117 (AbCam Cat. No. ab270715) |

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In some embodiments of any of the aspects, the methods described herein relate to treating a subject having or diagnosed as having cancer with a composition or system as described herein. Subjects having cancer can be identified by a physician using current methods of diagnosing cancer. Symptoms and/or complications of cancer which characterize these conditions and aid in diagnosis are well known in the art and include but are not limited to, for example, a lump/mass/tumor, swelling, or pain. Tests that may aid in a diagnosis of, e.g. cancer include, but are not limited to, x-rays, MRI, ultrasound, a biopsy, or tests for the function/activity of affected organs or systems. A family history of cancer or exposure to risk factors for cancer (e.g. smoke, radiation, pollutants, mutation, etc.) can increase the risk of a subject having cancer.

The compositions and methods described herein can be administered to a subject having or diagnosed as having cancer. In some embodiments of any of the aspects, the methods described herein comprise administering an effective amount of compositions described herein to a subject in order to alleviate a symptom of a cancer. As used herein, "alleviating a symptom" of a cancer is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic. In some embodiments of any of the aspects, the administration is subcutaneous.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a cell, system, and/or drug, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor cell growth, among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments, the technology described herein relates to a pharmaceutical composition comprising a system, or cell comprising or encoding a system as described herein, and optionally a pharmaceutically acceptable carrier. In some embodiments, the active ingredients of the pharmaceutical composition comprise a system, or cell comprising or encoding a system as described herein. In some embodiments, the active ingredients of the pharmaceutical composition consist essentially of a system, or cell comprising or encoding a system as described herein. In some embodiments, the active ingredients of the pharmaceutical composition consist of a system, or cell comprising or encoding a system as described herein. In some embodiments of any of the aspects, the pharmaceutical composition can further comprise a drug that controls the drug-controlled peptide docking domain. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a system, or cell comprising or encoding a system as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of compositions as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a molecule as disclosed herein can also be incorporated into the parenteral dosage forms of the disclosure, including conventional and controlled-release parenteral dosage forms.

Pharmaceutical compositions comprising a system, or cell comprising or encoding a system can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the a system, or cell comprising or encoding a system can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the a system, or cell comprising or encoding a system described herein is administered as a monotherapy, e.g., another treatment for the condition (e.g., cancer) is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cipslatin, paclitaxel, carboplatin, bortezomib, AMG479, vorinostat, rituximab, temozolomide, rapamycin, ABT-737, PI-103; alkylating agents such as thiotepa and CYTOXAN@cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising a system, or cell comprising or encoding a system as described herein can be administered to a patient once. In certain embodiments, an effective dose of a composition comprising a system, or cell comprising or encoding a system can be administered to a patient repeatedly. For systemic administration, subjects can be administered a therapeutic amount of a composition comprising a system, or cell comprising or encoding a system, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor cell growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a system, or cell comprising or encoding a system can be administered over a period of time, such as over a 5 minute, 10 minute, 15 minute, 20 minute, or 25 minute period.

The dosage ranges for the administration of a system, or cell comprising or encoding a system, or drug according to the methods described herein depend upon, for example, the form of a system, or cell comprising or encoding a system, or a drug, its potency, and the extent to which symptoms, markers, or indicators of a condition described herein are desired to be reduced, for example the percentage reduction desired for tumor cell growth or the extent to which, for example, target gene activation are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a system, or cell comprising or encoding a system, or a drug in, e.g. the treatment of a condition described herein, or to induce a response as described herein (e.g. cancer) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor cell growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a reduction in tumor cell growth or increase in target gene expression). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor cell growth or target gene expression.

Another aspect of the technology described herein relates to kits for controlling activity/expression as described herein and/or treating a subject (e.g., a subject in need of cell therapy), among others. Described herein are kit components that can be included in one or more of the kits described herein.

In some embodiments, the kit comprises an effective amount of a polypeptide or system as described herein. As will be appreciated by one of skill in the art, the polypeptide or system can be supplied in a lyophilized form or a concentrated form that can diluted or suspended in liquid prior to use, e.g., with cells. Preferred formulations include those that are non-toxic to the cells and/or does not affect growth rate or viability and can be supplied in aliquots or in unit doses.

In some embodiments the kit further comprises a vector comprising a nucleic acid encoding a polypeptide or system as described herein. In some embodiments, the polypeptide or system is under the control of an inducible promoter, e.g., for inducible expression in vitro, in vivo, or ex vivo.

In some embodiments, the components described herein can be provided singularly or in any combination as a kit. Such a kit includes the components described herein, e.g., a composition comprising a polypeptide or system as described herein or a composition that includes a vector comprising a polypeptide or system as described herein.

In some embodiments, the kit comprises an drug as described herein (e.g., caffeine, abscisic acid, rapamycin, gibberellin, protease inhibitor, or analogs thereof). In some In some embodiments, the compositions in the kit can be provided in a watertight or gas tight container which in some embodiments is substantially free of other components of the kit. For example, a composition can be supplied in more than one container, e.g., it can be supplied in a container having sufficient reagent for a predetermined number of cell culture events, e.g., 1, 2, 3 or greater. One or more components as described herein can be provided in any form, e.g., liquid, dried or lyophilized form. It is preferred that the components described herein are substantially pure and/or sterile. When the components described herein are provided in a liquid solution, the liquid solution preferably is an aqueous solution, with a sterile aqueous solution being preferred.

In addition, the kit optionally comprises informational material. The informational material can be descriptive, instructional, marketing or other material that relates to the methods described herein. The informational material of the kits is not limited in its form. In one embodiment, the informational material can include information about production of the polypeptide or system, concentration, date of expiration, batch or production site information, and so forth. In one embodiment, the informational material relates to methods for using or administering the components of the kit.

The kit can be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

In one respect, the present invention relates to the herein described compositions, methods, and respective component(s) thereof, as essential to the technology, yet open to the inclusion of unspecified elements, essential or not ("comprising). In some embodiments of any of the aspects, other elements to be included in the description of the composition, method or respective component thereof are limited to those that do not materially affect the basic and novel characteristic(s) of the technology (e.g., the composition, method, or respective component thereof "consists essentially of" the elements described herein). This applies equally to steps within a described method as well as compositions and components therein. In other embodiments of any of the aspects, the compositions, methods, and respective components thereof, described herein are intended to be exclusive of any element not deemed an essential element to the component, composition or method (e.g., the composition, method, or respective component thereof "consists of" the elements described herein). This applies equally to steps within a described method as well as compositions and components therein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., cancer. A subject can be male or female.

A subject can be one who has been previously diagnosed with or identified as suffering from or having a condition in need of treatment (e.g. cancer) or one or more complications related to such a condition, and optionally, have already undergone treatment for the condition or the one or more complications related to the condition Alternatively, a subject can also be one who has not been previously diagnosed as having a condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, of the full length polypeptide. Conservative substitution variants that maintain the activity of a wildtype protein will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by assaying the variant for the relevant activity in a cell or cell-free system.

In some embodiments, a polypeptide, can be a variant of a sequence described herein, e.g. a variant of a polypeptide comprising an amino acid sequence described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can at least 50% as much as wildtype. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of the wildtype, e.g. 110%, 125%, 150%, 175%, 200%, 500%, 1000% or more.

One method of identifying amino acid residues which can be substituted is to align, for example, a human protein to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the activity and/or specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments, a polypeptide can comprise one or more amino acid substitutions or modifications. In some embodiments, the substitutions and/or modifications can prevent or reduce proteolytic degradation and/or prolong half-life of the polypeptide in a subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established. Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama and Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application 20040161738 published Aug. 19, 2004; which is incorporated by reference herein in its entirety.

As described herein, an "antigen" is a molecule that is specifically bound by a B cell receptor (BCR), T cell receptor (TCR), and/or antibody. An antigen can be pathogen-derived, or originate from a pathogen. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

As used herein, the terms "candidate compound" or "candidate agent" refer to a compound or agent and/or compositions thereof that are to be screened for their ability to bind or modulate the activity of a target or component of a system. Candidate drugs are candidate compounds or candidate agents to be screen for their ability to function as a drug in a system described herein. Candidate compounds and agents can be screened for their ability to and/or activity in vitro or in vivo.

As used herein, the terms "compound" or "agent" are used interchangeably and refer to molecules and/or compositions. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

Generally, compounds can be tested at any concentration that can modulate expression or protein activity relative to a control over an appropriate time period. In some embodiments, compounds are tested at concentration in the range of about 0.1 nM to about 1000 mM. In one embodiment, the compound is tested in the range of about 0.1 µM to about 20 µM, about 0.1 µM to about 10 µM, or about 0.1 µM to about 5 µM. In one embodiment, compounds are tested at 1 µM.

Depending upon the particular embodiment being practiced, the candidate compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylenemaleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Marker" in the context of the present invention refers to an expression product, e.g., nucleic acid or polypeptide which is differentially present in a sample taken from subjects having a condition, as compared to a comparable sample taken from control subjects (e.g., a healthy subject). The term "biomarker" is used interchangeably with the term "marker."

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, a polypeptide, system, and/or drug described herein is exogenous. In some embodiments of any of the aspects, a polypeptide, system, and/or drug described herein is ectopic. In some embodiments of any of the aspects, a polypeptide, system, and/or drug described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a polypeptide as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "nanoparticle" refers to particles that are on the order of about 1 to 1,000 nanometers in diameter or width. The term "nanoparticle" includes nanospheres; nanorods; nanoshells; and nanoprisms; these nanoparticles may be part of a nanonetwork. The term "nanoparticles" also encompasses liposomes and lipid particles having the size of a nanoparticle. Exemplary nanoparticles include lipid nanoparticles or ferritin nanoparticles. Lipid nanoparticles can comprise multiple components, including, e.g., ionizable lipids (such as MC3, DLin-MC3-DMA, ALC-0315, or SM-102), pegylated lipids (such as PEG2000-C-DMG, PEG2000-DMG, ALC-0159), phospholipids (such as DSPC), and cholesterol.

Exemplary liposomes can comprise, e.g., DSPC, DPPC, DSPG, Cholesterol, hydrogenated soy phosphatidylcholine, soy phosphatidyl choline, methoxypolyethylene glycol (mPEG-DSPE) phosphatidyl choline (PC), phosphatidyl glycerol (PG), distearoylphosphatidylcholine, and combinations thereof.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell.

Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

In some embodiments, the present technology may be defined in any of the following numbered paragraphs:

1. A polypeptide comprising:
    a) a drug-controlled peptide docking domain;
    b) a cognate docking domain-binding peptide; and
    c) a recombinase comprising at least one decreased cooperativity mutation.
2. The polypeptide of paragraph 1, wherein the polypeptide comprises, from N-terminus to C-terminus: the drug-controlled peptide docking domain; a first linker domain; the recombinase; a second linker domain; and the cognate docking domain-binding peptide.
3. The polypeptide of paragraph 1, wherein the polypeptide comprises, from N-terminus to C-terminus: the cognate docking domain-binding peptide; a first linker domain; the recombinase; a second linker domain; and the drug-controlled peptide docking domain.
4. The system of paragraph 1, wherein the polypeptide comprises:
    a) the drug-controlled peptide docking domain at the N-terminus to C-terminus of the recombinase with an intervening linker domain; and
    b) the cognate docking domain-binding peptide inserted into the recombinase at a position corresponding to amino acid 228 or 251 of SEQ ID NO: 58 (Cre).
5. The system of paragraph 1, wherein the polypeptide comprises:
    a) the cognate docking domain-binding peptide at the N-terminus to C-terminus of the recombinase with an intervening linker domain; and
    b) the drug-controlled peptide docking domain inserted into the recombinase at a position corresponding to amino acid 228 or 251 of SEQ ID NO: 58 (Cre).
6. The polypeptide of any one of paragraphs 1-5, wherein the recombinase is a tyrosine recombinase.
7. The polypeptide of paragraph 1-6, wherein the tyrosine recombinase is Cre, VCre, SCre, Flippase (Flp) XerA, XerC, or XerD.
8. The polypeptide of any one of paragraphs 1-7, wherein the decreased cooperativity mutation is a mutation at a residue corresponding to the R32, E69, 303, 304, or 305 residues of SEQ ID NO: 58 (Cre).
9. The polypeptide of any one of paragraphs 1-8, wherein the decreased cooperativity mutation is a mutation at a residue corresponding to the R32 residue of SEQ ID NO: 58 (Cre).
10. The polypeptide of paragraph 1-9, wherein the decreased cooperativity mutation is a mutation to a residue that does not have a positive charge.
11. The polypeptide of paragraph 1-9, wherein the decreased cooperativity mutation is a mutation to a naturally occurring residue that does not have a positive charge.
12. The polypeptide of paragraph 1-9, wherein the decreased cooperativity mutation is a mutation to a hydrophobic residue.
13. The polypeptide of paragraph 1-12, wherein the decreased cooperativity mutation is a mutation to a valine, methionine, leucine, isoleucine, or alanine residue.
14. The polypeptide of paragraph 1-12, wherein the decreased cooperativity mutation is a mutation to a valine or methionine residue.
15. The polypeptide of paragraph 1-14, wherein the recombinase comprising at least one decreased cooperativity mutation is $Cre^{R32M}$ or $Cre^{R32V}$.
16. A system comprising the polypeptide of any one of paragraphs 1-15 and a drug that controls the drug-controlled peptide docking domain.
17. A system comprising:
    a) a first polypeptide comprising a first member of a pair of activity-complementing domains flanked on one terminus by a drug-controlled peptide docking domain and flanked on the other terminus by a cognate docking domain-binding peptide; and
    b) a second polypeptide comprising a second member of a pair of activity-complementing domains flanked on one terminus by a drug-resistant peptide docking domain.

18. The system of paragraph 16, wherein the pair of activity-complementing domains are:
   xi) a DNA-binding domain and a transcriptional effector domain;
   xii) a Gal4 DNA-binding domain and a VPR transcriptional effector domain;
   xiii) a DNA-binding domain and a transcriptional repressor domain;
   xiv) a Gal4 DNA-binding domain and a KRAB transcriptional repressor domain;
   xv) a DNA-binding domain and a nuclease domain;
   xvi) a DNA-binding domain and a histone modification domain;
   xvii) two portions of an enzyme that are inactive when separate and enzymatically active when in physical contact;
   xviii) N-luciferase and C-luciferase;
   xix) a ubiquitin ligase and its substrate; or
   xx) two portions of a nucleosome localization sequence.
19. The system of paragraph 18, wherein the DNA-binding domain is selected from a Gal4, TetR, rTetR, or a zinc finger DNA-binding domain.
20. The system of paragraph 18, wherein the two portions of an enzyme that are inactive when separate and enzymatically active when in physical contact are portions of Caspase9; biotin ligase (e.g., BirA), TEV protease, and a ubiquitin ligase.
21. The system of any one of paragraphs 17-20, wherein the first polypeptide further comprises a first linker domain between the first member of a pair of activity-complementing domains and the drug-controlled peptide docking domain and second linker domain between the first member of a pair of activity-complementing domains and the cognate docking domain-binding peptide.
22. The system of any one of paragraphs 17-21, further comprising a drug that controls the drug-controlled peptide docking domain.
23. A system comprising:
   a) a first polypeptide which is a transmembrane polypeptide, the first polypeptide comprising:
      i) an extracellular domain comprising a first member of a specific binding pair of molecules, wherein the extracellular domain is heterologous to the Notch receptor;
      ii) a Notch receptor regulatory domain;
      iii) a transmembrane domain;
      iv) a cognate docking domain-binding peptide; and
      v) a first member of a pair of activity-complementing domains; and
   b) a second polypeptide comprising:
      i) a drug-controlled peptide docking domain; and
      ii) a second member of a pair of activity-complementing domains.
24. The system of paragraph 23, wherein the pair of activity-complementing domains are:
   k) a DNA-binding domain and a transcriptional effector domain;
   l) a Gal4 DNA-binding domain and a VPR transcriptional effector domain;
   m) a DNA-binding domain and a transcriptional repressor domain;
   n) a Gal4 DNA-binding domain and a KRAB transcriptional repressor domain;
   o) a DNA-binding domain and a nuclease domain;
   p) a DNA-binding domain and a histone modification domain;
   q) two portions of an enzyme that are inactive when separate and enzymatically active when in physical contact;
   r) N-luciferase and C-luciferase;
   s) a ubiquitin ligase and its substrate; and
   t) two portions of a nucleosome localization sequence.
25. The system of paragraph 24, wherein the DNA-binding domain is selected from a Gal4, TetR, rTetR, or a zinc finger DNA-binding domain.
26. The system of paragraph 24, wherein the pair of activity-complementing domains comprises a Gal4 DNA-binding domain and a transcriptional effector domain;
27. The system of any of paragraphs 23-26, further comprising a cell expressing the system of paragraph 23.
28. The system of paragraph 27, further comprising an extracellular second member of the specific binding pair of molecules.
29. The system of paragraph 28, wherein the extracellular second member of the specific binding pair of molecules is ligated, attached, or bound to a surface.
30. The system of paragraph 25, wherein the extracellular second member of the specific binding pair of molecules is expressed on the surface of a cell not expressing the system of paragraph 23.
31. The system of any one of paragraphs 23-30, further comprising a drug that controls the drug-controlled peptide docking domain.
32. The polypeptide or system of any one of paragraphs 1-31, wherein the drug-controlled peptide docking domain comprises a catalytically inactive drug-controlled peptide docking domain.
33. The polypeptide or system of any one of paragraphs 1-32, wherein the drug-controlled peptide docking domain is selected from NS3; BCL-xL; and a GFP affinity domain.
34. The polypeptide or system of any one of paragraphs 1-33, wherein the drug-controlled peptide docking domain is catalytically inactive NS3 comprising a mutation of the catalytic serine, wherein the catalytic serine is the serine corresponding to S139 of SEQ ID NO: 91 (NS3).
35. The polypeptide or system of paragraph 34, wherein the mutation of the catalytic serine is an alanine substitution.
36. The system of any one of paragraphs 1-35, wherein the drug-controlled peptide docking domain or drug-resistant peptide docking domain is a drug-resistant NS3 selected from NS3$^{AI}$ (comprising V36M, T54A, and S122G relative to SEQ ID NO: 2) and NS3$^{TI}$(F43L, Q80K, S112R, and D168Y relative to SEQ ID NO: 91).
37. The polypeptide or system of any one of paragraphs 1-36, wherein the drug-controlled peptide docking domain is NS3 and the cognate docking domain-binding peptide is CP5-46-4D5E; PMED or P$_{HI}$.
38. The polypeptide or system of any one of paragraphs 1-37, wherein the drug-controlled peptide docking domain is BCL-xL and the cognate docking domain-binding peptide is BAD.
39. The polypeptide or system of any one of paragraphs 1-38, wherein the drug-controlled peptide docking domain is a GFP affinity domain and the cognate docking domain-binding peptide is a non-optimal affinity GFP polypeptide or anti-GFP nanobody.

40. The polypeptide or system of any one of paragraphs 1-39, wherein the drug-controlled peptide docking domain is NS3 and the drug is selected from the group consisting of: grazoprevir, glecaprevir, danoprevir, asunaprevir, telaprevir, boceprevir, simeprevir, paritaprevir, voxilaprevir, narlaprevir, and ciluprevir.

41. The polypeptide or system of any one of paragraphs 1-35 and 38, wherein the drug-controlled peptide docking domain is BCL-xL and the drug is ABT-737, ABT-263 (navitoclax), or GX15-070 (obatoclax).

42. The polypeptide or system of any one of paragraphs 1-35 and 39, wherein the drug-controlled peptide docking domain is a fluorescent protein, the docking domain-binding peptide is a lower-affinity fluoresecent protein affinity domain, and the drug is a higher-affinity fluoresecent protein affinity domain.

43. The polypeptide or system of paragraph 42, wherein the fluorescent protein is GFP. 44. The polypeptide or system of any one of paragraphs 1-43, wherein each linker domain is, independently, 8 to 11 amino acids in length.

45. The polypeptide or system of any one of paragraphs 1-44, wherein each linker domain, independently, comprises serine and/or glycine amino acids.

46. The polypeptide or system of any one of paragraphs 1-45, wherein each linker domain, independently, consists of serine and/or glycine amino acids.

47. A nucleic acid encoding the polypeptide or system of any one of paragraphs 1-46.

48. A vector comprising the nucleic acid of paragraph 47.

49. A cell or non-human organism comprising the polypeptide or system of any one of paragraphs 1-46, the nucleic acid of paragraph 47, or the vector of paragraph 48.

50. The cell of paragraph 49, wherein the cell is a T cell.

51. A method of controlling the activity of a recombinase, the method comprising contacting the system of any one of paragraphs 1-16 and 32-45 with a drug that controls the drug-controlled peptide docking domain, thereby inducing the activity of the recombinase.

52. The method of paragraph 51, wherein the recombinase induces a genetic modification that will induce or suppress expression of a target gene in the cell.

53. The method of paragraph 52, wherein the target gene encodes a receptor.

54. The method of paragraph 53, wherein the receptor is a chimeric antigen receptor.

55. The method of paragraph 52, wherein the target gene encodes an enzyme responsible for production of a bioproduct or therapeutic produced by the cell.

56. A method of controlling the activity of a pair of activity-complementing domains, the method comprising contacting the system of any one of paragraphs 17-22 and 32-46 with a drug that controls the drug-controlled peptide docking domain, thereby inducing the activity of the pair of activity-complementing domains.

57. A method of controlling the activity of a pair of activity-complementing domains, the method comprising:
a) contacting the system of any one of paragraphs 17-22 and 32-46 with second member of the specific binding pair of molecules, thereby inducing the activity of the pair of activity-complementing domains; and/or
b) contacting the system of any one of paragraphs 17-22 and 32-46 with a drug that controls the drug-controlled peptide docking domain, thereby reducing the activity of the pair of activity-complementing domains.

58. The method of any one of paragraphs 56-58, wherein the activity of the pair of activity-complementing domains induces or suppresses expression of a target gene in the cell.

59. The method of paragraph 58, wherein the target gene encodes a receptor.

60. The method of paragraph 59, wherein the receptor is a chimeric antigen receptor.

61. The method of paragraph 58, wherein the target gene encodes an enzyme responsible for production of a bioproduct or therapeutic produced by the cell.

62. A method of screening a candidate drug, the method comprising contacting the system of any one of paragraphs 17-22 and 32-46, wherein the activity of the pair of activity-complementing domains induces or suppresses expression of a target gene in the cell, with a candidate drug; and screening or selecting for the induction or suppression of expression of the target gene, wherein the induction or suppression of expression indicates that the candidate drug is a drug that controls the drug-controlled peptide docking domain, thereby inducing the activity of the pair of activity-complementing domains.

63. A method of treating cancer in a subject in need thereof, the method comprising: administering to the subject a T cell of paragraph 50, wherein the T cell comprises the system of any one of paragraphs 23-46, wherein the second member of the specific binding pair of molecules is a cancer antigen.

64. The method of paragraph 63, further comprising administering a drug that controls the drug-controlled peptide docking domain, whereby anti-cancer activity of the T cell is reduced or suppressed.

65. The method of any of paragraphs 63-64, wherein the T cell is autologous to the patient.

EXAMPLES

Example 1: Controlled Protein Function with Antiviral Peptides and Drugs

To specifically study and control biological systems, orthogonal ligands are needed to regulate protein function. Accordingly, hepatitis C cis-protease NS3 and its associated antiviral drugs have been used to regulate protein activity and gene modulation, which instead rely on non-eukaryotic/prokaryotic proteins and antiviral drugs. To expand the use of these orthogonal ligands, protein-protein and intramolecular interactions can be mediated by genetically encoded peptide inhibitors. Described herein is a catalytically inactive NS3 as a high affinity binder to antiviral peptides and small molecule drugs. These tools are employed to successfully modulate transcription, cell signaling, split-protein complementation, and develop a new mechanism for allosteric regulation of Cre recombinase. This concept of drug-displaceable antiviral peptide docking has multiple applications in eukaryotes and permits a new prokaryotic drug-dependent recombinase activity.

Chemical control of protein activity is a powerful tool for scientific study, synthetic biology, and cell therapy; however, in each use case, effective chemical inducer systems must minimally crosstalk with endogenous processes and exhibit desirable drug delivery properties. Accordingly, hepatitis C cis-protease NS3 and its associated antiviral drugs have been used to regulate protein activity and gene modulation, which advantageously exploit non-eukaryotic/prokaryotic proteins and clinically approved inhibitors. Described herein is the use of catalytically inactive NS3 as a high affinity binder to genetically encoded, antiviral peptides. NS3-peptide complexes can then be displaced by small molecule antiviral drugs to modulate transcription, cell signaling, split-protein complementation, and a new mechanism for allosteric regulation of Cre recombinase. This concept of drug-displaceable antiviral peptide docking has multiple applications in eukaryotes and newly enables drug-dependent, prokaryotic recombinase activity.

Tunable and temporal control of protein activity is critical for the study of biological phenomena, and more recently, for the application of cellular therapies. To achieve protein activity control, proteins are engineered to sense small molecules, light, and even mechanical forces. Small molecules are particularly useful because it can be dose-dependent, dynamic, and highly bioavailable through multiple administration routes. Correspondingly, various ligand-dependent methods have been devised to control protein activity, including chemically induced protein proximity (CIPP)I-[2], induced protein trafficking[3], and controlled enzymatic activity[4]. Previous ligands often exhibit endogenous crosstalk in mammalian organisms, their associated microbiome, or exhibit poor bioavailability.

Each extant ligand inducible system has allowed new functionalities to study and dictate cellular processes. However, previous systems predominantly derive from and target endogenous pathways in eukaryotes and prokaryotes, which can present crosstalk with the host organism or a host's microbiome. For example, rapamycin and its associated rapalogs have allowed for tight control of CIPP, but can present undesired effects on the diverse functions of the mTOR pathways. Other commonly used small molecule inducers such as 4-hydroxytamoxifen and tetracycline have also been critical biological tools, but they too derive from eukaryotic and prokaryotic pathways. Indeed, selective estrogen receptor modulators like 4-hydroxytamoxifen are capable of binding native estrogen receptors and exhibit crosstalk with the conserved Notch protein family[6]. Tetracyclines, although not derived from eukaryotic pathways, are a class of broadly used antibiotics and may present disruptive effects on the human microbiome[7,8]. This becomes especially relevant if a drug inducible system were to be applied for therapeutic applications or in microbiome studies. In recent studies, multiple groups found the efficacy of specific chemotherapeutics to be directly influenced by the gut microbiome[9-11]. Others have overcome these issues of crosstalk by using sub-toxic levels of ligands[12] or by using plant-derived CIPPs[13,14], but most existing inducible systems are still largely derived from eukaryotic or prokaryotic pathways.

For synthetic biology and therapeutic applications, an ideal ligand inducible system would be orthogonal to eukaryotic and prokaryotic biology, lowly present in the environment, versatile, tunable, and dynamic. To employ more orthogonal inducers and build upon the library of existing chemogenetic proteins, the ligand inducible connection (LInC) system and stabilizable polypeptide linkages (StaPLs) have been developed, which instead utilize Hepatitis C virus (HCV) cis-protease NS3 and its host of clinically tested antiviral drugs[15,16]. These systems permit control of transcription, protein localization, and cell signaling by utilizing highly specific and characterized ligands targeted against non-eukaryotic/prokaryotic targets. NS3 also possesses a large repertoire of inhibitor ligands. Due to the essential function of NS3 in viral replication, multiple approaches have been employed to develop NS3 inhibitor ligands, including genetically encodable approaches such as RNA aptamers and peptides[17,18].

Described herein is the control of protein function using catalytically inactivated NS3, genetically encoded antiviral peptides, and antiviral drugs. By utilizing genetically encodable peptides, the role of antiviral drugs can be extended to regulate peptide docking for control of protein-protein interactions, split enzyme complementation, and intramolecular inhibition. In this approach, genetically encoded peptides are used to spontaneously interact with their target NS3 protease but become competitively displaced upon the addition of a higher affinity drug.

Since NS3 in this context is solely serving as a high affinity binder instead of a severable linker, the protease no longer needs to be catalytically active. Although NS3 protease exhibits stringent substrate specificity[21], there are at least two endogenous cleavage sites involved in viral immune response[22,23], and some recently discovered promiscuity in cleavage sequence[24]. Throughout much of this work, NS3 proteolytical activity is ablated by mutating the catalytic serine to mitigate risk of off-target cleavage while maintaining affinity to peptides.

Results

Controlled transcription and cell signaling. High affinity antiviral peptides[18] were fused to the yeast Gal4 DNA-binding domain (Gal4$_{DB}$), and then a separate catalytically dead NS3s[139]A protease (dNS3) was fused to a transcriptional effector domain (FIG. 1A). In the absence of drug, the antiviral peptide and dNS3 are expected to spontaneously assemble to form a functional synthetic transcription factor. Upon the addition of a small molecule drug, dNS3 is expected to competitively bind to drug over peptide, therefore inhibiting activity of the transcriptional effector.

To mediate transcriptional activity, transcriptional activator VPR was fused to dNS3. In this configuration, spontaneous association between Gal4$_{DB}$-peptide and dNS3-VPR was expected to lead to transcriptional activation, and drug addition to lead to transcriptional shut-off. To validate this approach, Gal4$_{DB}$-peptide and dN53-VPR were transiently transfected and spontaneous transcriptional activation of genomically integrated, UAS-H2B-mCherry reporter observed (FIG. 1B). As concentration of NS3 inhibitor grazoprevir increased, dose dependent transcriptional inhibition was observed. Two peptides developed against NS3WT were tested—medium affinity CP5-46A-4D5E, and high affinity CP5-46-4D5E, referred to here as PMED and P$_{HI}$ respectively (FIG. 15).

Figure 5:
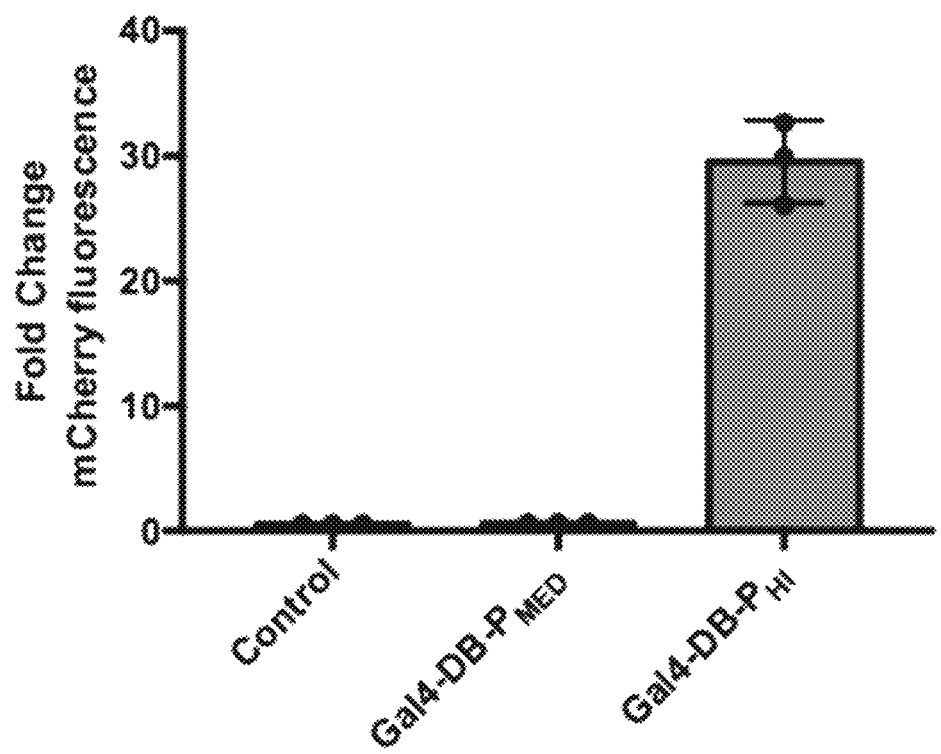
FIG. 5 demonstrates that Gal4$_{DB}$-P$_{HI}$ acts as a transcriptional activator. Transcriptional activation of UAS-H2B-mCherry via Gal4DB-PMED or Gal4DB-PHI without drug or dNS3-VPR compared to control of dNS3-VPR only. Plotted values are the mean±SD of biologically independent replicates, n=3.

Interestingly, P$_{HI}$ fused to Gal4$_{DB}$ acted as a transcriptional activation domain even in the absence of dNS3-VPR co-transfection, while Gal4$_{DB}$-Pm$_{ED}$ displayed no observable activation on its own (FIG. 5). Consequently, only PmED was used for the transcriptional effector work while P$_{HI}$ was reserved for non-transcriptional applications.

It was next predicted that the effector domain could be modular and control diverse transcriptional outputs. To test this, dNS3 was fused to transcriptional repressing domain KRAB to control transcriptional repression of constitutive reporter gene, UAS-CMV-H2B-Citrine (FIG. 1C). As expected, transcriptional repression occurred in the absence of drug, and the extent of repression could be controlled by concentration of grazoprevir.

These transcriptional effectors can also mediate processes where more than one type of stimuli is required for signaling. To demonstrate this, it was sought to apply drug-dependent transcriptional control in tandem with SynNotch cell signaling. SynNotch represents a highly modular approach to sense an extracellular ligand and trigger the release of an intracellular domain (ICD). In practice, it has been used to bind user-specified extracellular ligands, then trigger S2/S3 cleavage events to release customized transcription factor ICDs for genetic circuit and cancer therapeutic applications[25,26]. Each of these applications serve to benefit from increased control to create more complex gene circuits and safety switches for therapeutics. For these reasons the ICD of a previously developed Anti-GFP SynNotch[25] was replaced with Gal4$_{DB}$-Pm$_{ED}$ (FIG. 1D). In this arrangement, gene activation is controlled by extracellular ligand induced proteolysis and drug-controlled docking of dNS3-VPR, allowing for tight combinatorial control of ICD transcriptional activation of SynNotch.

Figures 6A, 6B, 6C:
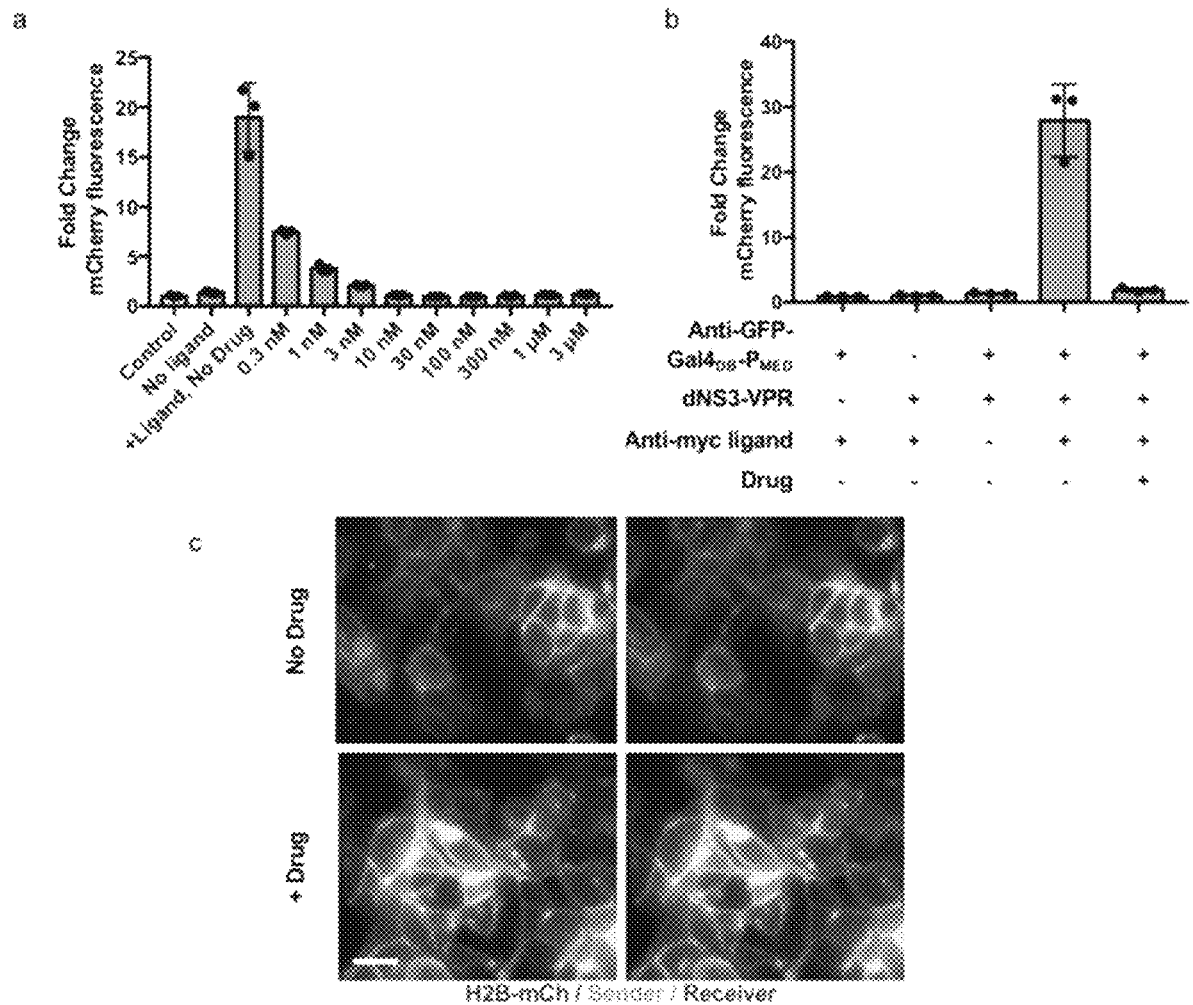
FIGS. 6A-6C demonstrate that SynNotch with a Gal4$_{DB}$-Pm$_{ED}$ ICD displays dose dependent activation and can respond to GFP or anti-myc ligand.

Cells containing the modified SynNotch constructs were grown on surfaces coated with GFP ligand in the presence of varying grazoprevir concentrations. When presented ligand in the absence of drug, cells exhibited UAS-H2B-mCherry reporter activation, while increasing concentration of drug led to dose-dependent transcriptional inhibition (FIG. 1E, FIG. 6A). Due to an extracellular c-Myc epitope tag, transcription could also be controlled by plated c-Myc antibody ligand (FIG. 6B). Small molecule control of SynNotch also extended to the context of intercellular signaling, which was tested by creating a GFP surface ligand "sender" cell line and then coculturing these cells with transiently transfected dNS3/peptide SynNotch "receiver" cells. Cocultured receiver cells exhibited drug-dependent transcriptional turn-off when presented GFP ligand (FIG. 1F, FIG. 6C).

Figure 2A:
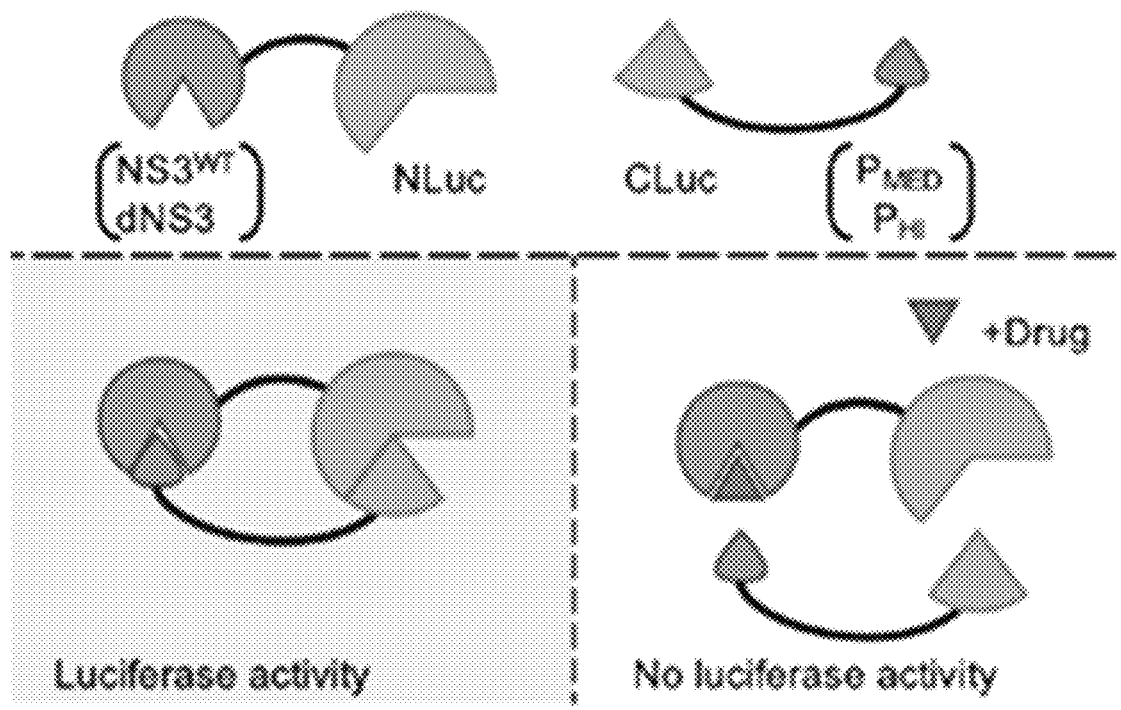
FIGS. 2A-2E depict split Luciferase control and characterization (FIG. 2A) Design of split luciferase constructs. NLuc(12-1247) was fused to dNS3 or NS3WT. CLuc(1200-1643) was fused to PMED or PHI peptide.

Controlled enzymatic activity by split protein complementation. Since dNS3 and its high affinity peptides effectively regulated assembly of a split transcription factor, it was surmised that dNS3/peptide complementation could control assembly of split enzymes. To test this, permutations of dNS3, NS3wT and each peptide variant were fused to split fragments of *Renilla* luciferase (FIG. 2A). Controlled assembly of split luciferase not only demonstrates enzymatic control, but it can also be used to compare binding characteristics of each permutation.

Figure 2B:
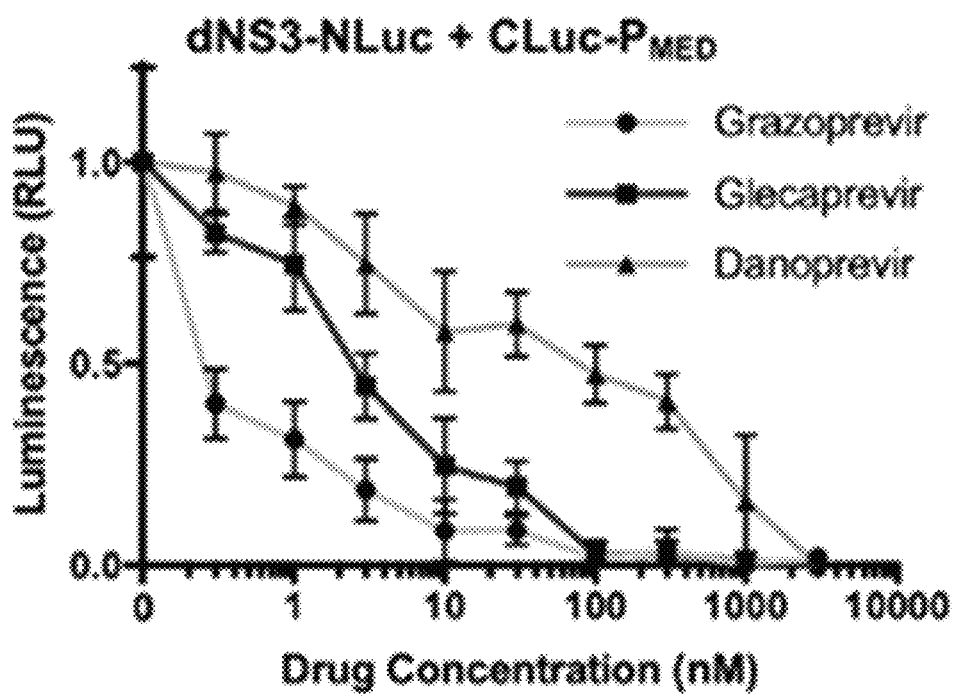
Figure 7:
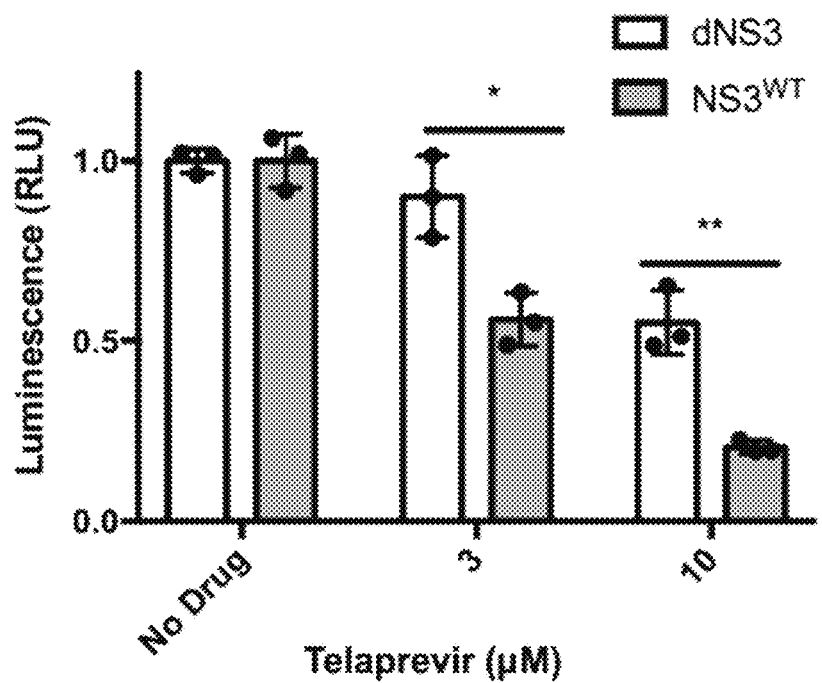
FIG. 7 depicts a graph of differential displacement profiles of dNS3 and NS3wr with Telaprevir. Drug response of split dNS3-NLuc, NS3wT-NLuc and CLuc-PMED with telaprevir. Dose response are normalized to their respective no drug controls. All cells were transfected 48 hours before lysing for luciferase experiments, and drug was added at the time of transfection. Plotted values are the mean±SD of biologically independent replicates, n=3, *P<0.05, **P<0.005.

The previously identified pair of dNS3 and PmED was used as the first model peptide docking pair and luciferase activity in transfected HEK293FT lysates tested upon addition of four different drugs: grazoprevir, glecaprevir, danoprevir, and telaprevir (FIG. 2B, FIG. 7). The first three of these drugs inhibit luciferase activity in a dose dependent manner, representing multiple modes of inhibition with distinct binding profiles. Interestingly, split luciferase constructs containing dNS3 exhibit significant resistance to Telaprevir. This observation is consistent with the drug's covalent binding mechanism to the catalytic Ser139[27,28] which is mutated in dNS3, and this effect is reverted upon replacement with wild-type NS3 (FIG. 7).

Figure 2C:
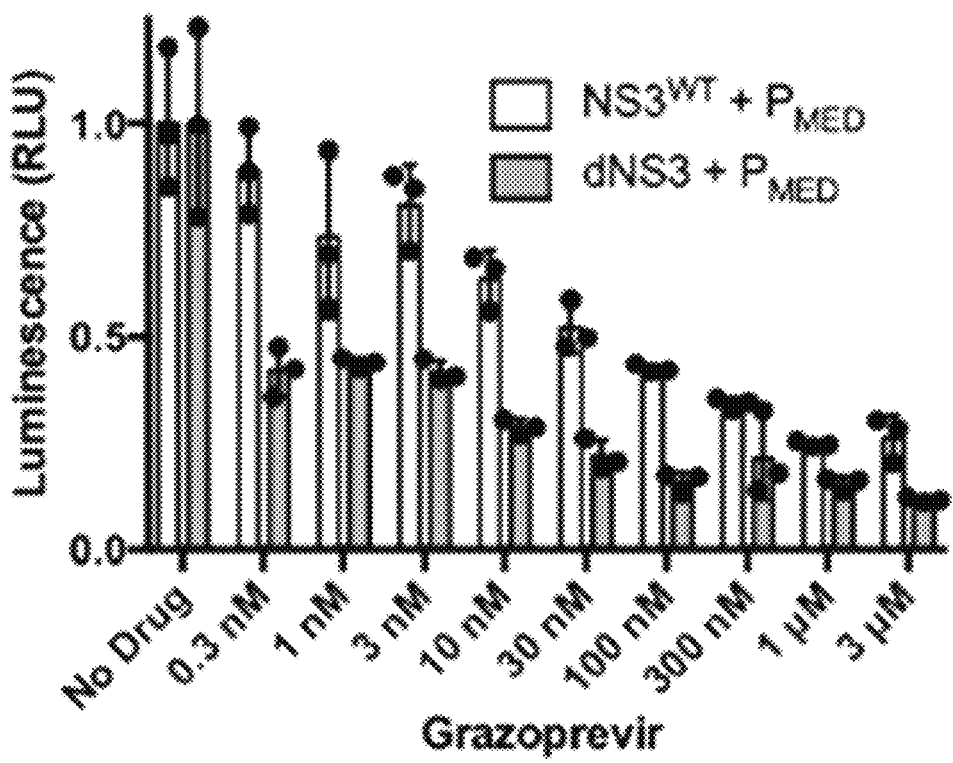
Figure 2D:
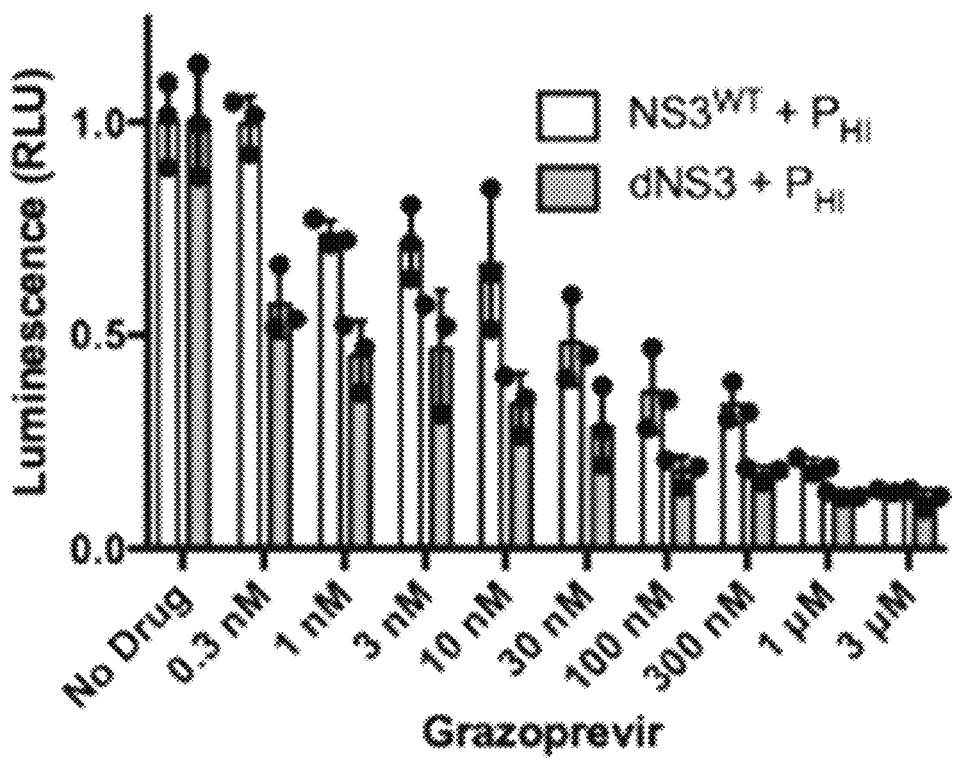
Figures 8A, 8B:
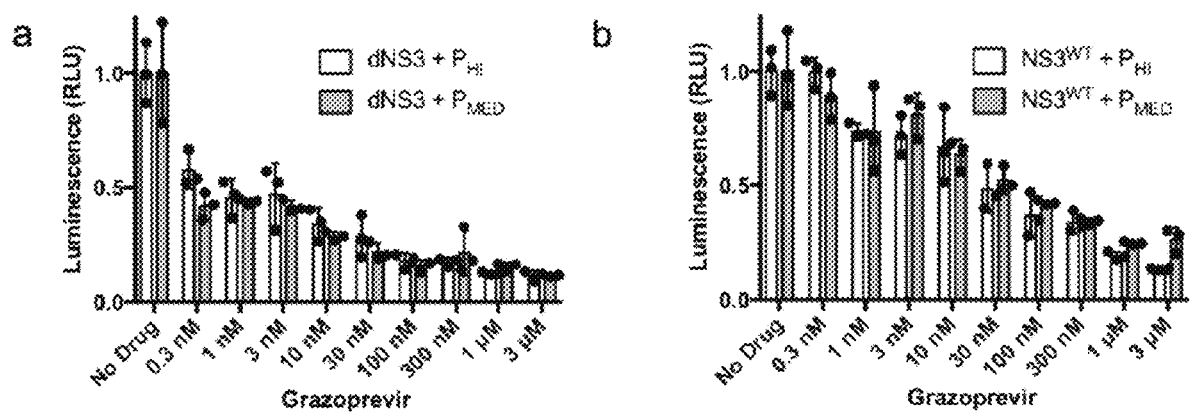
FIGS. 8A-8B depict a comparison of drug mediated displacement with P$_{MED}$ vs. PHI.

Since NS3's catalytic serine residue can effect binding characteristics, both NS3WT and dNS3 were tested with P$_{MED}$ and P$_{HI}$ peptides as fusions to split luciferase subunits. All permutations of these constructs were functionally sensitive to the range of grazoprevir concentrations tested. Notably, the split luciferase heteromerized by dNS3 displays slightly increased sensitivity to drug than NS3WT does (FIGS. 2C, 2D), possibly due to the loss of a hydrogen bond between the peptides and NS3 as a result of the S139A mutation. However, the affinity differences of the two peptides tested did not seem to make a substantial difference in dose response to grazoprevir at the concentrations tested (FIG. 8A, 8B).

Figure 2E:
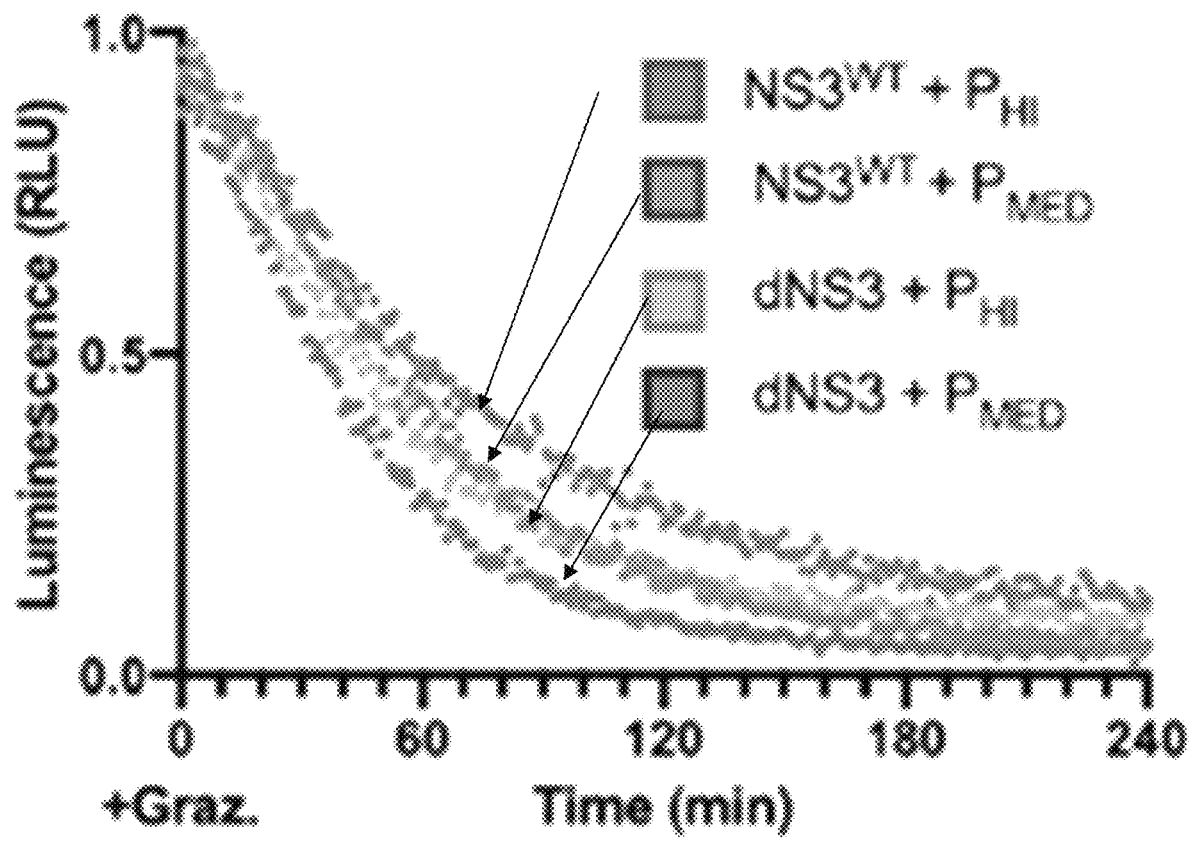
Figures 9A, 9B:
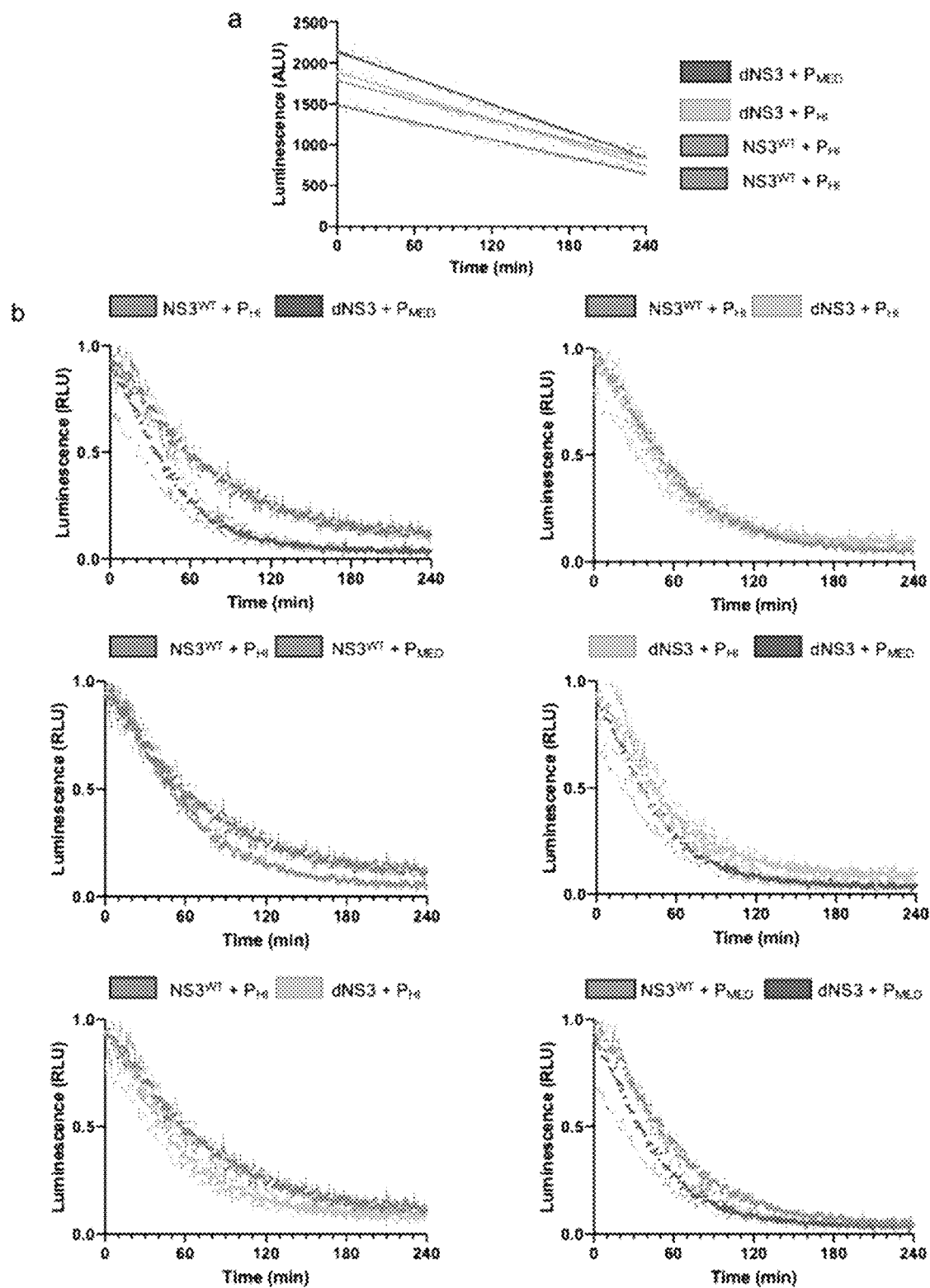
FIGS. 9A-9B depict the kinetics of displacement for various combinations of NS3wT, dNS3, and PMED and PHI.
Figure 10A:
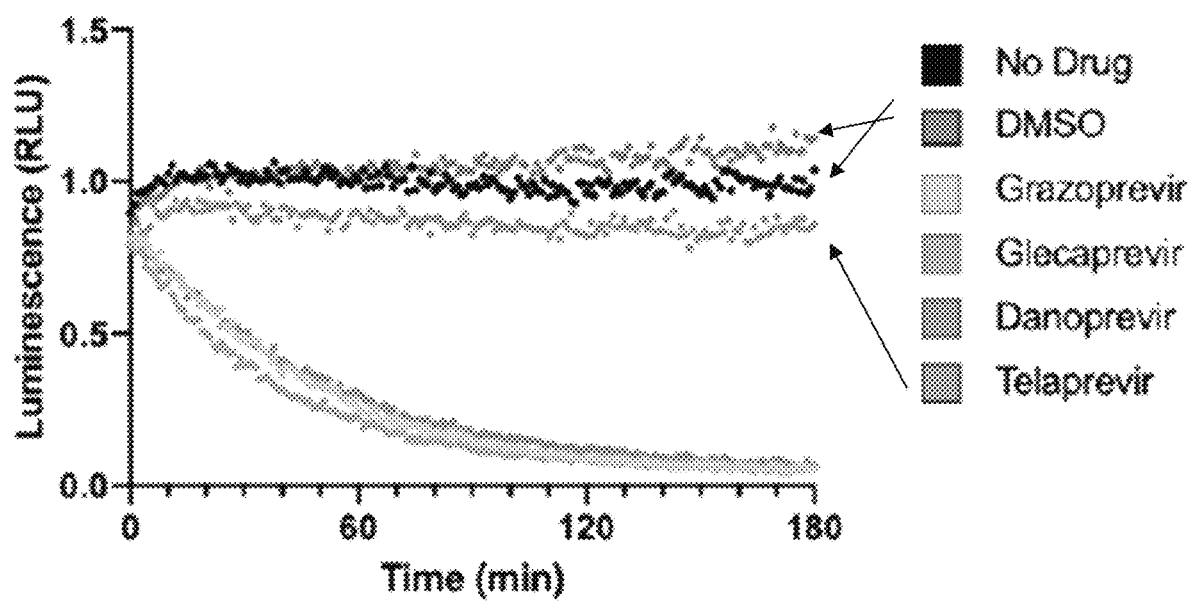
FIGS. 10A-10B depict temporal response of dNS3-NLuc and CLuc-PmED to various drugs.
Figure 10B:
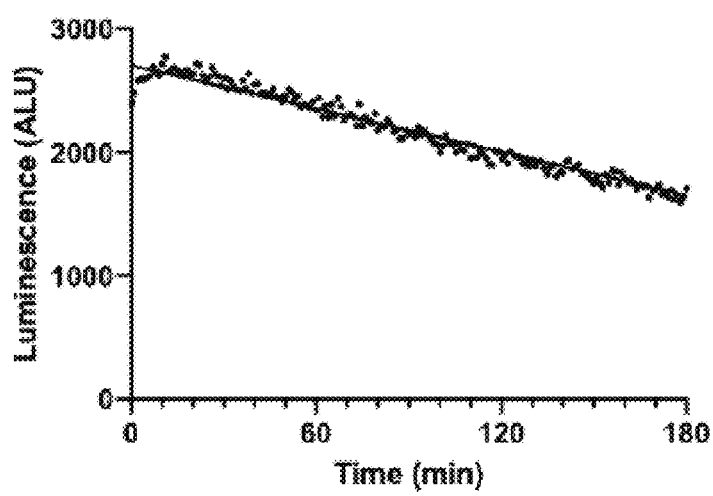

Next, the temporal displacement of peptide was demonstrated by taking advantage of the reversibility of split luciferase complementation. Temporal dissociation of proteins is important for many biological processes and is often desired for dynamic gene expression. Kinetics of displacement were measured over a four-hour period with excess drug concentration and normalized to their respective no drug controls (FIG. 2E, FIGS. 9A-9B). In this configuration, the fusions of dNS3 and P$_{MED}$ to split luciferase yielded the fastest displacement kinetics, with luciferase activity reduced to half maximal activity at ~30 minutes. The replacement of dNS3 with NS3' or the replacement of P$_{MD}$ with P$_{HI}$ increased the time to displacement, reflecting expected increases in protein-peptide affinity. Following peptide and NS3 variations, multiple drugs were tested with dNS3 and P$_{MED}$ (FIGS. 10A-10B), but little difference in dissociation rate occurred at saturating drug concentrations aside from telaprevir, which did not dissociate dNS3-P$_{MED}$ complexes well. Altogether, the classes of previously developed peptides and small molecules allow for variation of binding kinetics and dose responses with multiple antiviral drugs. Temporal experiments additionally reveal that antiviral drugs can disrupt preformed protein-peptide complexes.

Controlled genetic recombination through intramolecular inhibition. In native biology, enzymes are routinely controlled by allosteric mechanisms. Synthetic protein allostery is advantageous in a biological tool because it offers a self-encoded mechanism of control, which can increase its applicability across organisms. It was next sought to allosterically control enzyme activity via dNS3 and inhibitory peptide.

For this application, Cre recombinase exemplifies a widely-used enzyme that often requires ligand control. Cre recombinase is a site specific, DNA recombinase that has been traditionally controlled by conditional nuclear translocation via 4-hydroxytamoxifen[4] or various split protein complementations[29]. Yet, Cre is commonly used in developmental biology studies, which often require genetically small constructs for viral incorporation and orthogonal inducer ligands that are lowly present in the environment. To overcome these limitations, a single construct was envisioned, drug inducible Cre controlled by antiviral drugs. Cre is a tyrosine recombinase, and since there were no available unbound Cre structures, the structure of bound Cre (FIG. 3A) was compared to related unbound and bound tyrosine recombinases such as XerA and XerD[30,31].

Figure 3B:
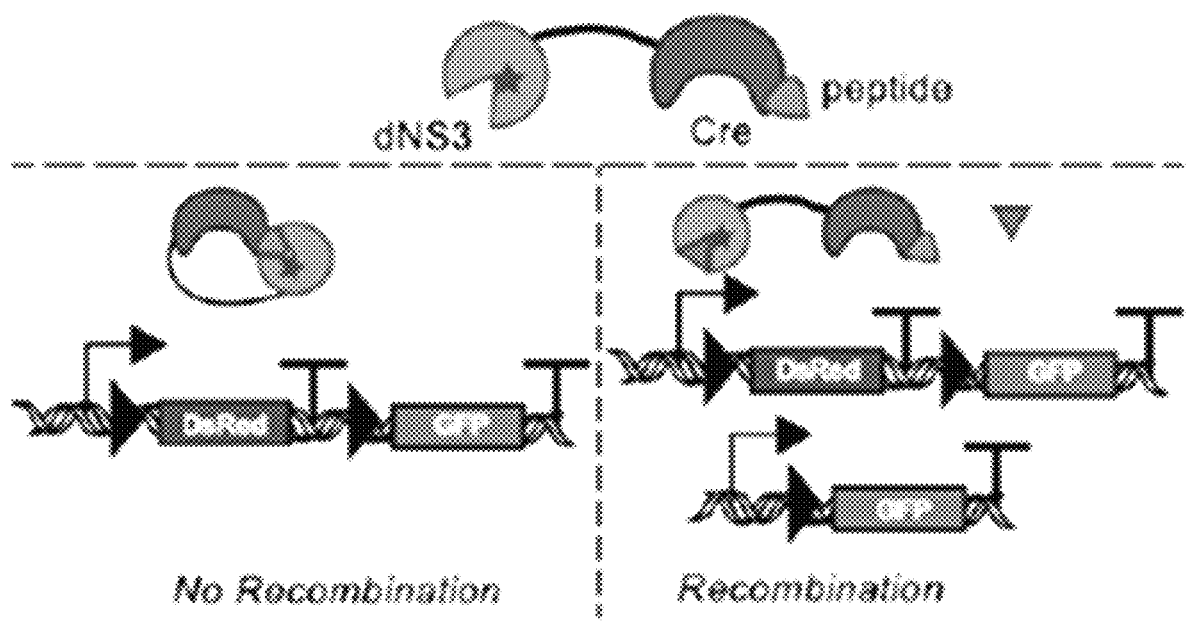
Figure 3C:
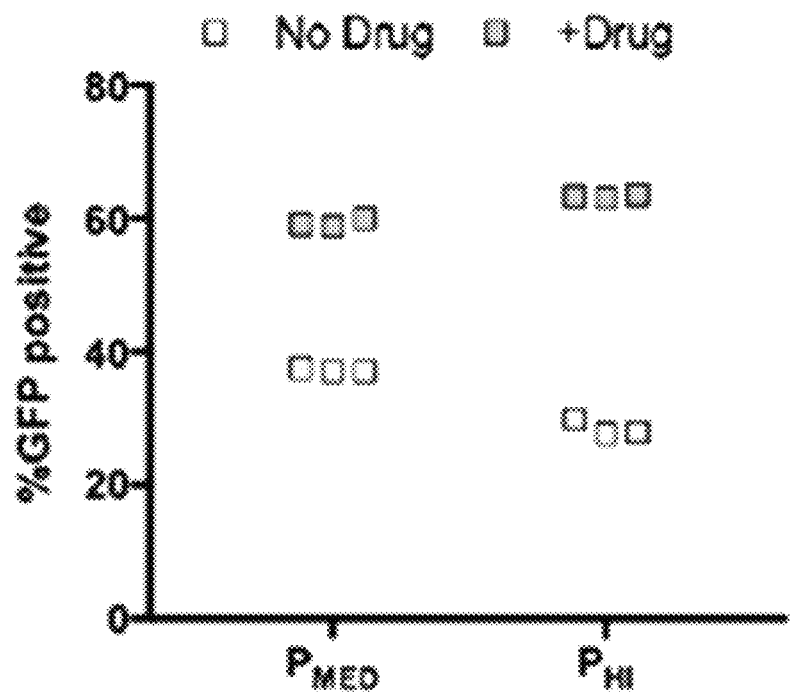

Comparisons reveal that each of these tyrosine recombinases forms a C-shaped clamp composed of two domains, separated by a flexible linker. Hence, it was inferred that Cre undergoes a large conformational change to regulate DNA cleavage and hypothesized that the fusion of dNS3 and inhibitory peptide at opposing termini of Cre could result in drug controlled intramolecular occlusion of the enzyme (FIG. 3B). To measure drug inducible dNS3-Cre-peptide recombination, all constructs were tested in a clonal Cre-stoplight reporter HEK293FT cell line. Initial testing with P$_{mED}$ peptide revealed promising results, and dynamic range improved with replacement of P$_{mED}$ with higher affinity P$_{HI}$ (FIG. 3C).

Figure 3D:
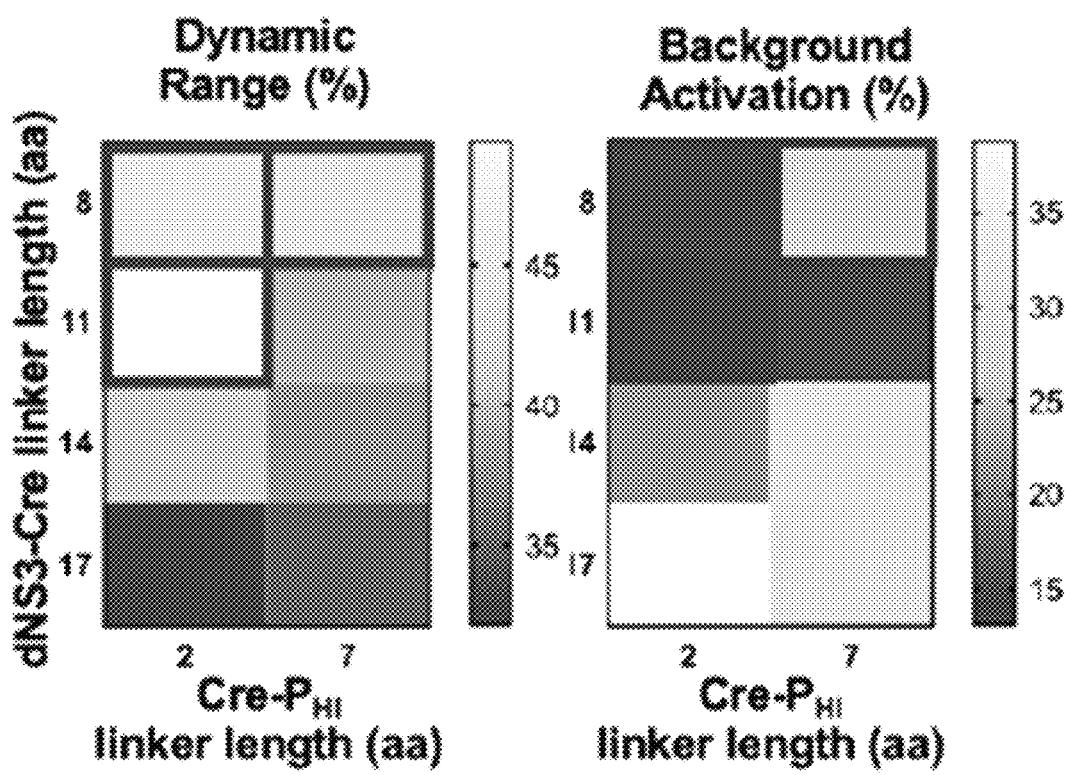
Figure 3E:
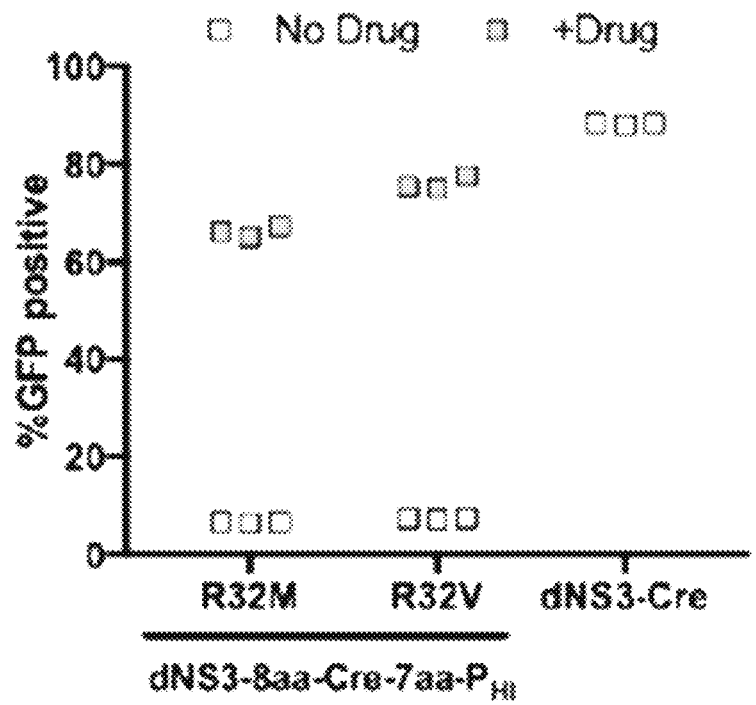

Recombination affects gene expression of the GFP in a step-like fashion, making it crucial to achieve background recombination in an inducible tool. Following substitution of P$_{mED}$ with P$_{HI}$, further optimization was undertaken, for lower background while retaining high dynamic range. To further reduce basal recombination, glycine-serine linker length was varied between the N-terminal fusion of dNS3 to Cre and between the C-terminal fusion of $P_{HI}$ to Cre (FIG. 3D). From the linker variations tested, three candidates were chosen with high dynamic range of activation upon grazoprevir addition and low background activation in absence of drug (FIG. 3D, boxed).

Figures 11A, 11B, 11C, 11D:
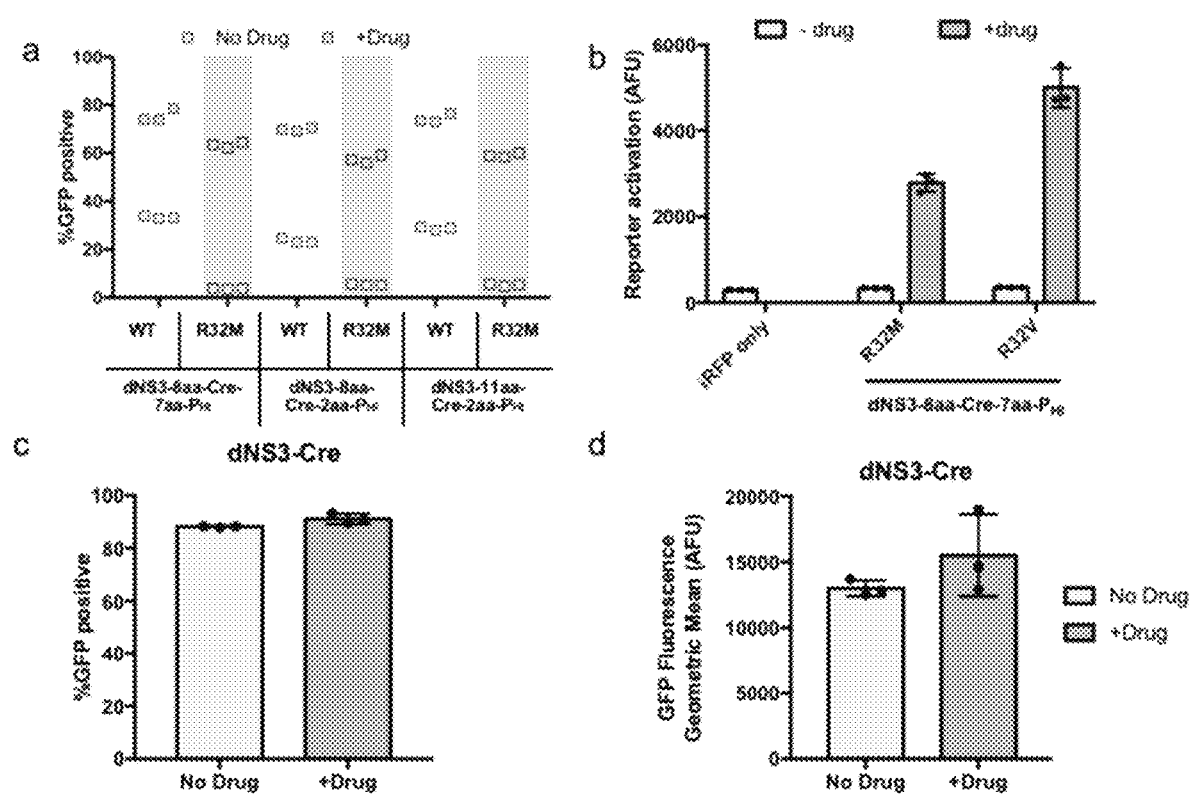
FIGS. 11A-11D demonstrate the effects of R32 mutations on various Cre constructs and geometric mean of GFP activation by Cre recombinase.

However, significant background remained in the three selected linker variants, leaving room for further optimization. It was hypothesized that some intramolecular dNS3 and $P_{HI}$ interactions were spontaneously active, subsequently allowing these Cre molecules to cooperatively dimerize through native Cre termini interactions[32,33]. To mitigate cooperativity and decrease background, the Cre R32 site, which is thought to decrease cooperativity and shown to increase recombination accuracy[34] was mutated. The $Cre^{R32M}$ mutation caused considerable decrease in background for all dNS3-Cre-$P_{HI}$ constructs tested in transient transfection driven by a strong CAG promoter (FIG. 11A), and linker variant dNS3-8aa-$CreR^{32}M$-7aa-$P_{HI}$ provided optimally low background recombination and high dynamic range. This linker variant exhibited favorable properties with either $Cre^{32}M$ or similarly reported $Cre^{R32V}$ mutation, indicating that this mutation site provides minimal background our drug inducible Cre in addition to previously characterized higher accuracy of recombination (FIG. 3E, FIG. 11B-11D). Each of these final inducible Cre constructs activated a similar fraction of cells compared to their Cre' counterparts, while the dNS3-Cre' control remained constitutively active (FIGS. 11C-11D).

Figure 3F:
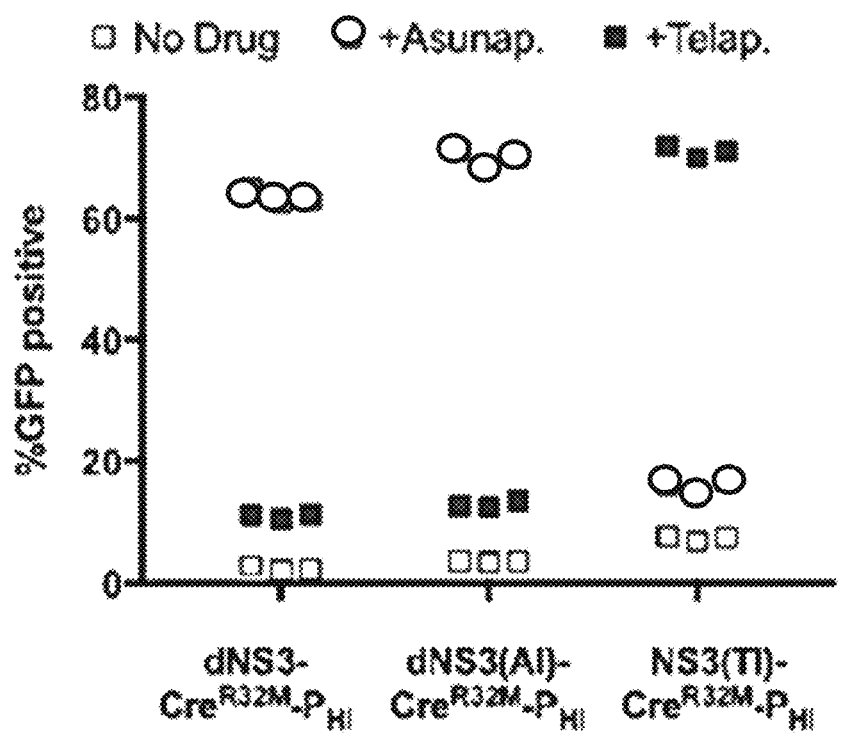
Figure 12A:
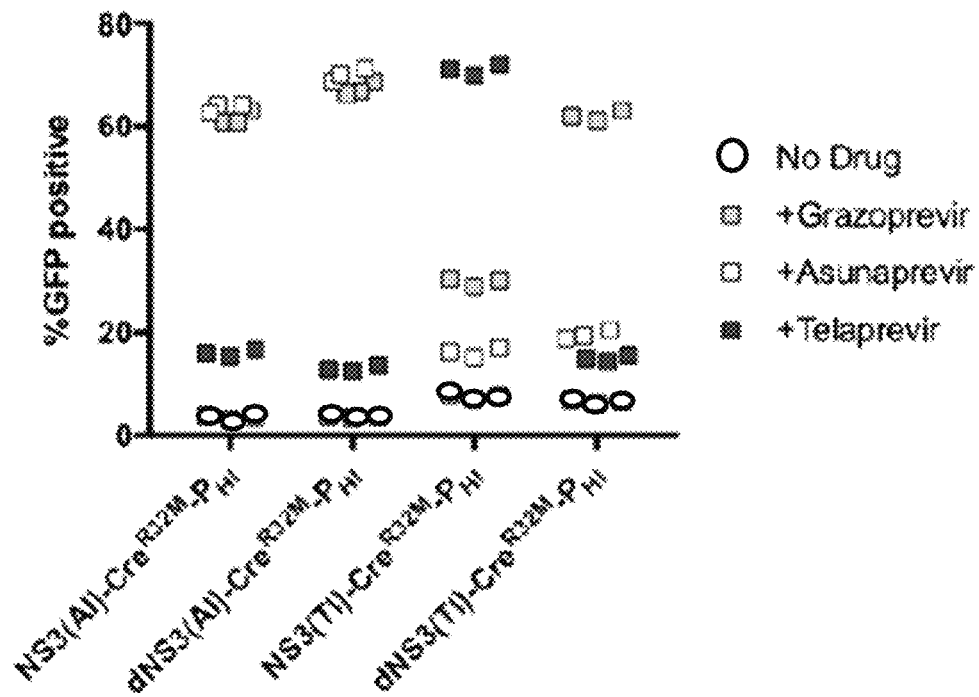
FIGS. 12A-12B demonstrate the effect of S139 mutations in drug resistant inducible Cre and geometric mean of GFP activation by drug resistant Cre recombinases.
Figure 12B:
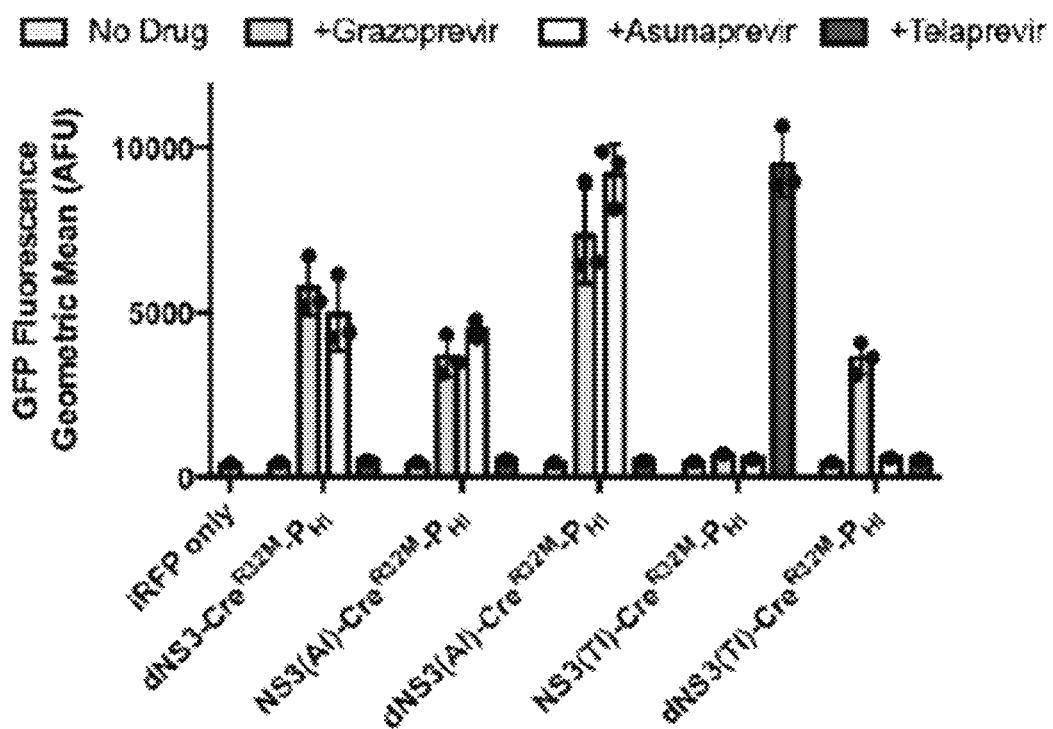

Equipped with an optimized inducible Cre system, opportunities to control genetic recombination were explored in two different cell populations to reflect the higher complexity of gene expression in specific cell lineages. To accomplish this, it was sought to make orthogonal inducible Cre recombinases. Specific NS3 mutations can create drug resistant orthogonal protease pairs that are asunaprevir inducible (AI) or telaprevir inducible (TI)[16]. Introducing these protease mutants into our peptide-based inducible Cre system led to anew pair of orthogonal Cre constructs that strongly induced via asunaprevir or telaprevir with low background recombination (FIG. 3F and FIGS. 12A-12B). Alternatively, the original catalytic $NS3s^{139}A$ mutation is also sufficient on its own to reduce telaprevir sensitivity while retaining asunaprevir induction (FIG. 3F), consistent with previous experimental results (FIG. 7). Applying the $NS3s^{139}A$ mutation to the NS3(TI) similarly ablates telaprevir sensitivity, leaving only sensitivity to grazoprevir among the three drugs tested here. Collectively, these inducible Cre recombinases have the ability to strongly respond to two distinct antiviral drugs and also demonstrate a mechanism of covalent ligand control of enzymatic activity that can be reversed with catalytically inactive NS3.

Figure 4A:
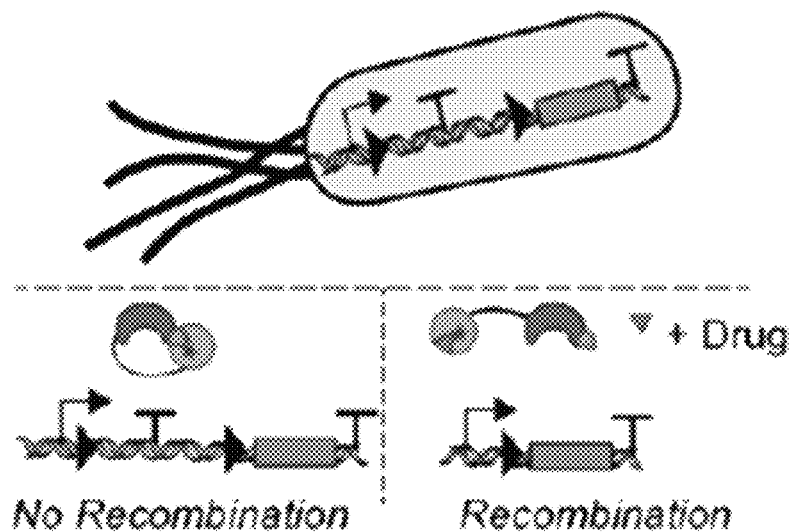
FIGS. 4A-4C depict drug control of genetic recombination in prokaryotes (FIG. 4) Genetic recombination in prokaryotes. To report on Cre mediated recombination, a transcriptional terminator is located after a constitutive promoter and excised by Cre recombination.
Figure 4B:
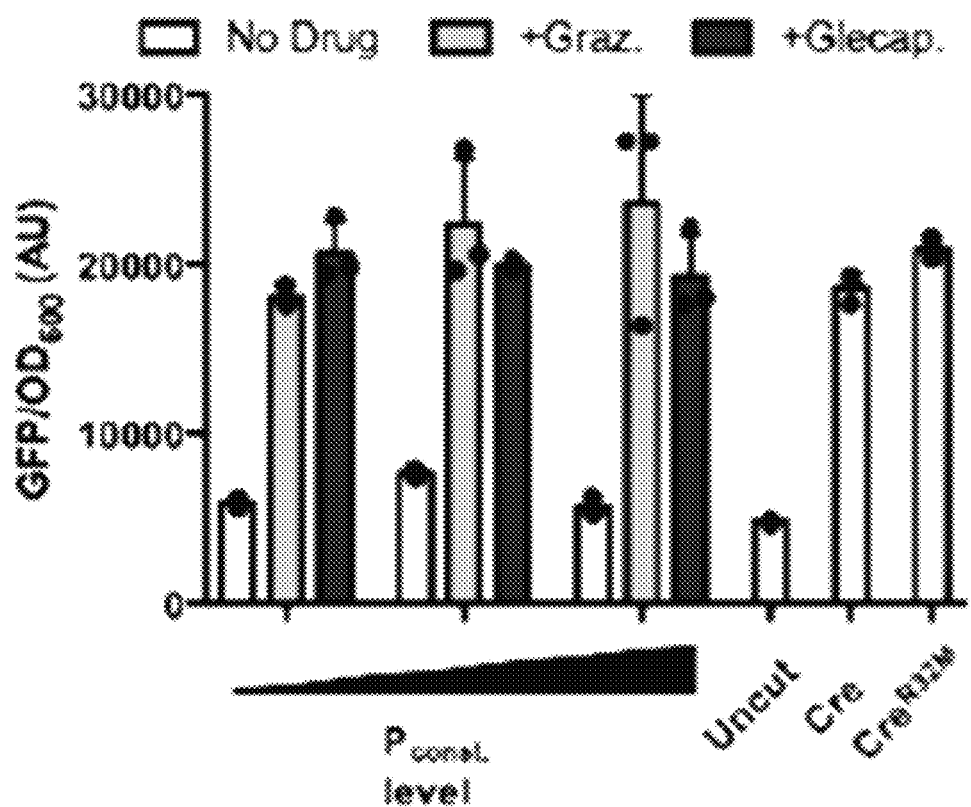
Figure 4C:
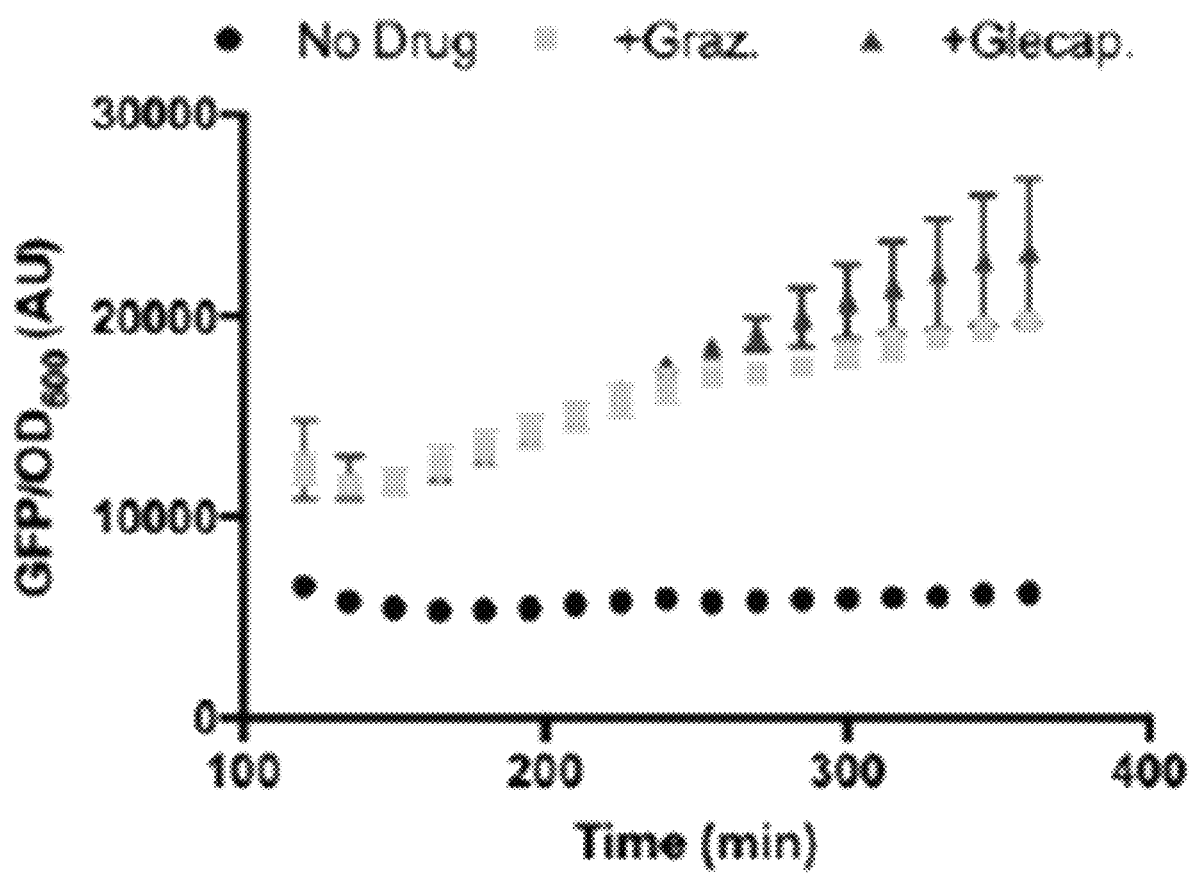
Figure 13A:
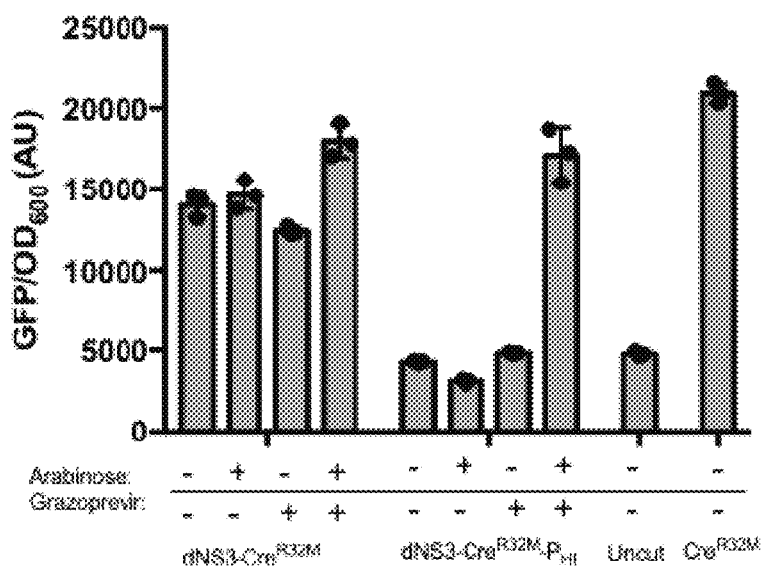
FIGS. 13A-13C demonstrate the activation of Cre reporter with Cres under arabinose promoters and antiviral drug effect on bacterial growth.
Figure 13B:
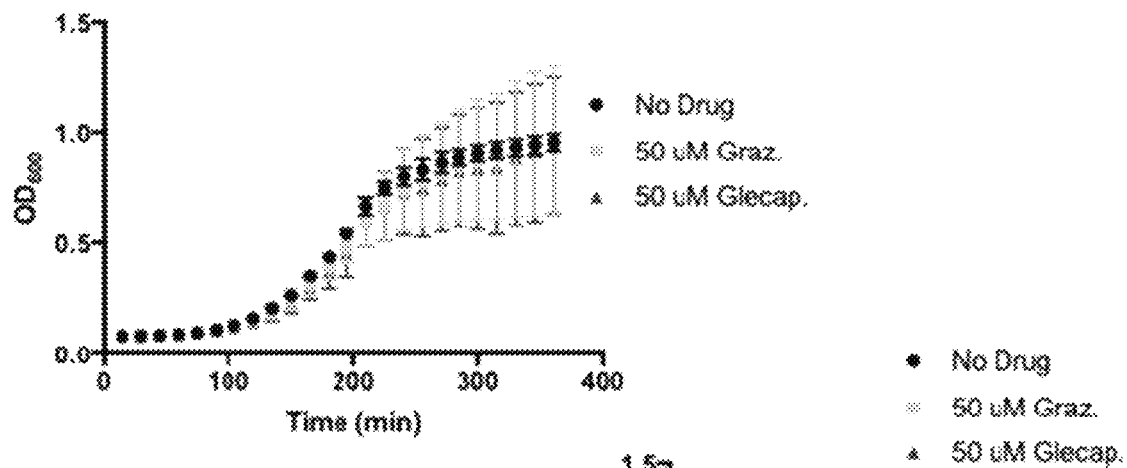
Figure 13C:
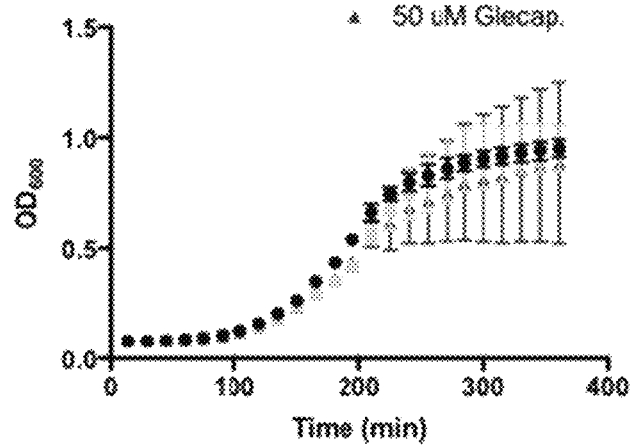
Figure 14:
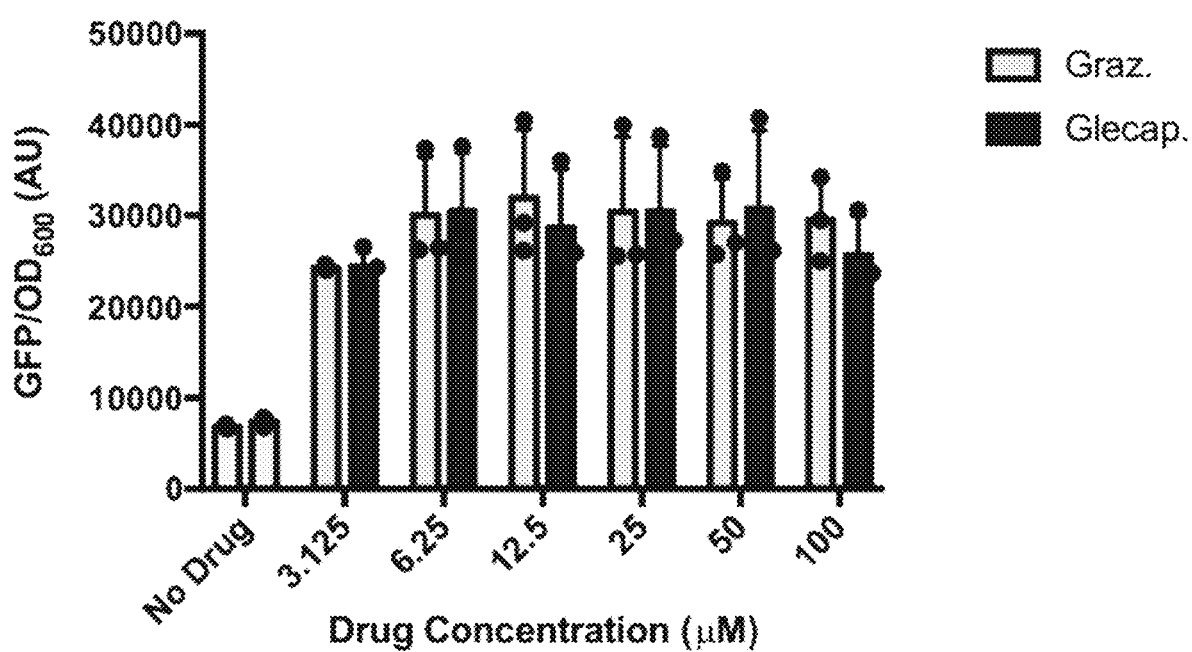
FIG. 14 depicts a graph of the dose response of dNS3-CreR32M-PHI in bacteria. Inducible dNS3-CreR32M-PHI was expressed under the weakest constitutive promoter in FIG. 4B, six hours post-drug addition, fluorescence/OD quantified by plate reader. Plotted values are the mean±SD of biological replicates, n=3.

Since the engineered control mechanism of Cre does not rely on nuclear translocation and instead relies on allosteric control (data not shown), it was expected that antiviral drug inducible Cre would readily translate across organisms and function in prokaryotes. To test this, dNS3-$CreR^3 2M$-$P_{HI}$ and GFP Cre reporter were co-transformed into E. coli (FIG. 4A). Cre constructs were expressed at a constant level under an arabinose inducible promoter (FIG. 13A) or under a broad range of constitutive promoters of varying strength (FIG. 4B, FIG. 16). Upon induction with antiviral drugs, GFP expression significantly increased, with detectable GFP expression occurring at <120 min under a constitutive promoter (FIG. 4C) and no significant change to bacterial growth (FIGS. 13B, 13C). Minimal background recombination via dNS3-$CreR^3 2M$-$P_{HI}$ presented in the absence of drug, while in contrast, both dNS3-$Cre^{R32M}$ lacking inhibitory peptide and $Cre^{R32M}$ exhibited substantial recombination. The dNS3-$Cre^{R32M}$ and $Cre^{R32M}$ background recombination could not be remedied even under an uninduced, arabinose-driven promoter (FIG. 13A). Interestingly, drug concentrations of antiviral drug inducible Cre needed to be increased from the levels used in mammalian cells, consistent with previous literature utilizing HCV NS3 in bacteria[35]. Nevertheless, maximal recombination occurred as low as 6.25 µM of glecaprevir or grazoprevir (Supp. FIG. 11). This represents the first drug inducible Cre in bacterial systems, highlighting the versatility of intramolecular inhibition via dNS3 peptide pairs. Overall, this tool permits drug inducible recombination in prokaryotic cells and mammalian cells with chemical inducers that are lowly toxic to both cell types.

Discussion

Demonstrated herein are diverse controls over protein activity via dNS3 and genetically encoded inhibitory peptides. To this end, regulation is shown of transcriptional complex formations, cell signaling, spontaneous association of split-luciferase and its associated enzymatic activity, and lastly the genetic recombinase Cre using antiviral inhibitors. Demonstrated herein is antiviral drug regulation of transcriptional complex formations, cell signaling, spontaneous association and drug-mediated dissociation of split enzyme domains, and synthetic allostery of Cre recombinase.

Analysis of peptide binding characteristics revealed tunable and dynamic control of protein-protein interaction, and this system can respond to a myriad of different drugs. Dose responses of these systems can also be tuned via swapping genetic parts such as peptides, alternate forms of NS3, or by the specific drug used. These features underscore the benefits to using a highly characterized target such as NS3 as synthetic tool. Due to the diversity of approaches to target NS3, high affinity, bioavailable small molecule drugs can be paired with alternate inhibitors such as genetically encoded peptides. This effort proves to be ongoing, with FDA approvals of molecules such as glecaprevir as recently as 2017, providing researchers a continually expanding toolkit to control these protein tools synthetically.

Alongside efforts to demonstrate versatility of NS3 and its associated inhibitors, described herein is an allosterically controlled recombinase through Cre structure-guided design. This system displayed the ideal characteristics of low background recombination and high dynamic range in a recombinase while utilizing orthogonal ligands and a single optimized protein. Extensive clinical efforts to develop NS3 inhibition led to expanding the repertoire of Cre recombinase tools as well. Drug-resistant NS3 mutants were utilized to control peptide binding with two orthogonal, FDA approved inhibitors.

Lastly, allosterically controlled Cre was easily transferred across domains of life to function in E. coli. The applicability in E. coli combined with minimal toxicity to prokaryotic and eukaryotic hosts opens up greater possibilities of studying causal roles of microbiome gene expression in vivo as well as benchtop bacterial processes. As a whole, NS3 and its associated inhibitors represent an exciting toolkit to control protein activity in a more orthogonal manner to eukaryotic and prokaryotic organisms.

Methods

DNA Constructs. Standard procedures of ligation and Gibson assembly were applied to all constructs created for this paper, and detailed sequence information can be found on Addgene. See, e.g. the Cre reporter plasmid (Addgene #62732), the eGFP-pBAD plasmid (Addgene #54762), and the pmiRFP670-N1plasmid (Addgene #79987). Detailed plasmid information can be found and requested for on Addgene.

Mammalian cell culture. HEK239FT cells were purchased from Thermo Fisher and maintained in a 37° C. incubator supplemented with 5% CO2. Cells were cultured in DMEM with 10% FBS and supplemented with non-essential amino acids (Life Technologies) and Glutamax (Life Technologies). For UAS-H2B-mCherry experiments, a clonal cell line was previously created via random plasmid insertion and serial dilution to select single colonies. Cells were selected for with Zeocin resistance (100 vg/mL, Invivogen). For generation of a Cre reporter line, the lentiviral Cre reporter plasmid (62732) was modified to have Blasticidin resistance. This construct was then virally transduced and selected for with Blasticidin (10 vg/mL, Invivogen) and clonally selected by serial dilution.

DNA transfections and NS3 inhibitors. All DNA transfections were carried out using Lipofectamine 3000 (Thermo Fisher) according to the manufacturer's instructions. All transcriptional effector experiments were carried out at a mass ratio between 1:2 and 1:3 of Gal4DB constructs to transcriptional effector. For imaging experiments, fibronectin (Product #F1141, Sigma-Aldrich) was seeded on to glass coverslip substrate at a dilution of 5 vg/mL for one hour at room temperature and rinsed three times with PBS before seeding cells. All other experiments were carried out on tissue cultured treated plastic (Corning) or for cell adherence by manufacturer (ibiTreat by Ibidi).

Drug was either added at time of transfection or 24 hours later. Grazoprevir, danoprevir, and glecaprevir were all purchased from MedChemExpress. All stocks were diluted between 3-10 mM stock concentrations in DMSO.

Protein Purification. GFP SynNotch ligand was expressed and purified from E. coli DH10B cells (Thermo Fisher). E. coli were transformed with arabinose inducible EGFP-pBAD plasmid (Addgene #54762) overnight at 37° C. The following day, the bacterial culture was diluted 1:50 into 0.5 L of LB and induced at an OD600 of 0.8 with 0.02% arabinose for 24 hours at 25° C. After induction, bacteria were pelleted at 3000 rcf and purified following the QiaExpress Ni-NTA Fast Start protein purification protocol (Qiagen, Catalog #30600) under native conditions.

Ligand coating and coculture for SynNotch experiments. For plated ligand experiments, untreated tissue culture plastic was incubated with purified GFP ligand or c-Myc Monoclonal Antibody (Invitrogen 9E10.3, Catalog #AH00062) in PBS for one hour at room temperature. Plates were subsequently washed three times with PBS prior to before adding transfected cells and drug mixed in cell culture media.

For coculture experiments, sender cells were virally transduced with constitutive surface presenting GFP-ligand and allowed to grow for two days. Lentivirus was prepared via transient transduction of GFP-ligand construct, VSVG and PAX2 packaging plasmids for 6-12 hours before removing transfection media. After 24 hours and 48 hours, media was collected and replaced. The supernatant was then filtered with 0.45 I.LM sterile filters (Whatman, Catalog #6780-2504). Suspended cells were then transduced with viral media for 48 hours before proceeding with coculture. iRFP670 labeled receiver cells were transiently transfected with SynNotch constructs 24 hours prior to coculture. Cells were added at ratios between 1:4 and 1:10 receiver cells to sender cells and cultured for 24 hours before fixation in 4% paraformaldehyde.

Flow cytometry. Cells were analyzed by flow cytometry in suspension on an Attune NxT flow cytometer (Thermo Fisher) and analyzed by Flowio (v10). Live cells were gated by forward and side scatter detection. Of the live cells, populations were gated for fluorescently positive if their fluorescence intensity was greater than or equal to the top 1% of non-transfected cells. For Gal4-DB-peptide and N53-transcription effector experiments, a ratio of 1:2 molar ratio of DNA binding domain to transcriptional effector was used. A co-transfection marker of a constitutively expressed protein, mTurq2, was used and cells were deemed positively transfected if they were mTurq2 fluorescently positive. Hereafter, the geometric mean of reporter UAS-H2B-mCherry (dNS3-VPR experiments) or UAS-CMV-H2B-Citrine (dNS3-KRAB experiments) was measured and normalized to a control.

For Cre recombinase control in mammalian cells, live cells were gated in the same manner as above and gated for transfection by either a co-transfection marker of pmiRFP670-N1 or inter-plasmidic constitutive expression of iRFP670 under a separate constitutive promoter. Cells were further deemed as GFP positive if their fluorescence intensity was greater than or equal to the top 1% of non-transfected cells. Baseline activation of GFP positive cells was then subtracted using transfection marker only cells as baseline for all measurements.

Luciferase assay. HEK293FT cells were transfected with split luciferase constructs. In the case of drug pretreatment for dose curve experiments, drug was added at the indicated concentration at the time of transfection. Two days later, the transfected cells were lysed with 1×Ex Luciferase Assay Buffer using the Nano-Glo® Dual-Luciferase® Reporter Assay System (Promega). Immediately after, the samples were treated with an additional volume of 1×Ex Luciferase Assay Buffer with the indicated concentration of drug.

The samples were then read with a plate reader once per minute measuring luminescence with 500 millisecond exposure time. Samples which had not been incubated in drug had decreased luminescence over time, corresponding to utilization of the luciferase reagents. For kinetics analysis, linear regression analysis was performed on the untreated samples and used to normalize the data for the treated samples.

Bacterial cell culture. E. coli strain BW25113 was used for all bacterial experiments. Drug inducible Cre expression plasmids were derived from the low copy (SC101) plasmid pBbS8c from Lee et al.[36]. For readout of Cre recombination, a transcriptional terminator flanked by LoxP sites was located between a constitutive promoter and superfolder GFP (sfGFP). The terminator is excised upon recombination, allowing transcription of sfGFP. Cells were transformed and inoculated in 3 mL LB with 25 µg/mL chloramphenicol and 30 vg/mL kanamycin for Cre expression and reporter plasmid maintenance, respectively. Cells were grown at 37° C. In the case of arabinose inducible constructs (FIGS. 13A-13C), cultures were pre-treated with 1 mM arabinose for 2 hours prior to drug treatment when appropriate. Experiments were carried out in clear 96-well plates with cell cultures diluted 1:100 into a culture volume of 200 µL. OD600 and fluorescence were measured in a BioTek Synergy H1 plate reader after 6 hours of drug treatment. For sfGFP detection, excitation and emission wavelengths of 480 nm and 510 nm were used, respectively.

Image acquisition and analysis. To prepare cells for imaging, transfected cells in ibiTreat 8-wells (iBidi) were fixed in 4% paraformaldehyde (Thermo Fisher) diluted in PBS for less than or equal to ten minutes, followed by three rinses with PBS, and then quenching with 5% BSA. Fixed cells were maintained and imaged in PBS.

Images were acquired with epifluorescence using a Zeiss AxioObserver.Z1 microscope and Zen software (Zeiss). Representative images were taken and processed in ImageJ-based image analysis package Fiji.

Statistics. All statistical analyses for flow cytometry were performed in Prism (v7.04) using three independent biological replicates. For imaging conditions 3 images were taken per condition and representative images were selected. Statistical significance was determined via standard t-tests in Excel. For temporal luciferase experiments, linear regressions were also performed in Prism (v7.04) using three independent biological replicates.

Work Cited

1. Spencer, D. M., Wandless, T. J., Schreiber, S. L. & Crabtree, G. R. Controlling signal transduction with synthetic ligands. *Tanpakushitsu Kakusan Koso.* 262, 1794-5 (1993).
2. Trost, M., Blattner, A. C. & Lehner, C. F. Regulated protein depletion by the auxin-inducible degradation system in *Drosophila melanogaster. Fly (Austin).* 10, 35-46 (2016).
3. Boncompain, G. et al. Synchronization of secretory protein traffic in populations of cells. *Nat. Methods* 9, 493-498 (2012).
4. Matsuda, T. & Cepko, C. L. Controlled expression of transgenes introduced by in vivo electroporation. *PNAS* 104, (2006).
5. Sarbassov, D. D., Ali, S. M. & Sabatini, D. M. Growing roles for the mTOR pathway. *Curr. Opin. Cell Biol.* 17, 596-603 (2005).
6. Rizzo, P. et al. Cross-talk between notch and the estrogen receptor in breast cancer suggests novel therapeutic approaches. *Cancer Res.* 68, 5226-5235 (2008).
7. Angelakis, E. et al. Abnormal weight gain and gut microbiota modifications are side effects of long-term doxycycline and hydroxychloroquine treatment. *Antimicrob. Agents Chemother.* 58, 3342-3347 (2014).
8. Keerthisinghe, T. P., Wang, M., Zhang, Y., Dong, W. & Fang, M. Low-dose tetracycline exposure alters gut bacterial metabolism and host-immune response: "Personalized" effect? *Environ. Int.* 131, 104989 (2019).
9. Garcia-gonzalez, A. P., Ritter, A. D., Shrestha, S. & Erik, C. Bacterial Metabolism Affects the *C. elegans* Response to Cancer Chemotherapeutics. *Cell* 169, 431-441 (2017).
10. Scott, T. A. et al. Host-Microbe Co-metabolism Dictates Cancer Drug Efficacy in *C. elegans. Cell* 169, 442-456.e18 (2017).
11. Gopalakrishnan, V. et al. Gut microbiome modulates response to anti-PD-1 immunotherapy in melanoma patients. *Science* (80). 359, 97-103 (2018).
12. Hill, Z. B., Martinko, A. J., Nguyen, D. P. & Wells, J. A. Human antibody-based chemically induced dimerizers for cell therapeutic applications. *Nat. Chem. Biol.* 14, 112-117 (2018).
13. Liang, F. Sen, Ho, W. Q. & Crabtree, G. R. Engineering the ABA Plant stress pathway for regulation of induced proximity. *Sci. Signal.* 4, 1-10 (2011).
14. Miyamoto, T. et al. Rapid and orthogonal logic gating with a gibberellin-induced dimerization system. *Nat. Chem. Biol.* 8, 465-470 (2012).
15. Tague, E. P., Dotson, H. L., Tunney, S. N., Sloas, D. C. & Ngo, J. T. Chemogenetic control of gene expression and cell signaling with antiviral drugs. *Nat. Methods* 15, 519-522 (2018).
16. Jacobs, C. L., Badiee, R. K. & Lin, M. Z. StaPLs: Versatile genetically encoded modules for engineering drug-inducible proteins. *Nat. Methods* 15, 523-526 (2018).
17. Nishikawa, F. et al. Inhibition of HCV NS3 protease by RNA aptamers in cells. *Nucleic Acids Res.* 31, 1935-1943 (2003).
18. Kügler, J. et al. High affinity peptide inhibitors of the hepatitis C virus NS3-4A protease refractory to common resistant mutants. *Biol. Chem.* 287, 39224-39232 (2012).
19. Cunningham-bryant, D. et al. A Chemically Disrupted Proximity System for Controlling Dynamic Cellular Processes. 8-11 (2019). doi:10.1021/jacs.8b12382
20. Foight, G. W. et al. cellular responses. *Nat. Biotechnol.* doi:10.1038/s41587-019-0242-8
21. Zhang, R. et al. Probing the substrate specificity of hepatitis C virus NS3 serine protease by using synthetic peptides. *J Virol* 71, 6208-6213 (1997).
22. Li, K. et al. Immune evasion by hepatitis C virus NS3/4A protease-mediated cleavage of the Toll-like receptor 3 adaptor protein TRIF. *Proc. Natl. Acad. Sci.* 102, 2992-2997 (2005).
23. Li, X.-D., Sun, L., Seth, R. B., Gabriel, P. & Chen, Z. J. Hepatitis C virus protease NS3/4A cleaves mitochondrial antiviral signaling protein off the mitochondria to evade innate immunity. *Proc Natl Acad Sci USA* 102, 17717-17722 (2005).
24. Pethe, M. A., Rubenstein, A. B. & Khare, S. D. Large-Scale Structure-Based Prediction and Identification of Novel Protease Substrates Using Computational Protein Design. *J Mol. Biol.* 429, 220-236 (2017).
25. Morsut, L. et al. Engineering Customized Cell Sensing and Response Behaviors Using Synthetic Notch Receptors. *Cell* 164, 780-791 (2016).
26. Roybal, K. T. et al. Precision Tumor Recognition by T Cells with Combinatorial Antigen-Sensing Circuits. *Cell* 164, 770-779 (2016).
27. Perni, R. B. et al. Preclinical profile of VX-950, a potent, selective, and orally bioavailable inhibitor of hepatitis C virus NS3-4A serine protease. *Antimicrob. Agents Chemother.* 50, 899-909 (2006).
28. Hagel, M. et al. Selective irreversible inhibition of a protease by targeting a noncatalytic cysteine. *Nat. Chem. Biol.* 7, 22-24 (2011).
29. Weinberg, B. H. et al. High-performance chemical and light-inducible recombinases in mammalian cells and mice. *bioRxiv* 747121 (2019). doi:10.1101/747121
30. Martin, S. S., Chu, V. C. & Baldwin, E. Modulation of the active complex assembly and turnover rate by protein-DNA interactions in Cre-LoxP recombination. *Biochemistry* 42, 6814-6826 (2003).
31. Serre, M. C. et al. The Carboxy-Terminal aN Helix of the Archaeal XerA Tyrosine Recombinase Is a Molecular Switch to Control Site-Specific Recombination. *PLoS One* 8, (2013).
32. Guo, F., Gopaul, D. N. & Van Duyne, G. D. Structure of Cre recombinase complexed with DNA in a site-specific recombination synapse. *Nature* 389, 40-46 (1997).
33. Ringrose, L. et al. Comparative kinetic analysis of FLP and Cre recombinases: Mathematical models for DNA binding and recombination. *J Mol. Biol.* 284, 363-384 (1998).
34. Eroshenko, N. & Church, G. M. Mutants of Cre recombinase with improved accuracy. *Nat. Commun.* 4, (2013).

35. Dickinson, B. C., Packer, M. S., Badran, A. H. & Liu, D. R. A system for the continuous directed evolution of proteases rapidly reveals drug-resistance mutations. *Nat. Commun.* 5, (2014).

36. Lee, T. S. et al. BglBrick vectors and datasheets: A synthetic biology platform for gene expression. *I Biol. Eng.* 5, 15-17 (2011)

Example 2

Figure 17:
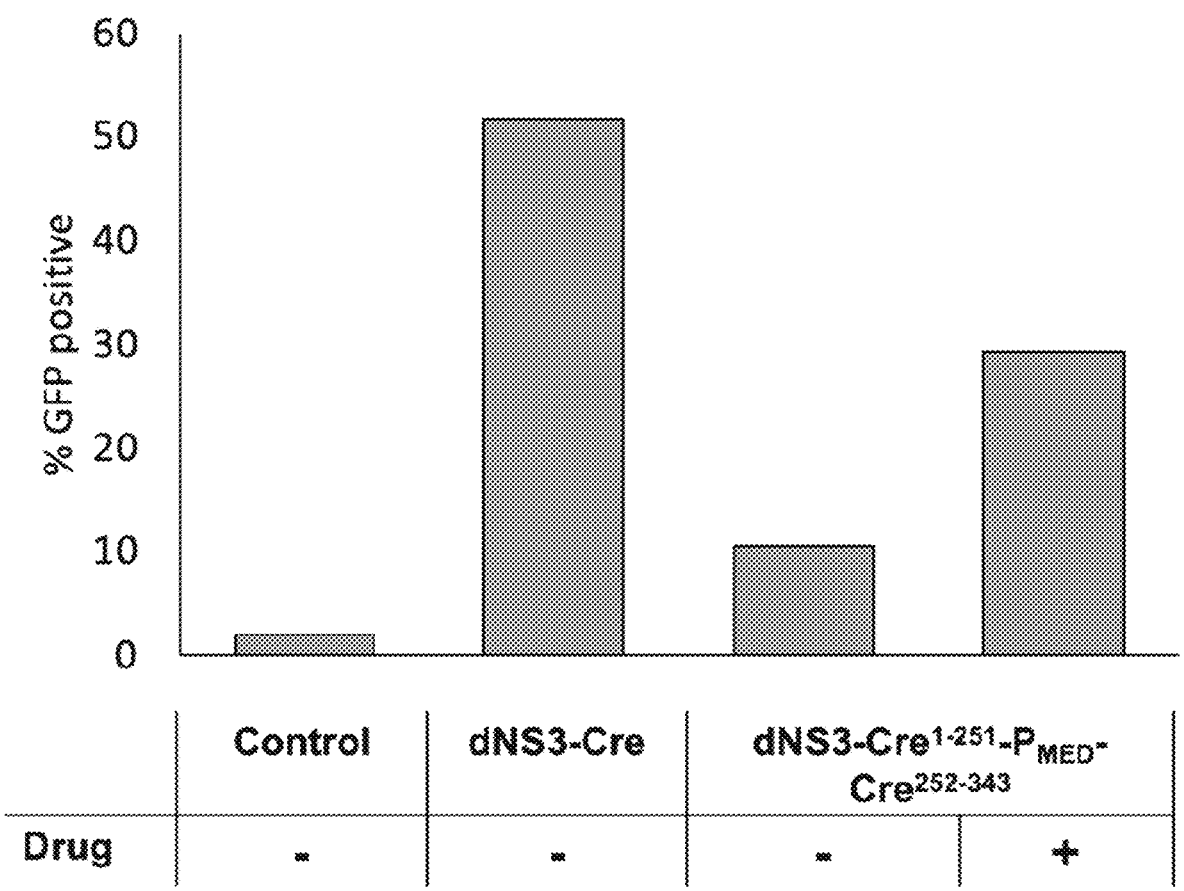
FIG. 17 depicts alternative placement of inhibitory peptide within the coding sequence of the Cre gene can result in drug dependent recombination. Drug dependent Cre, which has PMED peptide inserted after Cre amino acid 251, is compared to a transfection control producing iRFP only and a positive control of dNS3 fused to Cre. Cre recombination is measured here by flow cytometry as fraction of cells expressing GFP in a Cre stoplight reporter cell line, 48 hours post-transfection and drug addition. +Drug refers to 3 pM grazoprevir.

To validate that the inhibitory peptide can be inserted in different intramolecular positions in Cre, a chimeric Cre recombinase was constructed with dNS3 at the N-terminus and inhibitory peptide PMED inserted between Cre amino acids 251 and 252, a split site previously identified by Weinberg et al.1. Using this construct, the extent of recombination was controlled by small molecule NS3 inhibitor (FIG. 17).

Example 3

Summary of Potential Variations for NS3-Cre-Peptide Technology

The systems described herein can respond to multiple NS3 inhibitor drugs and high affinity peptides, including new high-affinity ligands that can bind inactive or active NS3 protease.

Some embodiments described herein comprise an NS3 domain that is catalytically inactive, but the construct can function with active NS3 and different NS3 genotypes.

Inducible Cre Recombinase Variations:

In Example 1, the NS3 and peptide are positioned at each termini of the Cre recombinase, but it has been shown previously that the peptide can be inserted within the Cre coding sequences at sites 228 and 251. These results indicate other intramolecular insertions of NS3 and/or peptide can block the catalytic activity of Cre in an antiviral drug dependent manner.

Other drug controlled peptide docking domains are also expected to work with this method such as BCL-xL protein, its high affinity binders, such as BAD, and higher affinity BCL-xL binding small molecules such as ABT-737.

Other protein domain interactions are also expected to work with this method. For example, a GFP affinity domain like LaG17 nanobody and intramolecular GFP/GFP(mutant) domain would be expected to cause intramolecular inhibition, and a higher affinity nanobody targeting an overlapping site of the fused GFP/GFP(mutant), or a higher affinity soluble GFP that is recognized by the integrated nanobody, are expected to competitively bind the LaG17 domain and "unlock" Cre enzymatic activity. The mechanism of conditional Cre inhibition is based around molecular constraint; therefore, the occluding domains should be modular.

Many tyrosine recombinases are structurally similar to Cre, composed of two distinct "N" and "C" terminus domains. This method of intramolecular inhibition may also be applicable to recombinases like XerD, XerA, and Flippase (Flp). Other mutations can be applied to Cre such as the CRE R32M and R32V point mutation to effect Cre specificity, function, or kinetics.

Drug Controlled SynNotch Activity:

The extracellular affinity domain can be replaced by other domains with affinity to different ligands, such as, but not limited to other nanobodies and single-chain variable fragments (scFvs). The extracellular protein localization sequence CD8a can be replaced with other extracellular localization sequences.

The DNA binding domain is expected to be replaceable with other DNA binding domains such as, but not limited to, TetR, rTetR, and zinc fingers. The transcriptional effector domain is expected to be replaceable with other transcriptional modulators such as, but not limited to, other activator domains, repressor domains, nuclease domains, and histone modification domains.

As shown in FIG. 1D, the high affinity peptide is attached to the SynNotch ICD, and the dNS3 is attached to the transcriptional modulator. It is expected that these domains can be swapped to have the dNS3 attached to the SynNotch ICD, and the high affinity peptide (CP5-46A-4D5E) is attached to the transcriptional modulator.

Example 4

Applications for NS3-Peptide Technology

The inducible Cre recombinase can be used in virtually any situation where drug inducible DNA recombination is desired, and it is advantageous in the fact that it is induced by an orthogonal ligand. Potential applications can be products such as:

A mouse line with genetically incorporated inducible Cre to study developmental biology phenomena. Current strategies often employ drugs like 4-hydroxytamoxifen, an estrogen receptor antagonist, or other non-orthogonal drugs like rapamycin, which effects the highly conserved mTOR pathway. Described herein is a much more precise way to knock out gene expression without as many off-target effects.

A genetically incorporated, drug inducible Cre to turn ON/OFF different receptors, or act as a kill switch to eliminate in chimeric antigen receptor (CAR) T-cells.

A genetically incorporated, drug inducible Cre to turn "kill switch" to eliminate cells that are resulting in adverse outcomes in cellular therapies like Chimeric antigen receptor (CAR) T-cells, or other gene therapies.

A bacterial strain with genetically incorporated inducible Cre or genetic incorporation kit sold to study an organism's gut microbiome. Many pharmaceutical companies would like to see how to recolonize the gut with beneficial microbes, or create a kill switch for biocontainment of therapeutic bacteria. Any of these concepts of drug inducible control can also be extended to biomanufacturing applications to facilitate the production of valuable biomolecules.

A genetically incorporated, drug inducible Cre to turn ON/OFF protein expression in microbial therapies in the gut microbiome.

Example 5

Products for Drug Controlled SynNotch

A CAR-T cell with genetically incorporated drug inducible SynNotch to control the "sensing" of tumor antigens.

Example 6

Gene and cellular therapies are increasingly advancing to the clinic; however, gene and protein regulation still remain an issue. As the biological complexity of these therapies become increasingly sophisticated, it is essential to develop mechanisms of precise control. Numerous methods have been developed to control gene expression and protein function by a chemical ligand, but most are derived from endogenous proteins to eukaryotes or prokaryotes, causing off-target effects to mammalian cells or host microbiomes. Described herein is a novel method to control cellular signaling, split enzyme recruitment, and intramolecular inhibition of a genetic recombinase through the use of Hepatitis C virus (HCV) NS3/4a protease and previously developed peptide inhibitors. By using NS3 protease, it is possible to employ the suite of antiviral drugs currently being used to treat HCV. In each use case, high affinity peptides are genetically encoded to bind to NS3 protease. Upon addition of higher affinity small molecule drug, the peptide is competitively displaced and inhibits peptide docking. Additionally, this technology does not require an active protease for conditional peptide docking, so a catalytically inactive mutant of NS3 can be employed, further reducing unwanted crosstalk with host cellular machinery.

NS3 protease and its antiviral drugs have been used to conditionally link domains of proteins together (Lin et al. PNAS, 2008; Chung et al., Nat. Chem. Bio. 2015; Tague, Dotson, Tunney et al. Nat. Met., 2018; Jacobs et al., Nat Met. 2018). In this scheme, the active protease acts as a self-excising linker between two domains, but upon addition of drug, this linker stays intact. With the new technology described herein, a catalytically inactive form of NS3 (hereafter called dNS3) and genetically encoded peptides are utilized (Kügler et al. JBC, 2012) to spontaneously bring two domains or two separate proteins together, and use antiviral drugs to conditionally inhibit this interaction. The technology described herein also utilizes unique structural knowledge of tyrosine recombinase Cre and other listed applications.

In one embodiment, described herein is a system to control the enzymatic activity of Cre recombinase using a catalytically inactive NS3 (dNS3) and high affinity peptide. The system includes a single protein construct dNS3-Cre (R32M/V)-CP5-46-4D5E containing:
  a. dNS3, which is catalytically inactive NS3 (S139A), at the N-terminus of Cre fused with a peptide linker composed of various amounts of flexible/hydrophilic amino acids.
  b. Wildtype Cre or mutant Cre(R32M or R32V) for high accuracy recombination
  c. High affinity peptide CP5-46-4D5E at the C-terminus of Cre fused with a peptide linker composed of various amounts of flexible/hydrophilic amino acids.

This is currently placed in a transiently expressed construct under a CAG promoter, but expression levels can be changed as needed. This construct can also be modulated to be genetically incorporated into cells by utilizing various methods such as viral incorporation, transposase incorporation, CRISPR methods, etc. By placing dNS3 and the peptide at opposing termini of Cre recombinase, intramolecular inhibition of the enzyme is provided. This intramolecular inhibition is reversed by a host of NS3 inhibitors, including grazoprevir, glecaprevir, danoprevir, asunaprevir, and other FDA approved drugs. Therefore, NS3 inhibitors cause drug induced genetic recombination.

Further described herein are two NS3-Cre-peptide constructs that specifically respond orthogonally to either asunaprevir and telaprevir. By utilizing mutations for active protease and a mutation of the catalytic serine of NS3 to make it catalytically "dead," these NS3s are able to bind the designed inhibitory peptides and control Cre enzyme function. The catalytically inactivating mutation also increased the orthogonality of the two inducible Cre systems.

Unlike the popular estrogen controlled Cre recombinase, this system does not rely on eukaryotic machinery and structures, so it can also be utilized in prokaryotic *E. coli*. Both eukaryotic and prokaryotic applications of this inducible Cre yielded low background recombination in the absence of drug, with high recombination in the presence of drug. The drug inducible Cre constructs presented here also offer advantage over split Cre constructs because these NS3 based Cre constructs are contained in a single protein, which provides a smaller genetic size and reduced complexity in expression.

Also described herein is a drug controllable SynNotch. dNS3 and high affinity peptide, CP5-46A-4D5E, can be used as a drug controllable intracellular domain (ICD) of a synthetic Notch cell signaling domain. SynNotch has previously been used to sense an extracellular ligand and subsequently trigger the release of a transcription factor ICD. Increased control over the ICD is provided herein by creating a SynNotch ICD composed of Gal4 DNA binding domain (DBD) fused to CP5-46A-4D5E peptide. When this ICD is released, the ICD becomes a DNA binding domain that can recruit modular NS3-fused transcriptional effectors to a transcriptional promoter (FIG. 1D). Unlike traditional SynNotch, this transcription complex is controllable by previously mentioned NS3 inhibitors that displace NS3 from the high affinity peptide and inhibit transcriptional modulation. With this, one can elicit dose-dependent transcriptional shut off of SynNotch despite presence of extracellular ligand.

The SynNotch receptor is comprised of constitutively expressed CD8a-myc tag-LaG17-Notch NRR-TMD-Gal4 (DBD)-CP5-46A-4D5E described below:
  d. An extracellular receptor (GFP antibody LaG17)
  e. An extracellular protein localization sequence CD8a
  f. Notch NRR and transmembrane domain
  g. Gal4 (DBD)-CP5-46A-4D5E
  h. Constitutively expressed dNS3-VPR Further described herein is a drug controllable split *Renilla luciferase*. In this regime, dNS3 is fused to NLuc (12-1247), and high affinity peptides CP5-46A-4D5E and CP5-46-4D5E were each separately fused to CLuc(1200-1643). In the absence of drug, luciferase activity is observed. Upon drug addition of NS3 inhibitors listed above, luciferase activity can be inhibited in a dose-dependent manner.

The technology described herein differs from the prior art and provides surprising advantages or solutions in at least the following ways. 1) unique structures providing genetic constraint of tyrosine recombinase Cre with dNS3 and high affinity peptide to create a drug inducible Cre. Unlike other inducible recombinases, this now uses presumably orthogonal antiviral drugs, many of which are FDA approved for HCV therapy. Furthermore, we have shown it can be used in eukaryotic and prokaryotic organisms with tight control and high accuracy. To our knowledge, this represents the first drug inducible bacterial recombinase. 2) The technology provides a drug controlled SynNotch for multi-input control of cellular signaling. This functions as a transcriptional turn-off switch of SynNotch, even in the presence of ligand. 3) The technology provides a drug inducible luciferase. In the absence of drug, a split *Renilla* luciferase is spontaneously formed via association of dNS3 and high affinity peptide. Upon addition of drug, split luciferase activity is inhibited.

What is claimed herein is:

1. A polypeptide comprising, from N-terminus to C-terminus:

i) a drug-controlled peptide docking domain, wherein the drug-controlled peptide docking domain is hepatitis C virus (HCV) nonstructural protein 3 (NS3);

ii) a cognate docking domain-binding peptide comprising medium affinity CP5-46A-4D5E (PMED) or high affinity CP5-46-4D5E ($P_{HI}$); and iii) a recombinase comprising at least one decreased cooperativity mutation, wherein the recombinase comprising at least one decreased cooperativity mutation is $Cre^{R32M}$ or $Cre^{R32V}$.

* * * * *

SEQUENCE LISTING

<160> NUMBER OF SEQ ID NOS: 193

<210> SEQ ID NO 1
<211> LENGTH: 233
<212> TYPE: PRT
<213> ORGANISM: Homo sapiens

<400> SEQUENCE: 1

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
        210                 215                 220

Leu Leu Gly Ser Leu Phe Ser Arg Lys
225                 230

<210> SEQ ID NO 2
<211> LENGTH: 170
<212> TYPE: PRT
<213> ORGANISM: Homo sapiens

<400> SEQUENCE: 2

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu

```
                    85                  90                  95

Phe Glu Leu Arg Tyr Arg Arg Ala Phe Ser Asp Leu Thr Ser Gln Leu
                100                 105                 110

His Ile Thr Pro Gly Thr Ala Tyr Gln Ser Phe Glu Gln Asp Thr Phe
            115                 120                 125

Val Glu Leu Tyr Gly Asn Asn Ala Ala Glu Ser Arg Lys Gly Gln
        130                 135                 140

Glu Arg Phe Asn Arg Trp Phe Leu Thr Gly Met Thr Val Ala Gly Val
145                 150                 155                 160

Val Leu Leu Gly Ser Leu Phe Ser Arg Lys
                165                 170

<210> SEQ ID NO 3
<211> LENGTH: 168
<212> TYPE: PRT
<213> ORGANISM: Homo sapiens

<400> SEQUENCE: 3

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
                100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
        130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Glu Leu Asp Glu Leu Val Tyr Leu Leu Asp Gly Pro Gly Tyr Asp
1               5                   10                  15

Pro Ile His Cys Asp Val Val Thr Arg Gly Gly Ser His Leu Phe Asn
            20                  25                  30

Phe

<210> SEQ ID NO 5
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Glu Leu Asp Glu Leu Val Tyr Leu Leu Asp Gly Pro Gly Tyr Asp
1               5                   10                  15

Pro Ile His Ser
            20

<210> SEQ ID NO 6
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ala Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 7
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu
225
```

<210> SEQ ID NO 8
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Ser Arg Val Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
50                  55                  60

Thr Thr Leu Thr Tyr Gly Val Gln Cys Phe Ser Arg Tyr Pro Asp His
65                  70                  75                  80

Met Lys Gln His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110
```

```
Ala Glu Val Lys Phe Glu Gly Asp Thr Leu Val Asn Arg Ile Glu Leu
            115                 120                 125

Lys Gly Ile Asp Phe Lys Glu Asp Gly Asn Ile Leu Gly His Lys Leu
130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr Leu Gly Met Asp Glu Leu Tyr
225                 230                 235                 240

Lys

<210> SEQ ID NO 9
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Thr Asn Leu Phe Leu Phe Leu Ile Phe Ser Leu Leu Leu Ser
1               5                   10                  15

Leu Ser Ser Ala Glu Phe Gly Ala Val Ser Lys Gly Glu Glu Leu Phe
            20                  25                  30

Gly Gly Ile Val Pro Ile Leu Val Glu Leu Glu Gly Asp Val Asn Gly
        35                  40                  45

His Lys Phe Ser Val Ser Gly Glu Gly Glu Gly Asp Ala Thr Tyr Gly
    50                  55                  60

Lys Leu Thr Leu Lys Phe Ile Cys Thr Thr Gly Lys Leu Pro Val Pro
65                  70                  75                  80

Trp Pro Thr Leu Val Thr Thr Leu Thr Trp Gly Val Gln Cys Phe Ser
                85                  90                  95

Arg Tyr Pro Asp His Met Lys Gln His Asp Phe Phe Lys Ser Val Met
            100                 105                 110

Pro Glu Gly Tyr Val Gln Glu Arg Thr Ile Phe Phe Lys Asp Asp Gly
        115                 120                 125

Asn Tyr Lys Thr Arg Ala Glu Val Lys Phe Glu Gly Asp Thr Leu Val
    130                 135                 140

Asn Arg Ile Glu Leu Lys Gly Ile Asp Phe Lys Glu Asp Gly Asn Ile
145                 150                 155                 160

Leu Gly His Lys Leu Glu Tyr Asn Tyr Ile Ser His Asn Val Tyr Ile
                165                 170                 175

Thr Ala Asp Lys Gln Lys Asn Gly Ile Lys Ala Asn Phe Lys Ala Arg
            180                 185                 190

His Asn Ile Thr Asp Gly Ser Val Gln Leu Ala Asp His Tyr Gln Gln
        195                 200                 205

Asn Thr Pro Ile Gly Asp Gly Pro Val Ile Leu Pro Asp Asn His Tyr
    210                 215                 220
```

Leu Ser Thr Gln Ser Ala Leu Ser Lys Asp Pro Asn Glu Lys Arg Asp
225                 230                 235                 240

His Met Val Leu Leu Glu Phe Val Thr Ala Ala Gly Ile Thr His Gly
                245                 250                 255

Met Asp Glu Leu Tyr Lys His Asp Glu Leu
            260                 265

<210> SEQ ID NO 10
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 11
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Val Ser Lys Gly Glu Glu Leu Phe Thr Gly Val Val Pro Ile Leu
1               5                   10                  15

```
Val Glu Leu Asp Gly Asp Val Asn Gly His Lys Phe Ser Val Ser Gly
         20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Phe Gly Tyr Gly Leu Gln Cys Phe Ala Arg Tyr Pro Asp His Met Lys
 65                  70                  75                  80

Leu His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 12
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Leu Ile Cys
         35                  40                  45

Thr Thr Gly Lys Leu Pro Val Pro Trp Pro Thr Leu Val Thr Thr Leu
 50                  55                  60

Gly Tyr Gly Leu Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

-continued

```
            130                 135                 140
Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Gly Glu Leu Asp Glu Leu Val Tyr Leu Leu Asp Gly Pro Gly Tyr Asp
1               5                   10                  15

Pro Ile His Ser
            20
```

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Gly Glu Leu Asp Glu Leu Val Tyr Leu Leu Asp Gly Pro Gly Tyr Asp
1               5                   10                  15

Pro Ile His Cys Asp Val Val Thr Arg Gly Gly Ser His Leu Phe Asn
            20                  25                  30

Phe
```

<210> SEQ ID NO 15
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
ttatcaaaaa gagtattgtc ttaaagtcta acctatagga ttcttacagc catcgagagg     60
gacacggcga a                                                          71

<210> SEQ ID NO 16
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
ttatcaaaaa gagtattgca ttaaagtcta acctatagga atcttacagc catcgagagg    60
gacacggcga a                                                          71

<210> SEQ ID NO 17
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttatcaaaaa gagtattgtc ttaaagtcta acctatagga aaattacagc catcgagagg    60
gacacggcga a                                                          71

<210> SEQ ID NO 18
<211> LENGTH: 60
<212> TYPE: PRT
<213> ORGANISM: Cricetulus barabensis

<400> SEQUENCE: 18

Met Pro Lys Lys Arg Lys Val Ser Asn Leu Leu Thr Val His Gln
1               5                   10                  15

Asn Leu Pro Ala Leu Pro Val Asp Ala Thr Ser Asp Glu Val Arg Lys
            20                  25                  30

Asn Leu Met Asp Met Phe Arg Asp Arg Gln Ala Phe Ser Glu His Thr
        35                  40                  45

Trp Lys Met Leu Leu Ser Val Cys Arg Ser Trp Ala
    50                  55                  60

<210> SEQ ID NO 19
<211> LENGTH: 53
<212> TYPE: PRT
<213> ORGANISM: Unknown
<220> FEATURE:
<223> OTHER INFORMATION: Description of Unknown:
      Enterobacteria phage P7 sequence

<400> SEQUENCE: 19

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 20
<211> LENGTH: 53
<212> TYPE: PRT
<213> ORGANISM: Unknown
<220> FEATURE:
<223> OTHER INFORMATION: Description of Unknown:
      Enterobacteria phage phiW39 sequence

<400> SEQUENCE: 20

Met Ser Asn Leu Leu Thr Val His Gln Asn Leu Pro Ala Leu Pro Val
1               5                   10                  15

```
Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 21
<211> LENGTH: 53
<212> TYPE: PRT
<213> ORGANISM: Unknown
<220> FEATURE:
<223> OTHER INFORMATION: Description of Unknown:
      Enterobacteriaceae bacterium 8376wB8 sequence

<400> SEQUENCE: 21

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 22
<211> LENGTH: 53
<212> TYPE: PRT
<213> ORGANISM: Unknown
<220> FEATURE:
<223> OTHER INFORMATION: Description of Unknown:
      Enterobacteriaceae bacterium 8376wD8 sequence

<400> SEQUENCE: 22

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 23
<211> LENGTH: 53
<212> TYPE: PRT
<213> ORGANISM: Unknown
<220> FEATURE:
<223> OTHER INFORMATION: Description of Unknown:
      Enterobacteriaceae bacterium 8376wD9 sequence

<400> SEQUENCE: 23

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50
```

-continued

```
<210> SEQ ID NO 24
<211> LENGTH: 53
<212> TYPE: PRT
<213> ORGANISM: Escherichia albertii

<400> SEQUENCE: 24

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 25
<211> LENGTH: 53
<212> TYPE: PRT
<213> ORGANISM: Escherichia coli

<400> SEQUENCE: 25

Met Ser Asn Val Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 26
<211> LENGTH: 53
<212> TYPE: PRT
<213> ORGANISM: Escherichia fergusonii

<400> SEQUENCE: 26

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 27
<211> LENGTH: 53
<212> TYPE: PRT
<213> ORGANISM: Escherichia sp.

<400> SEQUENCE: 27

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50
```

```
<210> SEQ ID NO 28
<211> LENGTH: 53
<212> TYPE: PRT
<213> ORGANISM: Unknown
<220> FEATURE:
<223> OTHER INFORMATION: Description of Unknown:
      Escherichia phage P1 sequence

<400> SEQUENCE: 28

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 29
<211> LENGTH: 53
<212> TYPE: PRT
<213> ORGANISM: Klebsiella pneumoniae

<400> SEQUENCE: 29

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 30
<211> LENGTH: 53
<212> TYPE: PRT
<213> ORGANISM: Salmonella sp.

<400> SEQUENCE: 30

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 31
<211> LENGTH: 53
<212> TYPE: PRT
<213> ORGANISM: Salmonella enterica

<400> SEQUENCE: 31

Met Thr Asn Ser Leu Thr Val His Gln Asn Leu Pro Ala Leu Pro Val
1               5                   10                  15

Glu Ser Val Asn Glu Glu Val Arg Arg Asn Leu Asn Ala Met Phe Arg
            20                  25                  30

Asp Lys Glu Ala Phe Ser Glu His Thr Trp Lys Met Leu Met Ser Val
        35                  40                  45
```

Cys Arg Ser Trp Ala
    50

<210> SEQ ID NO 32
<211> LENGTH: 53
<212> TYPE: PRT
<213> ORGANISM: Salmonella enterica

<400> SEQUENCE: 32

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 33
<211> LENGTH: 53
<212> TYPE: PRT
<213> ORGANISM: Salmonella enterica

<400> SEQUENCE: 33

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 34
<211> LENGTH: 53
<212> TYPE: PRT
<213> ORGANISM: Salmonella sp.

<400> SEQUENCE: 34

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 35
<211> LENGTH: 53
<212> TYPE: PRT
<213> ORGANISM: Salmonella sp.

<400> SEQUENCE: 35

Met Thr Asn Ser Leu Thr Val His Gln Asn Leu Leu Ala Leu Pro Val
1               5                   10                  15

Glu Ser Val Asn Glu Glu Val Leu Arg Asn Leu Asn Ala Met Phe Arg
            20                  25                  30

Asp Lys Glu Ala Phe Ser Glu His Thr Trp Lys Met Leu Met Ser Val

-continued

```
                35                  40                  45

Cys Arg Ser Trp Ala
    50

<210> SEQ ID NO 36
<211> LENGTH: 53
<212> TYPE: PRT
<213> ORGANISM: Salmonella sp.

<400> SEQUENCE: 36

Met Thr Asn Ser Leu Thr Val His Gln Asn Leu Pro Ala Leu Pro Val
1               5                   10                  15

Glu Ser Val Asn Glu Glu Val Arg Arg Asn Leu Asn Ala Met Phe Arg
            20                  25                  30

Asp Lys Glu Ala Phe Ser Glu His Thr Trp Lys Met Leu Met Ser Val
        35                  40                  45

Cys Arg Ser Trp Ala
    50

<210> SEQ ID NO 37
<211> LENGTH: 53
<212> TYPE: PRT
<213> ORGANISM: Unknown
<220> FEATURE:
<223> OTHER INFORMATION: Description of Unknown:
      Salmonella phage SJ46 sequence

<400> SEQUENCE: 37

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 38
<211> LENGTH: 53
<212> TYPE: PRT
<213> ORGANISM: Salmonella sp.

<400> SEQUENCE: 38

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 39
<211> LENGTH: 53
<212> TYPE: PRT
<213> ORGANISM: Salmonella typhimurium

<400> SEQUENCE: 39

Met Ser Asn Leu Leu Thr Val His Gln Asn Leu Pro Ala Leu Pro Val
1               5                   10                  15
```

Asp Ala Thr Ser Asp Glu Val Arg Lys Asn Leu Met Asp Met Phe Arg
            20                  25                  30

Asp Arg His Ala Phe Ser Glu His Thr Trp Lys Met Leu Leu Ser Val
        35                  40                  45

Cys Arg Ser Trp Ala
    50

<210> SEQ ID NO 40
<211> LENGTH: 53
<212> TYPE: PRT
<213> ORGANISM: Shigella dysenteriae

<400> SEQUENCE: 40

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 41
<211> LENGTH: 53
<212> TYPE: PRT
<213> ORGANISM: Shigella sonnei

<400> SEQUENCE: 41

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala
    50

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

```
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
```

<210> SEQ ID NO 58
<211> LENGTH: 343
<212> TYPE: PRT
<213> ORGANISM: Unknown
<220> FEATURE:
<223> OTHER INFORMATION: Description of Unknown:
      Cre reconbinase sequence

<400> SEQUENCE: 58

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 59
<211> LENGTH: 34
<212> TYPE: DNA
<213> ORGANISM: Unknown
<220> FEATURE:
<223> OTHER INFORMATION: Description of Unknown:
      LoxP sequence
<220> FEATURE:
<221> NAME/KEY: modified_base
<222> LOCATION: (14)..(16)
<223> OTHER INFORMATION: a, c, t, g, unknown or other
<220> FEATURE:
<221> NAME/KEY: modified_base
<222> LOCATION: (19)..(21)
<223> OTHER INFORMATION: a, c, t, g, unknown or other

<400> SEQUENCE: 59
ataacttcgt atannntann ntatacgaag ttat                                  34

<210> SEQ ID NO 60
<211> LENGTH: 423
<212> TYPE: PRT
<213> ORGANISM: Unknown
<220> FEATURE:
<223> OTHER INFORMATION: Description of Unknown:
      Flp or FlpO recombinase sequence

<400> SEQUENCE: 60

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu

```
                    245                 250                 255
Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
            325                 330                 335

Ala Val Ala Arg Thr Thr Tyr Thr His Gln Ile Thr Ala Ile Pro Asp
        340                 345                 350

His Tyr Phe Ala Leu Val Ser Arg Tyr Tyr Ala Tyr Asp Pro Ile Ser
    355                 360                 365

Lys Glu Met Ile Ala Leu Lys Asp Glu Thr Asn Pro Ile Glu Glu Trp
370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
            405                 410                 415

Ser Tyr Ile Asn Arg Arg Ile
            420

<210> SEQ ID NO 61
<211> LENGTH: 34
<212> TYPE: DNA
<213> ORGANISM: Unknown
<220> FEATURE:
<223> OTHER INFORMATION: Description of Unknown:
      FRT sequence

<400> SEQUENCE: 61
gaagttccta ttctctagaa agtataggaa cttc                              34

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65
<211> LENGTH: 380
<212> TYPE: PRT
<213> ORGANISM: Unknown
<220> FEATURE:
<223> OTHER INFORMATION: Description of Unknown:
      VCre recombinase sequence

<400> SEQUENCE: 65
```

```
Met Ile Glu Asn Gln Leu Ser Leu Leu Gly Asp Phe Ser Gly Val Arg
 1               5                   10                  15

Pro Asp Asp Val Lys Thr Ala Ile Gln Ala Ala Gln Lys Lys Gly Ile
             20                  25                  30

Asn Val Ala Glu Asn Glu Gln Phe Lys Ala Ala Phe Glu His Leu Leu
         35                  40                  45

Asn Glu Phe Lys Lys Arg Glu Arg Tyr Ser Pro Asn Thr Leu Arg
 50                  55                  60

Arg Leu Glu Ser Ala Trp Thr Cys Phe Val Asp Trp Cys Leu Ala Asn
 65                  70                  75                  80

His Arg His Ser Leu Pro Ala Thr Pro Asp Thr Val Glu Ala Phe Phe
             85                  90                  95

Ile Glu Arg Ala Glu Glu Leu His Arg Asn Thr Leu Ser Val Tyr Arg
             100                 105                 110

Trp Ala Ile Ser Arg Val His Arg Val Ala Gly Cys Pro Asp Pro Cys
             115                 120                 125

Leu Asp Ile Tyr Val Glu Asp Arg Leu Lys Ala Ile Ala Arg Lys Lys
 130                 135                 140

Val Arg Glu Gly Glu Ala Val Lys Gln Ala Ser Pro Phe Asn Glu Gln
 145                 150                 155                 160

His Leu Leu Lys Leu Thr Ser Leu Trp Tyr Arg Ser Asp Lys Leu Leu
             165                 170                 175

Leu Arg Arg Asn Leu Ala Leu Leu Ala Val Ala Tyr Glu Ser Met Leu
             180                 185                 190

Arg Ala Ser Glu Leu Ala Asn Ile Arg Val Ser Asp Met Glu Leu Ala
             195                 200                 205

Gly Asp Gly Thr Ala Ile Leu Thr Ile Pro Ile Thr Lys Thr Asn His
 210                 215                 220

Ser Gly Glu Pro Asp Thr Cys Ile Leu Ser Gln Asp Val Val Ser Leu
 225                 230                 235                 240

Leu Met Asp Tyr Thr Glu Ala Gly Lys Leu Asp Met Ser Ser Asp Gly
             245                 250                 255

Phe Leu Phe Val Gly Val Ser Lys His Asn Thr Cys Ile Lys Pro Lys
             260                 265                 270

Lys Asp Lys Gln Thr Gly Glu Val Leu His Lys Pro Ile Thr Thr Lys
 275                 280                 285

Thr Val Glu Gly Val Phe Tyr Ser Ala Trp Glu Thr Leu Asp Leu Gly
 290                 295                 300

Arg Gln Gly Val Lys Pro Phe Thr Ala His Ser Ala Arg Val Gly Ala
 305                 310                 315                 320

Ala Gln Asp Leu Leu Lys Lys Gly Tyr Asn Thr Leu Gln Ile Gln Gln
             325                 330                 335

Ser Gly Arg Trp Ser Ser Gly Ala Met Val Ala Arg Tyr Gly Arg Ala
             340                 345                 350

Ile Leu Ala Arg Asp Gly Ala Met Ala His Ser Arg Val Lys Thr Arg
             355                 360                 365

Ser Ala Pro Met Gln Trp Gly Lys Asp Glu Lys Asp
 370                 375                 380
```

<210> SEQ ID NO 66
<211> LENGTH: 34
<212> TYPE: DNA
<213> ORGANISM: Unknown
<220> FEATURE:

<223> OTHER INFORMATION: Description of Unknown: VLoxP sequence

<400> SEQUENCE: 66
tcaatttctg agaactgtca ttctcggaaa ttga    34

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77

```
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
```

000

<210> SEQ ID NO 89
<211> LENGTH: 189
<212> TYPE: PRT
<213> ORGANISM: Hepacivirus C

<400> SEQUENCE: 89

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
        35                  40                  45

Asn Gly Val Cys Trp Ala Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser
            180                 185
```

<210> SEQ ID NO 90
<211> LENGTH: 180
<212> TYPE: PRT
<213> ORGANISM: Hepacivirus C

<400> SEQUENCE: 90

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
        35                  40                  45

Asn Gly Val Cys Trp Thr Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125
```

```
Pro Arg Pro Ile Ser Tyr Leu Lys Gly Ser Ser Gly Gly Pro Leu Leu
            130                 135                 140

Cys Pro Ala Gly His Ala Val Gly Leu Phe Arg Ala Val Cys Thr
145                 150                 155                 160

Arg Gly Val Ala Lys Ala Val Asp Phe Ile Pro Val Glu Asn Leu Glu
                165                 170                 175

Thr Thr Met Arg
            180

<210> SEQ ID NO 91
<211> LENGTH: 180
<212> TYPE: PRT
<213> ORGANISM: Hepacivirus C

<400> SEQUENCE: 91

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
                20                  25                  30

Val Gln Val Val Ser Thr Ala Thr Gln Ser Phe Leu Ala Thr Cys Val
            35                  40                  45

Asn Gly Val Cys Trp Thr Val Tyr His Gly Ala Gly Ser Lys Thr Leu
50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
            115                 120                 125

Pro Arg Pro Val Ser Tyr Leu Lys Gly Ser Ser Gly Gly Pro Leu Leu
            130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg
            180

<210> SEQ ID NO 92
<211> LENGTH: 180
<212> TYPE: PRT
<213> ORGANISM: Hepacivirus C

<400> SEQUENCE: 92

Ala Pro Ile Thr Ala Tyr Ala Gln Gln Thr Arg Gly Leu Leu Gly Thr
1               5                   10                  15

Ile Val Val Ser Met Thr Gly Arg Asp Lys Thr Glu Gln Ala Gly Glu
                20                  25                  30

Ile Gln Val Leu Ser Thr Val Thr Gln Ser Phe Leu Gly Thr Ser Ile
            35                  40                  45

Ser Gly Val Leu Trp Thr Val Tyr His Gly Ala Gly Asn Lys Thr Leu
50                  55                  60

Ala Gly Ser Arg Gly Pro Val Thr Gln Met Tyr Ser Ser Ala Glu Gly
65                  70                  75                  80
```

Asp Leu Val Gly Trp Pro Ser Pro Pro Gly Thr Lys Ser Leu Glu Pro
                85                  90                  95

Cys Thr Cys Gly Ala Val Asp Leu Tyr Leu Val Thr Arg Asn Ala Asp
            100                 105                 110

Val Ile Pro Ala Arg Arg Arg Gly Asp Lys Arg Gly Ala Leu Leu Ser
            115                 120                 125

Pro Arg Pro Leu Ser Thr Leu Lys Gly Ser Ser Gly Pro Val Leu
130                 135                 140

Cys Pro Arg Gly His Ala Val Gly Val Phe Arg Ala Ala Val Cys Ser
145                 150                 155                 160

Arg Gly Val Ala Lys Ser Ile Asp Phe Ile Pro Val Glu Thr Leu Asp
                165                 170                 175

Ile Val Thr Arg
            180

<210> SEQ ID NO 93
<211> LENGTH: 180
<212> TYPE: PRT
<213> ORGANISM: Hepacivirus C

<400> SEQUENCE: 93

Ala Pro Ile Thr Ala Tyr Ala Gln Gln Thr Arg Gly Leu Leu Gly Thr
1               5                   10                  15

Ile Val Thr Ser Leu Thr Gly Arg Asp Lys Asn Val Val Thr Gly Glu
            20                  25                  30

Val Gln Val Leu Ser Thr Ala Thr Gln Thr Phe Leu Gly Thr Thr Val
            35                  40                  45

Gly Gly Val Ile Trp Thr Val Tyr His Gly Ala Gly Ser Arg Thr Leu
50                  55                  60

Ala Gly Ala Lys His Pro Ala Leu Gln Met Tyr Thr Asn Val Asp Gln
65                  70                  75                  80

Asp Leu Val Gly Trp Pro Ala Pro Pro Gly Ala Lys Ser Leu Glu Pro
                85                  90                  95

Cys Ala Cys Gly Ser Ser Asp Leu Tyr Leu Val Thr Arg Asp Ala Asp
            100                 105                 110

Val Ile Pro Ala Arg Arg Arg Gly Asp Ser Thr Ala Ser Leu Leu Ser
            115                 120                 125

Pro Arg Pro Leu Ala Cys Leu Lys Gly Ser Ser Gly Gly Pro Val Met
130                 135                 140

Cys Pro Ser Gly His Val Ala Gly Ile Phe Arg Ala Ala Val Cys Thr
145                 150                 155                 160

Arg Gly Val Ala Lys Ser Leu Gln Phe Ile Pro Val Glu Thr Leu Ser
                165                 170                 175

Thr Gln Ala Arg
            180

<210> SEQ ID NO 94
<211> LENGTH: 180
<212> TYPE: PRT
<213> ORGANISM: Hepacivirus C

<400> SEQUENCE: 94

Ala Pro Ile Thr Ala Tyr Ala Gln Gln Thr Arg Gly Leu Phe Ser Thr
1               5                   10                  15

Ile Val Thr Ser Leu Thr Gly Arg Asp Thr Asn Glu Asn Cys Gly Glu
            20                  25                  30

```
Val Gln Val Leu Ser Thr Ala Thr Gln Ser Phe Leu Gly Thr Ala Val
            35                  40                  45

Asn Gly Val Met Trp Thr Val Tyr His Gly Ala Gly Ala Lys Thr Ile
 50                      55                  60

Ser Gly Pro Lys Gly Pro Val Asn Gln Met Tyr Thr Asn Val Asp Gln
 65                  70                  75                  80

Asp Leu Val Gly Trp Pro Ala Pro Pro Gly Val Arg Ser Leu Ala Pro
                 85                  90                  95

Cys Thr Cys Gly Ser Ala Asp Leu Tyr Leu Val Thr Arg His Ala Asp
                100                 105                 110

Val Ile Pro Val Arg Arg Gly Asp Thr Arg Gly Ala Leu Leu Ser
            115                 120                 125

Pro Arg Pro Ile Ser Ile Leu Lys Gly Ser Ser Gly Pro Leu Leu
    130                 135                 140

Cys Pro Met Gly His Arg Ala Gly Ile Phe Arg Ala Ala Val Cys Thr
145                 150                 155                 160

Arg Gly Val Ala Lys Ala Val Asp Phe Val Pro Val Glu Ser Leu Glu
                165                 170                 175

Thr Thr Met Arg
            180

<210> SEQ ID NO 95
<211> LENGTH: 180
<212> TYPE: PRT
<213> ORGANISM: Hepacivirus C

<400> SEQUENCE: 95

Ala Pro Ile Thr Ala Tyr Ala Gln Gln Thr Arg Gly Val Leu Gly Ala
 1               5                  10                  15

Ile Val Leu Ser Leu Thr Gly Arg Asp Lys Asn Glu Ala Glu Gly Glu
            20                  25                  30

Val Gln Phe Leu Ser Thr Ala Thr Gln Thr Phe Leu Gly Ile Cys Ile
            35                  40                  45

Asn Gly Val Met Trp Thr Leu Phe His Gly Ala Gly Ser Lys Thr Leu
 50                      55                  60

Ala Gly Pro Lys Gly Pro Val Val Gln Met Tyr Thr Asn Val Asp Lys
 65                  70                  75                  80

Asp Leu Val Gly Trp Pro Ser Pro Pro Gly Lys Gly Ser Leu Thr Arg
                 85                  90                  95

Cys Thr Cys Gly Ser Ala Asp Leu Tyr Leu Val Thr Arg His Ala Asp
                100                 105                 110

Val Ile Pro Ala Arg Arg Gly Asp Thr Arg Ala Ser Leu Leu Ser
            115                 120                 125

Pro Arg Pro Ile Ser Tyr Leu Lys Gly Ser Ser Gly Gly Pro Ile Met
    130                 135                 140

Cys Pro Ser Gly His Val Val Gly Val Phe Arg Ala Ala Val Cys Thr
145                 150                 155                 160

Arg Gly Val Ala Lys Ala Leu Glu Phe Val Pro Val Glu Asn Leu Glu
                165                 170                 175

Thr Thr Met Arg
            180

<210> SEQ ID NO 96
<211> LENGTH: 180
<212> TYPE: PRT
<213> ORGANISM: Hepacivirus C
```

<400> SEQUENCE: 96

Ala Pro Ile Thr Ala Tyr Ala Gln Gln Thr Arg Gly Leu Val Gly Thr
1               5                   10                  15

Ile Val Thr Ser Leu Thr Gly Arg Asp Lys Asn Glu Ala Glu Gly Glu
            20                  25                  30

Val Gln Val Val Ser Thr Ala Thr Gln Ser Phe Leu Ala Thr Thr Ile
        35                  40                  45

Asn Gly Val Leu Trp Thr Val Tyr His Gly Ala Gly Ser Lys Asn Leu
    50                  55                  60

Ala Gly Pro Lys Gly Pro Val Cys Gln Met Tyr Thr Asn Val Asp Gln
65                  70                  75                  80

Asp Leu Val Gly Trp Pro Ala Pro Leu Gly Ala Arg Ser Leu Ala Pro
                85                  90                  95

Cys Thr Cys Gly Ser Ser Asp Leu Tyr Leu Val Thr Arg Gly Ala Asp
            100                 105                 110

Val Ile Pro Ala Arg Arg Arg Gly Asp Thr Arg Ala Ala Leu Leu Ser
        115                 120                 125

Pro Arg Pro Ile Ser Thr Leu Lys Gly Ser Ser Gly Gly Pro Leu Met
130                 135                 140

Cys Pro Ser Gly His Val Val Gly Leu Phe Arg Ala Ala Val Cys Thr
145                 150                 155                 160

Arg Gly Val Ala Lys Ala Leu Asp Phe Ile Pro Val Glu Asn Met Asp
                165                 170                 175

Thr Thr Met Arg
            180

<210> SEQ ID NO 97
<211> LENGTH: 180
<212> TYPE: PRT
<213> ORGANISM: Hepacivirus C

<400> SEQUENCE: 97

Ala Pro Ile Ser Ala Tyr Ala Gln Gln Thr Arg Gly Leu Ile Ser Thr
1               5                   10                  15

Leu Val Val Ser Leu Thr Gly Arg Asp Lys Asn Glu Thr Ala Gly Glu
            20                  25                  30

Val Gln Val Leu Ser Thr Ser Thr Gln Thr Phe Leu Gly Thr Asn Val
        35                  40                  45

Gly Gly Val Met Trp Gly Pro Tyr His Gly Ala Gly Thr Arg Thr Val
    50                  55                  60

Ala Gly Arg Gly Gly Pro Val Leu Gln Met Tyr Thr Ser Val Ser Asp
65                  70                  75                  80

Asp Leu Val Gly Trp Pro Ala Pro Pro Gly Ser Lys Ser Leu Glu Pro
                85                  90                  95

Cys Ser Cys Gly Ser Ala Asp Leu Tyr Leu Val Thr Arg Asn Ala Asp
            100                 105                 110

Val Leu Pro Leu Arg Arg Lys Gly Asp Gly Thr Ala Ser Leu Leu Ser
        115                 120                 125

Pro Arg Pro Val Ser Ser Leu Lys Gly Ser Ser Gly Gly Pro Val Leu
130                 135                 140

Cys Pro Gln Ser His Cys Val Gly Ile Phe Arg Ala Ala Val Cys Thr
145                 150                 155                 160

Arg Gly Val Ala Lys Ala Val Gln Phe Val Pro Ile Glu Lys Met Gln
                165                 170                 175

Val Ala Gln Arg
            180

<210> SEQ ID NO 98
<211> LENGTH: 180
<212> TYPE: PRT
<213> ORGANISM: Hepacivirus C

<400> SEQUENCE: 98

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
        35                  40                  45

Asn Gly Val Cys Trp Thr Val Tyr His Gly Ala Gly Thr Arg Thr Ile
    50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Thr Lys Ala Val Asp Phe Ile Pro Val Glu Asn Leu Glu
                165                 170                 175

Thr Thr Met Arg
            180

<210> SEQ ID NO 99
<211> LENGTH: 180
<212> TYPE: PRT
<213> ORGANISM: Hepacivirus C

<400> SEQUENCE: 99

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Ala Pro Lys Gly Pro Ile Thr Gln Met Tyr Thr Asn Val Asp Gln
65                  70                  75                  80

Asp Leu Val Gly Trp Pro Lys Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

```
Pro Arg Pro Val Ser Tyr Leu Lys Gly Ser Ser Gly Gly Pro Leu Leu
        130                 135                 140

Cys Pro Phe Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg
            180

<210> SEQ ID NO 100
<211> LENGTH: 180
<212> TYPE: PRT
<213> ORGANISM: Hepacivirus C

<400> SEQUENCE: 100

Ala Pro Ile Thr Ala Tyr Ala Gln Gln Thr Arg Gly Leu Leu Gly Thr
1               5                   10                  15

Ile Val Val Ser Met Thr Gly Arg Asp Lys Thr Glu Gln Ala Gly Glu
            20                  25                  30

Ile Gln Val Leu Ser Thr Val Thr Gln Ser Phe Leu Gly Thr Thr Ile
        35                  40                  45

Ser Gly Val Leu Trp Thr Val Tyr His Gly Ala Gly Asn Lys Thr Leu
    50                  55                  60

Ala Gly Ser Arg Gly Pro Val Thr Gln Met Tyr Ser Ser Ala Glu Gly
65                  70                  75                  80

Asp Leu Val Gly Trp Pro Ser Pro Gly Thr Lys Ser Leu Glu Pro
                85                  90                  95

Cys Thr Cys Gly Ala Val Asp Leu Tyr Leu Val Thr Arg Asn Ala Asp
                100                 105                 110

Val Ile Pro Ala Arg Arg Gly Asp Lys Arg Gly Ala Leu Leu Ser
            115                 120                 125

Pro Arg Pro Leu Ser Thr Leu Lys Gly Ser Ser Gly Gly Pro Val Leu
        130                 135                 140

Cys Pro Arg Gly His Ala Val Gly Val Phe Arg Ala Ala Val Cys Ser
145                 150                 155                 160

Arg Gly Val Ala Lys Ser Ile Asp Phe Ile Pro Val Glu Thr Leu Asp
                165                 170                 175

Ile Val Thr Arg
            180

<210> SEQ ID NO 101
<211> LENGTH: 180
<212> TYPE: PRT
<213> ORGANISM: Hepacivirus C

<400> SEQUENCE: 101

Ala Pro Ile Thr Ala Tyr Thr Gln Gln Thr Arg Gly Leu Leu Gly Ala
1               5                   10                  15

Ile Val Val Ser Leu Thr Gly Arg Asp Lys Asn Glu Gln Ala Gly Gln
            20                  25                  30

Val Gln Val Leu Ser Ser Val Thr Gln Thr Phe Leu Gly Thr Ser Ile
        35                  40                  45

Ser Gly Val Leu Trp Thr Val Tyr His Gly Ala Gly Asn Lys Thr Leu
    50                  55                  60

Ala Gly Pro Lys Gly Pro Val Thr Gln Met Tyr Thr Ser Ala Glu Gly
65                  70                  75                  80
```

Asp Leu Val Gly Trp Pro Ser Pro Pro Gly Thr Lys Ser Leu Asp Pro
                85                  90                  95

Cys Thr Cys Gly Ala Val Asp Leu Tyr Leu Val Thr Arg Asn Ala Asp
            100                 105                 110

Val Ile Pro Val Arg Arg Lys Asp Arg Arg Gly Ala Leu Leu Ser
        115                 120                 125

Pro Arg Pro Leu Ser Thr Leu Lys Gly Ser Ser Gly Pro Val Leu
    130                 135                 140

Cys Ser Arg Gly His Ala Val Gly Leu Phe Arg Ala Ala Val Cys Ala
145                 150                 155                 160

Arg Gly Val Ala Lys Ser Ile Asp Phe Ile Pro Val Glu Ser Leu Asp
                165                 170                 175

Val Ala Thr Arg
            180

<210> SEQ ID NO 102
<211> LENGTH: 180
<212> TYPE: PRT
<213> ORGANISM: Hepacivirus C

<400> SEQUENCE: 102

Ala Pro Ile Thr Ala Tyr Ala Gln Gln Thr Arg Gly Leu Leu Gly Thr
1               5                   10                  15

Ile Val Thr Ser Leu Thr Gly Arg Asp Lys Asn Val Val Thr Gly Glu
            20                  25                  30

Val Gln Val Leu Ser Thr Ala Thr Gln Thr Phe Leu Gly Thr Thr Val
        35                  40                  45

Gly Gly Val Ile Trp Thr Val Tyr His Gly Ala Gly Ser Arg Thr Leu
    50                  55                  60

Ala Gly Ala Lys His Pro Ala Leu Gln Met Tyr Thr Asn Val Asp Gln
65                  70                  75                  80

Asp Leu Val Gly Trp Pro Ala Pro Pro Gly Ala Lys Ser Leu Glu Pro
                85                  90                  95

Cys Ala Cys Gly Ser Ser Asp Leu Tyr Leu Val Thr Arg Asp Ala Asp
            100                 105                 110

Val Ile Pro Ala Arg Arg Gly Asp Ser Thr Ala Ser Leu Leu Ser
        115                 120                 125

Pro Arg Pro Leu Ala Cys Leu Lys Gly Ser Ser Gly Pro Val Met
    130                 135                 140

Cys Pro Ser Gly His Val Ala Gly Ile Phe Arg Ala Ala Val Cys Thr
145                 150                 155                 160

Arg Gly Val Ala Lys Ser Leu Gln Phe Ile Pro Val Glu Thr Leu Ser
                165                 170                 175

Thr Gln Ala Arg
            180

<210> SEQ ID NO 103
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ile Thr Ala Tyr Ser Gln Gln Thr Arg Gly Leu Leu Gly Cys Ile Ile
1               5                   10                  15

Thr Ser Leu Thr Gly Arg Asp Lys Asn Gln Val Glu Gly Glu Val Gln
            20                  25                  30

Val Val Ser Thr Ala Thr Gln Ser Phe Leu Ala Thr Cys Val Asn Gly
            35                  40                  45

Val Cys Trp Thr Val Tyr His Gly Ala Gly Ser Lys Thr Leu Ala Gly
50                  55                  60

Pro Lys Gly Pro Ile Thr Gln Met Tyr Thr Asn Val Asp Gln Asp Leu
65                  70                  75                  80

Val Gly Trp Gln Ala Pro Pro Gly Ala Arg Ser Leu Thr Pro Cys Thr
                85                  90                  95

Cys Gly Ser Ser Asp Leu Tyr Leu Val Thr Arg His Ala Asp Val Ile
            100                 105                 110

Pro Val Arg Arg Arg Gly Asp Ser Arg Gly Ser Leu Leu Ser Pro Arg
            115                 120                 125

Pro Val Ser Tyr Leu Lys Gly Ser Ala Gly Gly Pro Leu Leu Cys Pro
            130                 135                 140

Ser Gly His Ala Val Gly Ile Phe Arg Ala Ala Val Cys Thr Arg Gly
145                 150                 155                 160

Val Ala Lys Ala Val Asp Phe Val Pro Val Glu Ser Met Glu Thr Thr
                165                 170                 175

Met Arg Ser

<210> SEQ ID NO 104
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Thr Gln Thr Phe Leu Ala Thr Cys Ile
            35                  40                  45

Asn Gly Val Cys Trp Ala Val Tyr His Gly Ala Gly Thr Arg Thr Ile
50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
            115                 120                 125

Pro Arg Pro Ile Ser Tyr Leu Lys Gly Ser Ala Gly Gly Pro Leu Leu
            130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser
            180                 185

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

```
<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
<400> SEQUENCE: 126
000

<210> SEQ ID NO 127
```

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154
<211> LENGTH: 182
<212> TYPE: PRT
<213> ORGANISM: Hepacivirus C

<400> SEQUENCE: 154

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Lys Asp Leu Val Gly Trp Pro Ala Pro Gln Gly Ser Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser
            180
```

<210> SEQ ID NO 155
<211> LENGTH: 195
<212> TYPE: PRT
<213> ORGANISM: Hepacivirus C

<400> SEQUENCE: 155

```
Met Lys Lys Lys Gly Ser Val Val Ile Val Gly Arg Ile Val Leu Asn
1               5                   10                  15

Gly Ala Tyr Ala Gln Gln Thr Arg Gly Leu Leu Gly Cys Ile Ile Thr
            20                  25                  30

Ser Leu Thr Gly Arg Asp Lys Asn Gln Val Glu Gly Glu Val Gln Ile
        35                  40                  45

Val Ser Thr Ala Ala Gln Thr Phe Leu Ala Thr Cys Ile Asn Gly Val
    50                  55                  60

Cys Trp Thr Val Tyr His Gly Ala Gly Thr Arg Thr Ile Ala Ser Pro
65                  70                  75                  80

Lys Gly Pro Val Ile Gln Met Tyr Thr Asn Val Asp Lys Asp Leu Val
                85                  90                  95

Gly Trp Pro Ala Pro Gln Gly Ser Arg Ser Leu Thr Pro Cys Thr Cys
            100                 105                 110

Gly Ser Ser Asp Leu Tyr Leu Val Thr Arg His Ala Asp Val Ile Pro
        115                 120                 125

Val Arg Arg Arg Gly Asp Ser Arg Gly Ser Leu Leu Ser Pro Arg Pro
    130                 135                 140

Ile Ser Tyr Leu Lys Gly Ser Ser Gly Gly Pro Leu Leu Cys Pro Ala
145                 150                 155                 160

Gly His Ala Val Gly Ile Phe Arg Ala Ala Val Cys Thr Arg Gly Val
                165                 170                 175

Ala Lys Ala Val Asp Phe Ile Pro Val Glu Ser Leu Glu Thr Thr Met
                180                 185                 190

Arg Ser Pro
        195

<210> SEQ ID NO 156
<211> LENGTH: 195
<212> TYPE: PRT
<213> ORGANISM: Hepacivirus C

<400> SEQUENCE: 156

Met Lys Lys Lys Gly Ser Val Val Ile Val Gly Arg Ile Val Leu Asn
1               5                   10                  15

Gly Ala Tyr Ala Gln Gln Thr Arg Gly Glu Glu Gly Cys Gln Glu Thr
            20                  25                  30

Ser Gln Thr Gly Arg Asp Lys Asn Gln Val Glu Gly Glu Val Gln Ile
        35                  40                  45

Val Ser Thr Ala Ala Gln Thr Phe Leu Ala Thr Cys Ile Asn Gly Val
    50                  55                  60

Cys Trp Thr Val Tyr His Gly Ala Gly Thr Arg Thr Ile Ala Ser Pro
65                  70                  75                  80

Lys Gly Pro Val Ile Gln Met Tyr Thr Asn Val Asp Lys Asp Leu Val
                85                  90                  95

Gly Trp Pro Ala Pro Gln Gly Ser Arg Ser Leu Thr Pro Cys Thr Cys
            100                 105                 110

Gly Ser Ser Asp Leu Tyr Leu Val Thr Arg His Ala Asp Val Ile Pro
        115                 120                 125

Val Arg Arg Arg Gly Asp Ser Arg Gly Ser Leu Leu Ser Pro Arg Pro
    130                 135                 140

Ile Ser Tyr Leu Lys Gly Ser Ser Gly Gly Pro Leu Leu Cys Pro Ala
145                 150                 155                 160

Gly His Ala Val Gly Ile Phe Arg Ala Ala Val Cys Thr Arg Gly Val
```

```
                   165                 170                 175
Ala Lys Ala Val Asp Phe Ile Pro Val Glu Ser Leu Glu Thr Thr Met
                180                 185                 190

Arg Ser Pro
        195

<210> SEQ ID NO 157
<211> LENGTH: 197
<212> TYPE: PRT
<213> ORGANISM: Hepacivirus C

<400> SEQUENCE: 157

Met Lys Lys Lys Gly Ser Val Val Ile Val Gly Arg Ile Asn Leu Ser
1               5                   10                  15

Gly Asp Thr Ala Tyr Ala Gln Gln Thr Arg Gly Glu Glu Gly Cys Gln
                20                  25                  30

Glu Thr Ser Gln Thr Gly Arg Asp Lys Asn Gln Val Glu Gly Glu Val
                35                  40                  45

Gln Ile Val Ser Thr Ala Ala Gln Thr Phe Leu Ala Thr Cys Ile Asn
            50                  55                  60

Gly Val Cys Trp Thr Val Tyr His Gly Ala Gly Thr Arg Thr Ile Ala
65                  70                  75                  80

Ser Pro Lys Gly Pro Val Ile Gln Met Tyr Thr Asn Val Asp Lys Asp
                85                  90                  95

Leu Val Gly Trp Pro Ala Pro Gln Gly Ser Arg Ser Leu Thr Pro Cys
                100                 105                 110

Thr Cys Gly Ser Ser Asp Leu Tyr Leu Val Thr Arg His Ala Asp Val
                115                 120                 125

Ile Pro Val Arg Arg Arg Gly Asp Ser Arg Gly Ser Leu Leu Ser Pro
130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Cys Thr Arg
                165                 170                 175

Gly Val Ala Lys Ala Val Asp Phe Ile Pro Val Glu Ser Leu Glu Thr
                180                 185                 190

Thr Met Arg Ser Pro
            195

<210> SEQ ID NO 158
<211> LENGTH: 197
<212> TYPE: PRT
<213> ORGANISM: Hepacivirus C

<400> SEQUENCE: 158

Met Lys Lys Lys Gly Ser Val Val Ile Val Gly Arg Ile Asn Leu Ser
1               5                   10                  15

Gly Asp Thr Ala Tyr Ala Gln Gln Thr Arg Gly Glu Glu Gly Cys Gln
                20                  25                  30

Glu Thr Ser Gln Thr Gly Arg Asp Lys Asn Gln Val Glu Gly Glu Val
                35                  40                  45

Gln Ile Val Ser Thr Ala Thr Gln Thr Phe Leu Ala Thr Cys Ile Asn
            50                  55                  60

Gly Val Cys Trp Thr Val Tyr His Gly Ala Gly Thr Arg Thr Ile Ala
65                  70                  75                  80

Ser Pro Lys Gly Pro Val Thr Gln Met Tyr Thr Asn Val Asp Lys Asp
```

```
                85                  90                  95
Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
            115                 120                 125

Ile Pro Val Arg Arg Arg Gly Asp Ser Arg Gly Ser Leu Leu Ser Pro
            130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Cys Thr Arg
                165                 170                 175

Gly Val Ala Lys Ala Val Asp Phe Ile Pro Val Glu Ser Leu Glu Thr
                180                 185                 190

Thr Met Arg Ser Pro
                195

<210> SEQ ID NO 159
<211> LENGTH: 197
<212> TYPE: PRT
<213> ORGANISM: Hepacivirus C

<400> SEQUENCE: 159

Met Lys Lys Lys Gly Ser Val Val Ile Val Gly Arg Ile Asn Leu Ser
1               5                   10                  15

Gly Asp Thr Ala Tyr Ala Gln Gln Thr Arg Gly Glu Glu Gly Cys Gln
                20                  25                  30

Glu Thr Ser Gln Thr Gly Arg Asp Lys Asn Gln Val Glu Gly Glu Val
            35                  40                  45

Gln Ile Val Ser Thr Ala Thr Gln Thr Phe Leu Ala Thr Ser Ile Asn
50                  55                  60

Gly Val Leu Trp Thr Val Tyr His Gly Ala Gly Thr Arg Thr Ile Ala
65                  70                  75                  80

Ser Pro Lys Gly Pro Val Thr Gln Met Tyr Thr Asn Val Asp Lys Asp
                85                  90                  95

Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
            115                 120                 125

Ile Pro Val Arg Arg Arg Gly Asp Ser Arg Gly Ser Leu Leu Ser Pro
            130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Ser Thr Arg
                165                 170                 175

Gly Val Ala Lys Ala Val Asp Phe Ile Pro Val Glu Ser Leu Glu Thr
                180                 185                 190

Thr Met Arg Ser Pro
                195

<210> SEQ ID NO 160
<211> LENGTH: 197
<212> TYPE: PRT
<213> ORGANISM: Hepacivirus C

<400> SEQUENCE: 160

Met Lys Lys Lys Gly Ser Val Val Ile Val Gly Arg Ile Asn Leu Ser
```

```
            1               5                   10                  15
Gly Asp Thr Ala Tyr Ala Gln Gln Thr Arg Gly Glu Gln Gly Cys Gln
                    20                  25                  30

Lys Thr Ser His Thr Gly Arg Asp Lys Asn Gln Val Glu Gly Glu Val
                35                  40                  45

Gln Ile Val Ser Thr Ala Thr Gln Thr Phe Leu Ala Thr Ser Ile Asn
            50                  55                  60

Gly Val Leu Trp Thr Val Tyr His Gly Ala Gly Thr Arg Thr Ile Ala
65                      70                  75                  80

Ser Pro Lys Gly Pro Val Thr Gln Met Tyr Thr Asn Val Asp Lys Asp
                    85                  90                  95

Leu Val Gly Trp Gln Ala Pro Gln Gly Ser Arg Ser Leu Thr Pro Cys
                100                 105                 110

Thr Cys Gly Ser Ser Asp Leu Tyr Leu Val Thr Arg His Ala Asp Val
                115                 120                 125

Ile Pro Val Arg Arg Arg Gly Asp Ser Arg Gly Ser Leu Leu Ser Pro
            130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Ser Thr Arg
                    165                 170                 175

Gly Val Ala Lys Ala Val Asp Phe Ile Pro Val Glu Ser Leu Glu Thr
                180                 185                 190

Thr Met Arg Ser Pro
            195

<210> SEQ ID NO 161
<211> LENGTH: 197
<212> TYPE: PRT
<213> ORGANISM: Hepacivirus C

<400> SEQUENCE: 161

Met Lys Lys Lys Gly Ser Val Val Ile Val Gly Arg Ile Asn Leu Ser
1               5                   10                  15

Gly Asp Thr Ala Tyr Ala Gln Gln Thr Arg Gly Glu Gln Gly Thr Gln
                    20                  25                  30

Lys Thr Ser His Thr Gly Arg Asp Lys Asn Gln Val Glu Gly Glu Val
                35                  40                  45

Gln Ile Val Ser Thr Ala Thr Gln Thr Phe Leu Ala Thr Ser Ile Asn
            50                  55                  60

Gly Val Leu Trp Thr Val Tyr His Gly Ala Gly Thr Arg Thr Ile Ala
65                      70                  75                  80

Ser Pro Lys Gly Pro Val Thr Gln Met Tyr Thr Asn Val Asp Lys Asp
                    85                  90                  95

Leu Val Gly Trp Gln Ala Pro Gln Gly Ser Arg Ser Leu Thr Pro Cys
                100                 105                 110

Thr Cys Gly Ser Ser Asp Leu Tyr Leu Val Thr Arg His Ala Asp Val
                115                 120                 125

Ile Pro Val Arg Arg Arg Gly Asp Ser Arg Gly Ser Leu Leu Ser Pro
            130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Ser Thr Arg
                    165                 170                 175
```

```
Gly Val Ala Lys Ala Val Asp Phe Ile Pro Val Glu Ser Leu Glu Thr
            180                 185                 190

Thr Met Arg Ser Pro
        195

<210> SEQ ID NO 162
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Lys Lys Lys Gly Ser Val Val Ile Val Gly Arg Ile Asn Leu Ser Gly
1               5                   10                  15

Asp Thr Ala Tyr Ala Gln Gln Thr Arg Gly Glu Glu Gly Cys Gln Glu
            20                  25                  30

Thr Ser Gln Thr Gly Arg Asp Lys Asn Gln Val Glu Gly Glu Val Gln
        35                  40                  45

Ile Val Ser Thr Ala Thr Gln Thr Phe Leu Ala Thr Ser Ile Asn Gly
    50                  55                  60

Val Leu Trp Thr Val Tyr His Gly Ala Gly Thr Arg Thr Ile Ala Ser
65                  70                  75                  80

Pro Lys Gly Pro Val Thr Gln Met Tyr Thr Asn Val Asp Lys Asp Leu
                85                  90                  95

Val Gly Trp Gln Ala Pro Gln Gly Ser Arg Ser Leu Thr Pro Cys Thr
            100                 105                 110

Cys Gly Ser Ser Asp Leu Tyr Leu Val Thr Arg His Ala Asp Val Ile
        115                 120                 125

Pro Val Arg Arg Arg Gly Asp Ser Arg Gly Ser Leu Leu Ser Pro Arg
    130                 135                 140

Pro Ile Ser Tyr Leu Lys Gly Ser Ala Gly Gly Pro Leu Leu Cys Pro
145                 150                 155                 160

Ala Gly His Ala Val Gly Ile Phe Arg Ala Ala Val Ser Thr Arg Gly
                165                 170                 175

Val Ala Lys Ala Val Asp Phe Ile Pro Val Glu Ser Leu Glu Thr Thr
            180                 185                 190

Met Arg Ser Pro
        195

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166
```

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Pro Pro Gln Ile Glu Glu Ala Cys Glu Leu Pro Glu Cys Gln Val Asp
1               5                   10                  15

Ala Gly Asn Lys Val Cys Asn Leu Gln Cys Asn Asn His Ala Cys Gly
            20                  25                  30

Trp Asp Gly Gly Asp Cys Ser Leu Asn Phe Asn Asp Pro Trp Lys Asn
        35                  40                  45

Cys Thr Gln Ser Leu Gln Cys Trp Lys Tyr Phe Ser Asp Gly His Cys
    50                  55                  60

Asp Ser Gln Cys Asn Ser Ala Gly Cys Leu Phe Asp Gly Phe Asp Cys
65                  70                  75                  80

Gln Leu Thr Glu Gly Gln Cys Asn Pro Leu Tyr Asp Gln Tyr Cys Lys
                85                  90                  95

Asp His Phe Ser Asp Gly His Cys Asp Gln Gly Cys Asn Ser Ala Glu
            100                 105                 110

Cys Glu Trp Asp Gly Leu Asp Cys Ala Glu His Val Pro Glu Arg Leu
        115                 120                 125

Ala Ala Gly Thr Leu Val Leu Val Val Leu Leu Pro Pro Asp Gln Leu
    130                 135                 140

Arg Asn Asn Ser Phe His Phe Leu Arg Glu Leu Ser His Val Leu His
145                 150                 155                 160

Thr Asn Val Val Phe Lys Arg Asp Ala Gln Gly Gln Gln Met Ile Phe
                165                 170                 175

Pro Tyr Tyr Gly His Glu Glu Glu Leu Arg Lys His Pro Ile Lys Arg
            180                 185                 190

Ser Thr Val Gly Trp Ala Thr Ser Ser Leu Leu Pro Gly Thr Ser Gly
        195                 200                 205

Gly Arg Gln Arg Arg Glu Leu Asp Pro Met Asp Ile Arg Gly Ser Ile
    210                 215                 220

Val Tyr Leu Glu Ile Asp Asn Arg Gln Cys Val Gln Ser Ser Ser Gln
225                 230                 235                 240

Cys Phe Gln Ser Ala Thr Asp Val Ala Ala Phe Leu Gly Ala Leu Ala
                245                 250                 255

Ser Leu Gly Ser Leu Asn Ile Pro Tyr Lys Ile Glu Ala Val Lys Ser
            260                 265                 270

Glu Pro Val Glu Pro Pro Leu Pro Ser Gln Leu His Leu Met Tyr Val
        275                 280                 285

Ala Ala Ala Ala Phe Val Leu Leu Phe Phe Val Gly Cys Gly Val Leu
    290                 295                 300

Leu Ser
305
```

<210> SEQ ID NO 191
<211> LENGTH: 358
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His Ile Leu Asp Tyr Ser Phe Thr Gly Gly Ala Gly
        35                  40                  45

Arg Asp Ile Pro Pro Pro Gln Ile Glu Glu Ala Cys Glu Leu Pro Glu
50                  55                  60

Cys Gln Val Asp Ala Gly Asn Lys Val Cys Asn Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
            100                 105                 110

Asp Gly His Cys Asp Ser Gln Cys Asn Ser Ala Gly Cys Leu Phe Asp
        115                 120                 125

Gly Phe Asp Cys Gln Leu Thr Glu Gly Gln Cys Asn Pro Leu Tyr Asp
    130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Leu Val Val Leu Leu Pro
            180                 185                 190

Pro Asp Gln Leu Arg Asn Asn Ser Phe His Phe Leu Arg Glu Leu Ser
        195                 200                 205

His Val Leu His Thr Asn Val Val Phe Lys Arg Asp Ala Gln Gly Gln
    210                 215                 220

Gln Met Ile Phe Pro Tyr Tyr Gly His Glu Glu Glu Leu Arg Lys His
225                 230                 235                 240

Pro Ile Lys Arg Ser Thr Val Gly Trp Ala Thr Ser Ser Leu Leu Pro
                245                 250                 255

Gly Thr Ser Gly Gly Arg Gln Arg Arg Glu Leu Asp Pro Met Asp Ile
            260                 265                 270

Arg Gly Ser Ile Val Tyr Leu Glu Ile Asp Asn Arg Gln Cys Val Gln
        275                 280                 285

Ser Ser Ser Gln Cys Phe Gln Ser Ala Thr Asp Val Ala Ala Phe Leu
    290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Pro Leu Pro Ser Gln Leu His
                325                 330                 335

Leu Met Tyr Val Ala Ala Ala Ala Phe Val Leu Leu Phe Phe Val Gly
            340                 345                 350

Cys Gly Val Leu Leu Ser
        355
```

-continued

```
<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Asp Ile Val Pro Cys
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Glu Met Glu Glu Cys
1               5
```